United States Patent
DeKorver et al.

(10) Patent No.: US 9,686,984 B2
(45) Date of Patent: Jun. 27, 2017

(54) MACROCYCLIC PICOLINAMIDES AS FUNGICIDES

(71) Applicant: DOW AGROSCIENCES LLC, Indianapolis, IN (US)

(72) Inventors: Kyle A. DeKorver, Lafayette, IN (US); Johnathan E. DeLorbe, Pearland, TX (US); Kevin G. Meyer, Zionsville, IN (US); Chenglin Yao, Westfield, IN (US); Ronald J. Heemstra, Fishers, IN (US); Karla Bravo-Altamirano, Carmel, IN (US); John F. Daeuble, Sr., Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/793,315

(22) Filed: Jul. 7, 2015

(65) Prior Publication Data

US 2016/0007602 A1    Jan. 14, 2016

Related U.S. Application Data

(60) Provisional application No. 62/021,861, filed on Jul. 8, 2014.

(51) Int. Cl.
| | | |
|---|---|---|
| C07D 405/12 | (2006.01) | |
| A01N 43/40 | (2006.01) | |
| A01N 43/24 | (2006.01) | |
| C07D 321/00 | (2006.01) | |

(52) U.S. Cl.
CPC ............ *A01N 43/40* (2013.01); *A01N 43/24* (2013.01); *C07D 321/00* (2013.01); *C07D 405/12* (2013.01)

(58) Field of Classification Search
CPC .................................................. C07D 405/12
USPC ........................................................ 546/281.7
See application file for complete search history.

(56) References Cited

U.S. PATENT DOCUMENTS

| | | |
|---|---|---|
| 6,355,660 B1 | 3/2002 | Ricks |
| 6,521,622 B1 | 2/2003 | Ricks |
| 6,706,740 B2 | 3/2004 | Ricks |
| 6,861,390 B2 | 3/2005 | Meyer |
| 6,916,932 B2 | 7/2005 | Meyer et al. |
| 6,927,225 B2 | 8/2005 | Ricks |
| 7,034,035 B2 | 4/2006 | Ricks |
| 7,183,278 B1 | 2/2007 | Imamura |
| 7,250,389 B1 | 7/2007 | Sakanaka |
| 8,785,479 B2 | 7/2014 | Meyer |
| 8,835,462 B2 | 9/2014 | Meyer |
| 8,883,811 B2 | 11/2014 | Owen |
| 9,265,253 B2 | 2/2016 | Li et al. |
| 2002/0177578 A1 | 11/2002 | Ricks |
| 2003/0018012 A1 | 1/2003 | Ricks |
| 2003/0018052 A1 | 1/2003 | Ricks |
| 2003/0022902 A1 | 1/2003 | Ricks |
| 2003/0022903 A1 | 1/2003 | Ricks et al. |
| 2004/0034025 A1 | 2/2004 | Ricks |
| 2004/0048864 A1 | 3/2004 | Ricks |
| 2004/0171838 A1 | 9/2004 | Meyer et al. |
| 2004/0186296 A1 | 9/2004 | Niyaz |
| 2004/0192924 A1 | 9/2004 | Meyer et al. |
| 2005/0239873 A1 | 10/2005 | Hockenbery |
| 2006/0040995 A1 | 2/2006 | Bacque et al. |
| 2007/0060579 A1 | 3/2007 | Wachendorff-Neumann |
| 2007/0066629 A1 | 3/2007 | Blasco |
| 2008/0070985 A1 | 3/2008 | Derrer et al. |
| 2008/0293798 A1 | 11/2008 | Dietz |
| 2008/0318785 A1 | 12/2008 | Koltzenburg |
| 2009/0203770 A1 | 8/2009 | Hockenberry et al. |
| 2009/0306142 A1 | 12/2009 | Carson |
| 2011/0034493 A1 | 2/2011 | Boebel et al. |
| 2011/0053891 A1 | 3/2011 | Boebel et al. |
| 2011/0053966 A1 | 3/2011 | Klittich et al. |
| 2011/0082039 A1 | 4/2011 | Keeney et al. |
| 2011/0082160 A1 | 4/2011 | Owen |
| 2011/0082162 A1 | 4/2011 | Lorsbach et al. |
| 2011/0306644 A1 | 12/2011 | Hoekstra et al. |
| 2012/0035054 A1 | 2/2012 | Ehr et al. |
| 2012/0245031 A1 | 9/2012 | Gewehr et al. |
| 2013/0090298 A1 | 4/2013 | Lee et al. |

(Continued)

FOREIGN PATENT DOCUMENTS

| | | |
|---|---|---|
| CN | 102638989 | 8/2012 |
| EP | 1054011 | 11/2000 |

(Continued)

OTHER PUBLICATIONS

International Searching Authority, International Search Report and Written Opinion for PCT/US15/39409, dated Oct. 5, 2015, 14 pages.

(Continued)

*Primary Examiner* — Patricia L Morris

(74) *Attorney, Agent, or Firm* — Charles W. Arnett; Faegre Baker Daniels LLP

(57) ABSTRACT

This disclosure relates to macrocyclic picolinamides of Formula I and their use as fungicides.

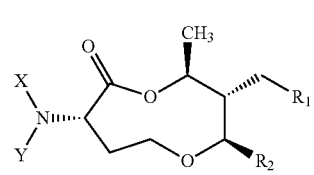

14 Claims, No Drawings

(56) References Cited

U.S. PATENT DOCUMENTS

| | | |
|---|---|---|
| 2013/0296371 A1 | 11/2013 | Meyer |
| 2013/0296372 A1 | 11/2013 | Owen et al. |
| 2013/0296373 A1 | 11/2013 | Meyer |
| 2013/0296374 A1 | 11/2013 | Owen et al. |
| 2013/0296375 A1 | 11/2013 | Meyer et al. |
| 2014/0128411 A1 | 5/2014 | Ogawa et al. |
| 2014/0187587 A1 | 7/2014 | Ouimette |
| 2014/0187588 A1 | 7/2014 | Lalonde |
| 2014/0187590 A1 | 7/2014 | Ouimette et al. |
| 2014/0275171 A1 | 9/2014 | Meyer |
| 2015/0065529 A1 | 3/2015 | Owen |
| 2015/0094341 A1 | 4/2015 | Li et al. |
| 2015/0183759 A1 | 7/2015 | DeLorbe et al. |

FOREIGN PATENT DOCUMENTS

| | | |
|---|---|---|
| EP | 1516874 | 3/2005 |
| WO | 01/14339 | 3/2001 |
| WO | WO 01/14365 | 3/2001 |
| WO | WO 03/011857 | 2/2003 |
| WO | WO 03/035617 | 5/2003 |
| WO | WO 2007017416 | 2/2007 |
| WO | 2009040397 | 9/2008 |
| WO | WO 2011028657 | 3/2011 |
| WO | WO 2011044213 | 4/2011 |
| WO | WO 2011069893 | 6/2011 |
| WO | WO 2012/016972 | 2/2012 |
| WO | WO 2012016989 | 2/2012 |
| WO | 2012/070015 | 5/2012 |
| WO | WO 2013/110002 | 7/2013 |
| WO | WO 2013/116251 | 8/2013 |
| WO | WO 2015/103161 | 7/2015 |

OTHER PUBLICATIONS

Gisi, U. The American Phytopathological Society, vol. 86, No. 11, 1996, p. 1273-79.
Anonymous, Synergistic Fungicidal Composition of Heterocyclic Aromatic Amides and Triazoles, IP.COM, Electronic Publication, 2004, 11 pages.
Anonymous, Synergistic Fungicidal Composition of Heterocyclic Aromatic Amides and Triazoles, IP.COM Journal, IP.COM, Inc., West Henrietta, NY, US, Dated Jul. 2004, 10 pages.
K. Tani, et al., Journal of Antibiotics, vol. 55, No. 3, Mar. 2002, pp. 315-321.
Z. Hu, et al, Synthesis of Novel Analogues of Antimycin A3, Tetrahedron Letters 49 (2008) pp. 5192-5195.
Y.Usuki, et al. Journal of Antibiotics, vol. 55, No. 6, Jun. 2002, pp. 607-610.
Kissling, Crop Protection pipeline value jumps to € 2.4 billion. BASF. Mar. 11, 2010, pp. 1-4, [retrieved on Feb. 4, 2014]. Retrieved from the Internet: <URL: http://www.agro.basf.com/agr/AP-Internet/en/content/news_room/news/basf-crop-protection-pipaline-value>.
BASF new fungicide Xemium got full approval in EU. AgroNews. Jul. 18, 2012 [retrieved on Jan. 20, Feb. 4, 2014). Retrieved from the Internet: <URL: http://news.agropages.com/News/NewsDetail—7386.htm>.
Masashi Ueki, et al., "UK-2A, B, C, and D, Novel Antifungal Antibiotics from *Streptomyces* sp. 517-02 I. Fermentation, Isolation, and Biological Properties," The Journal of Antibiotics, vol. 49, No. 7, Jul. 1996, pp. 639-643.
Koyanagi et al., "Bioisoterism, etc.," Synthesis and Chemistry of Agrochemicals IV; Baker, D. et al., 1995, 15-24.
Usuki, et al., "Semi-synthesis and biological evaluation of analogues of UK-2A, a novel antifungal antibiotic from *Steptomyces* sp. 517-02," Bioorganic & Medicinal Chemistry Letters, Pergamon, Amsterdam, KL, vol. 15, No. 8, Apr. 15, 2005, pp. 2011-2014, XP027801790.
PUBCHEM, Substance Record for SID 74383515. Deposit Date Jun. 11, 2009 [retrieved on May 25, 2016] Retrieved from internet. <URL:https://pubchem.ncbi.nlm.nih.gov/substance/74383515#section=Top>.
Huang, et al., Synergistic Interactions between Chitinase ChiCW and Fungicides Against Plant Fungal Pathogens, J. Microbiol. Biotechnol., 2008, 18(4) 784-787.
Backman, P., Fungicide Formulation: Relationship to Biological Activity, 1978, 16, 211-237.
Latin, et al, Re-Examining Fungicide Synergism for Dollar Spot Control, GCM, 2008, 84-87.
O'Sullivan, et al., Fungicide Resistance—An Increasing Problem, Proceedings of National Tillage Conference 2007, Published by Crop Research Centre Oak Park Carlow, date Jan. 31, 2007, 14 pages.

MACROCYCLIC PICOLINAMIDES AS FUNGICIDES

CROSS REFERENCE TO RELATED APPLICATIONS

This application claims the benefit of U.S. Provisional Patent Application Ser. No. 62/021,861 filed Jul. 8, 2014, which is expressly incorporated by reference herein.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to macrocyclic picolinamides and their use as fungicides. The compounds of the present disclosure may offer protection against ascomycetes, basidiomycetes, deuteromycetes and oomycetes.

One embodiment of the present disclosure may include compounds of Formula I:

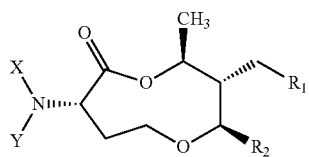

wherein
X is hydrogen or $C(O)R_3$;
Y is hydrogen, $C(O)R_3$, or Q;
Q is

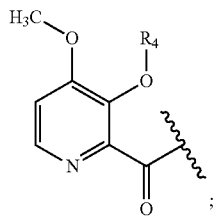

wherein
$R_1$ is hydrogen, alkyl, alkenyl, aryl, heterocyclyl, alkoxy, or acyl, each optionally substituted with 0, 1 or multiple $R_6$;
$R_2$ is hydrogen, alkyl, alkenyl, aryl, or acyl, each optionally substituted with 0, 1 or multiple $R_6$;
$R_3$ is alkoxy or benzyloxy, each optionally substituted with 0, 1, or multiple $R_6$;
$R_4$ is hydrogen, $—C(O)R_5$, or $—CH_2OC(O)R_5$;
$R_5$ is alkyl, alkoxy, or aryl, each optionally substituted with 0, 1, or multiple $R_6$;
$R_6$ is hydrogen, alkyl, aryl, acyl, halo, alkenyl, alkoxy, heterocyclyl, or thioalkyl, each optionally substituted with 0, 1, or multiple $R_7$;
$R_7$ is hydrogen, alkyl, aryl, or halo.

In some embodiments the compound of Formula I includes X equal to H and Y equal to H; in some of these embodiments $R_1$ is alkyl or aryl, each optionally substituted with 0, 1 or multiple $R_6$; in some of these embodiments $R_2$ is hydrogen or alkyl, each optionally substituted with 0, 1 or multiple $R_6$.

In some embodiments the compounds of Formula I includes X equal $C(O)R_3$ and Y equal to H, in some of these embodiments $R_1$ is alkyl or aryl, each optionally substituted with 0, 1 or multiple $R_6$; in some of these embodiments $R_2$ is hydrogen or alkyl, each optionally substituted with 0, 1 or multiple $R_6$.

In some embodiments the compounds of Formula I includes X equal to H and Y equal to Q; in some of these embodiments $R_1$ is alkyl or aryl, each optionally substituted with 0, 1 or multiple $R_6$; in some embodiments $R_2$ is hydrogen or alkyl, each optionally substituted with 0, 1 or multiple $R_6$; in some embodiments $R_4$ is either H or $—C(O)R_5$ or $—CH_2OC(O)R_5$; in some of these embodiments $R_5$ is alkyl or alkoxy, each optionally substituted with 0, 1, or multiple $R_6$, or $R_5$ is $—CH_3$, $—CH(CH_3)_2$, $—CH_2OCH_2CH_3$, or $—CH_2CH_2OCH_3$.

Other embodiments of the present disclosure may include a fungicidal composition for the control or prevention of fungal attack comprising the compounds described above and a phytologically acceptable carrier material.

Yet other embodiments of the present disclosure may include a method for the control or prevention of fungal attack on a plant, the method including the steps of applying a fungicidally effective amount of one or more of the compounds described above to at least one of the fungus, the plant, and an area adjacent to the plant.

The compounds for Formula I and compostions including the same as identified herein may be used to control and or prevention of at least one pathogen such as those selected from the list consisting of: Leaf Blotch of Wheat (*Mycosphaerella graminicola*; anamorph: *Zymoseptoria tritici*), Wheat Brown Rust (*Puccinia triticina*), Stripe Rust (*Puccinia striiformis*), Scab of Apple (*Venturia inaequalis*), Blister Smut of Maize (*Ustilago maydis*), Powdery Mildew of Grapevine (*Uncinula necator*), Barley Scald (*Rhynchosporium secalis*), Blast of Rice (*Magnaporthe grisea*), Rust of Soybean (*Phakopsora pachyrhizi*), Glume Blotch of Wheat (*Leptosphaeria nodorum*), Powdery Mildew of Wheat (*Blumeria graminis* f. sp. *tritici*), Powdery Mildew of Barley (*Blumeria graminis* f. sp. *hordei*), Powdery Mildew of Cucurbits (*Erysiphe cichoracearum*), Anthracnose of Cucurbits (*Glomerella lagenarium*), Leaf Spot of Beet (*Cercospora beticola*), Early Blight of Tomato (*Alternaria solani*), and Net Blotch of Barley (*Pyrenophora teres*).

Still other embodiments include A method for the control and/or the prevention of fungal attack on a plant, these methods including the step of: applying a fungicidally effective amount of at least one of the compounds of Formula I, or a composition that includes at least one compound of Formula I to at least one portion of a plant, an area adjacent to the plant, soil adapted to support growth of the plant, a root of the plant, and at least a portion of foliage of the plant. In some embodiments the composition includes at least one additional compound selected from the group consisting of a phytologically acceptable carrier material, a second fungicide, an insecticide, a nematocide, a miticide, an arthropodicide, and a bactericide.

It will be understood by those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl, and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The term "alkynyl" refers to a branched or unbranched carbon chain containing one or more triple bonds including, but not limited to, propynyl, butyryl, and the like.

The terms "aryl" and "Ar" refer to any aromatic ring, mono- or bi-cyclic, containing 0 heteroatoms.

The term "heterocyclyl" refers to any aromatic or non-aromatic ring, mono- or bi-cyclic, containing one or more heteroatoms The term "alkoxy" refers to an —OR substituent.
The term "acyloxy" refers to an —OC(O)R substituent.
The term "cyano" refers to a —C≡N substituent.
The term "hydroxyl" refers to an —OH substituent.
The term "amino" refers to a —N(R)$_2$ substituent.
The term "arylalkoxy" refers to —O(CH$_2$)$_n$—Ar where n is an integer selected from the list 1, 2, 3, 4, 5, or 6.

The term "haloalkoxy" refers to an —OR—X substituent, wherein X is Cl, F, Br, or I, or any combination thereof.

The term "haloalkyl" refers to an alkyl, which is substituted with Cl, F, I, or Br or any combination thereof.

The term "halogen" or "halo" refers to one or more halogen atoms, defined as F, Cl, Br, and I.

The term "nitro" refers to a —NO$_2$ substituent.
The term thioalkyl refers to an —SR substituent.

Throughout the disclosure, reference to the compounds of Formula I is read as also including diastereomers, enantiomers, and mixtures thereof. In another embodiment, Formula (I) is read as also including salts or hydrates thereof. Exemplary salts include, but are not limited to: hydrochloride, hydrobromide, and hydroiodide.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting, and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzyl-cocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis, Bacillus subtilis* strain QST713, benalaxyl, benomyl, benthiavalicarb-isopropyl, benzovindiflupyr benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquation, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, diallate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halauxifen, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those skilled in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Mycosphaerella graminicola*; anamorph: *Septoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Magnaporthe grisea*), rust of soybean (*Phakopsora pachyrhizi*), glume blotch of wheat (*Leptosphaeria nodorum*), powdery mildew of wheat (*Blumeria graminis* f sp. *tritici*), powdery mildew of barley (*Blumeria graminis* f sp. *hordei*), powdery mildew of cucurbits (*Erysiphe cichoracearum*), anthracnose of cucurbits (*Glomerella lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating picolinamide compounds of Formula (I). The following descriptions and examples are provided for illustrative purposes and should not be construed as limiting in terms of substituents or substitution patterns.

Compounds of Formula 1.3, where $R_1$ is as originally defined, can be prepared according to the methods outlined in Scheme 1, steps a-c. Compounds of Formula 1.1, where $R_1$ is as originally defined, can be obtained by reaction of the dianion of an ester of Formula 1.0 formed by treatment with lithium diisopropyl amide (LDA) at −50° C., with an alkyl halide or allyl halide in a solvent such as tetrahydrofuran (THF) at cryogenic temperatures such as −78° C., as shown in a. Compounds of Formula 1.2, where $R_1$ is as originally defined, can be obtained by treating compounds of Formula 1.1, where $R_1$ is an alkenyl functionality, with hydrogen gas ($H_2$) in the presence of a catalyst such as palladium on carbon (Pd/C) in a solvent such as ethyl acetate (EtOAc) or methanol (MeOH), as shown in b. Compounds of Formula 1.3, where $R_1$ is orignally defined, can be prepared from compounds of Formula 1.1, where $R_1$ is as defined above, and Formula 1.2, where $R_1$ is as defined above, by treating with an alkylating agent such as 4-methoxybenzyl 2,2,2-trichloroacetimidate in the presence of an acid such as ((1S,4R)-7,7-dimethyl-2-oxobicyclo[2.2.1]heptan-1-yl)methanesulfonic acid (camphor sulfonic acid, CSA) in a solvent such as dichloromethane (DCM), as depicted in c.

Scheme 1

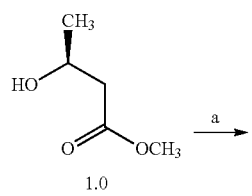

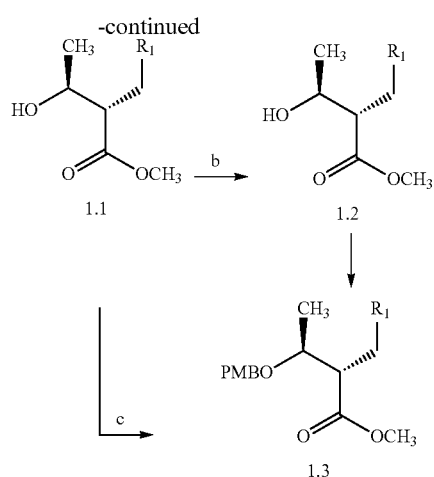

Compounds of Formulas 2.3 and 2.4, where $R_1$ and $R_2$ are as originally defined can be prepared as shown in Scheme 2, steps a-e. Aldehydes of Formula 2.0, where $R_1$ is as originally defined, can be obtained by the reduction of esters of Formula 1.3, where $R_1$ is as defined above, using a catalyst such as chlorobis(cyclooctene)iridium(I) dimer in the presence of a reducing agent such as diethylsilane ($Et_2SiH_2$) in a solvent such as DCM, as shown in a. Alcohols of Formula 2.1, where $R_1$ and $R_2$ are as originally defined, can be obtained by treatment of aldehydes of Formula 2.0, where $R_1$ is as defined above, with a nucleophile, such as benzyl magnesium chloride, vinyl magnesium bromide, and allyl magnesium bromide, in a solvent such as THF at a temperature of about 0° C. or −78° C. as shown in b. Alcohols of Formula 2.1, with $R_1$ and $R_2$ as defined above can be oxidized with an oxidizing agent such as Dess-Martin periodinane (DMP) in a solvent such as DCM to afford compounds of Formula 2.2, where $R_1$ and $R_2$ are as originally defined as shown in c. Alcohols of Formula 2.3, where $R_1$ and $R_2$ are as previously defined, can be prepared from ketones of Formula 2.2, where $R_1$ and $R_2$ are as defined above, by treatment with a reducing agent such as borane dimethyl sulfide ($BH_3$-DMS) in the presence of a chiral catalyst such as (S)-1-methyl-3,3-diphenylhexahydropyrrolo[1,2-c][1,3,2]oxazaborole in a solvent such as toluene as depicted in d. Alcohols of 2.4, where $R_1$ is as previously defined, can be prepared as shown in e from esters of Formula 1.3, where $R_1$ is as originally defined, by treatment with a reducing agent such as lithium aluminum hydride (LAH) in a solvent such as THF at a temperature between about 0° C. and 23° C.

Scheme 2

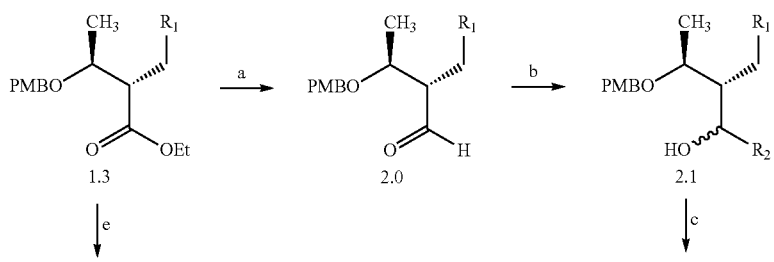

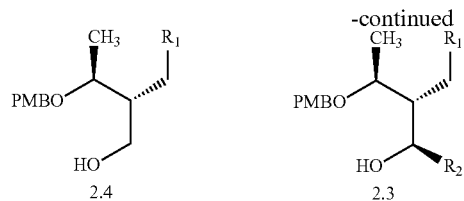
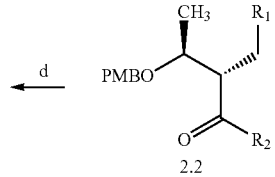

Compounds of Formula 3.2, where $R_1$ and $R_2$ are as originally defined, but $R_2$ is not alkenyl, can be prepared according to the methods outlined in Scheme 3, steps a-c. Alcohols of Formula 2.3, where $R_1$ and $R_2$ are as originally defined, but $R_2$ is not alkenyl, can be treated with a base such as sodium hydride (NaH) and an allylic halide such as allyl bromide in a polar, aprotic solvent such as THF or N,N-dimethylformamide (DMF) to afford compounds of Formula 3.0, where $R_1$ and $R_2$ are as originally defined, as shown in a. Compounds of Formula 3.1, where $R_1$ and $R_2$ are as originally defined, but $R_2$ is not alkenyl, can be prepared from compounds of Formula 3.0, where $R_1$ and $R_2$ are as previously defined, by treating with ozone in a solvent mixture such as DCM and MeOH, followed by quenching with a reducing agent such as triphenylphosphine ($PPh_3$) as shown in b. Compounds of Formula 3.1, where $R_1$ and $R_2$ are as defined above, can be treated with an glide precursor such as methyl 2-((tert-butoxycarbonyl)amino)-2-(dimethoxyphosphoryl)acetate and a base such as 1,8-diazabicyclo[5.4.0]undec-7-ene (DBU) in a halogenated solvent such as DCM to afford compounds of Formula 3.2, where $R_1$ and $R_2$ are as previously defined, as shown in c.

Compounds of Formula 4.1, 4.4 and 4.5, where $R_1$ and $R_6$ are as originally defined, can be prepared according to the methods outlined in Scheme 4, steps a-e. Alcohols of Formula 2.3, where $R_1$ is as originally defined, can be treated with a base such as NaH and a reagent such as 2-bromo-1,1-diethoxyethane in a solvent such as DMF, acetonitrile ($CH_3CN$), or mixtures thereof at a temperature of about 50° C. to afford compounds of Formula 4.0, where $R_1$ is as originally defined, as depicted in a. Compounds of Formula 4.1, where $R_1$ and $R_6$ are as originally defined can be prepared as shown in b from compounds of Formula 4.0, where $R_1$ is as previously defined, by first treating with 9-borabicyclo[3.3.1]nonane (9-BBN) in a solvent such as THF, then with an aqueous alkaline solution such as potassium phosphate in water, a palladium catalyst such as [1,1'-bis(diphenylphosphino)ferrocene]dichloropalladium (II) ($Cl_2Pd(dppf)$), and an alkenyl or aryl halide such as vinyl bromide or bromobenzene and a solvent such as DMF at a temperature of about 50° C. Compounds of Formula 4.2, where $R_1$ is as originally defined, can be obtained from compounds of Formula 4.0, where $R_1$ is as previously defined, by treating with 9-BBN in a solvent such as THF followed by an oxidizing agent such as an aqueous hydrogen peroxide ($H_2O_2$) solution, as shown in c. Alternatively, alcohols of Formula 4.3, where $R_1$ is as originally defined, can be obtained by subjecting compounds of Formula 4.0, where $R_1$ is as previously defined, to ozone in a solvent mixture such as DCM and MeOH at a temperature such as −78° C. and then quenching with a reducing agent such as sodium borohydride ($NaBH_4$), as depicted in d. Alcohols of Formula 4.2 and 4.3, where $R_1$ is as previously defined, can be arylated using an arylating agent such as diacetoxy(triphenyl)bismuth, a catalyst such as diacetoxycopper, and a base, such as N,N-dicyclohexylmethylamine, in a solvent such as toluene at a temperature of about 60° C. or alkylated by treating with a base such as NaH and an alkyl halide such as methyl iodide (iodomethane, MeI) in as solvent such as THF to afford compounds of Formula 4.4 and 4.5, where $R_1$ is as originally defined and $R_6$ is aryl or alkyl, as depicted in e.

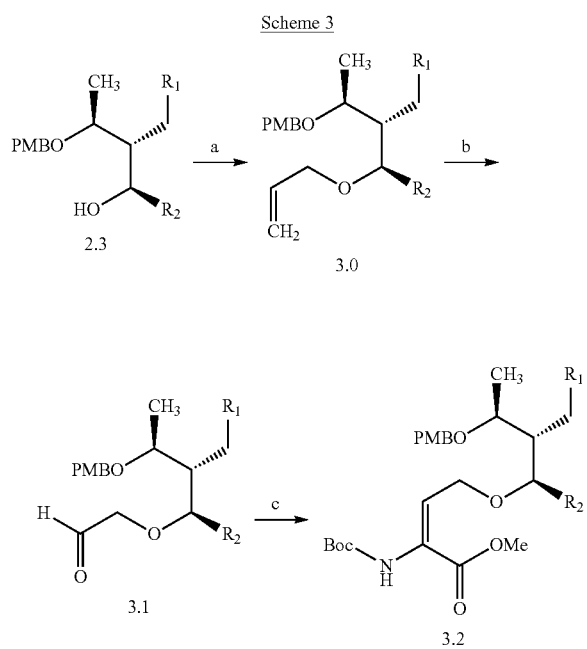

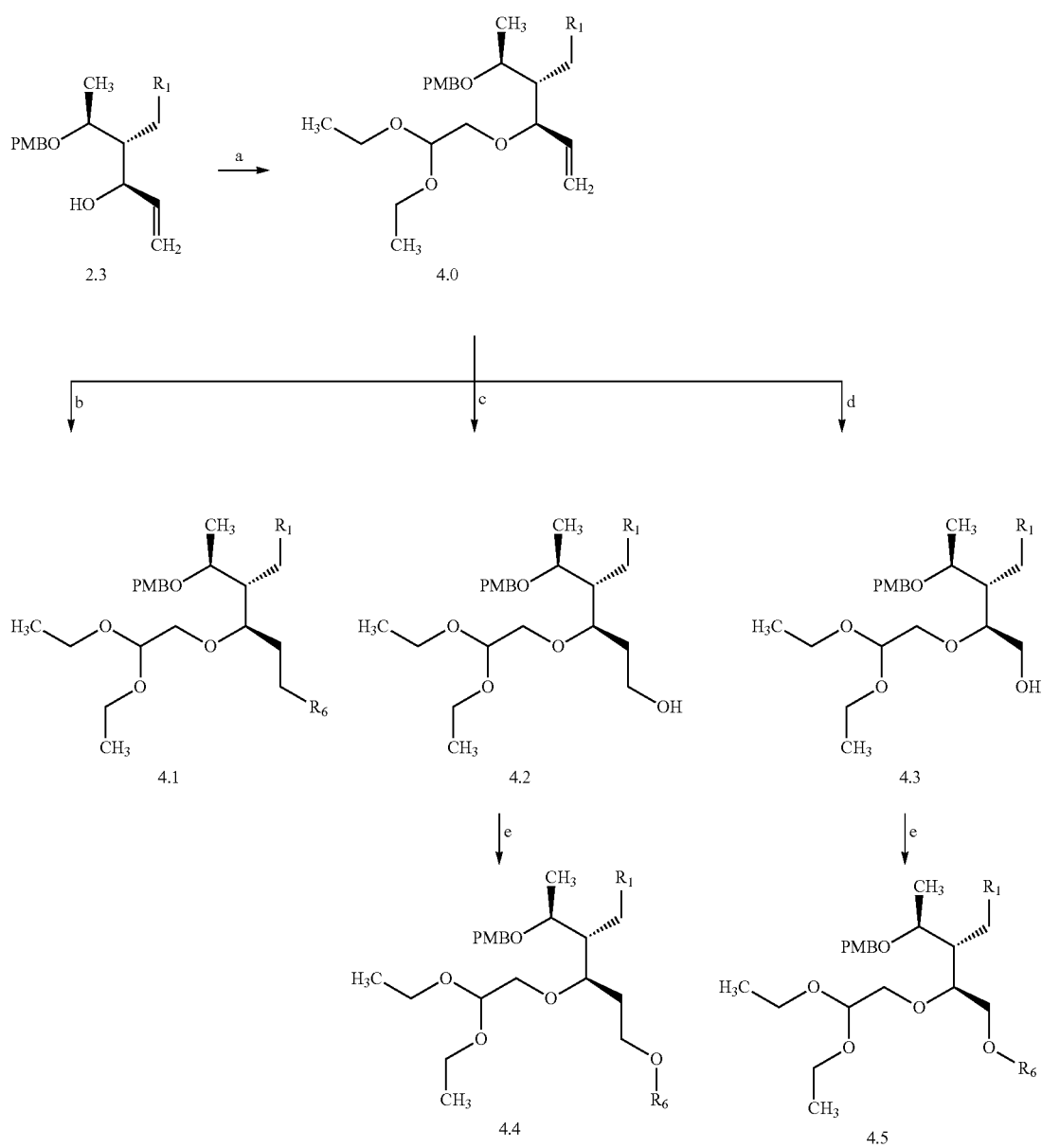

Scheme 4

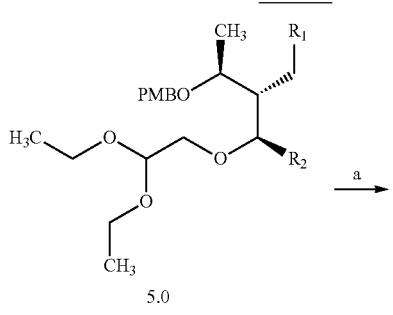

Scheme 5

Compounds of Formula 5.2, where $R_1$ and $R_2$ are as originally defined, can be prepared according to the methods outlined in Scheme 5, steps a-b. As shown in a, compounds of Formula 5.0, where $R_1$ and $R_2$ are as originally defined, can be treated with a Lewis acid such as lithium tetrafluoroborate ($LiBF_4$) in a polar, aprotic solvent such as $CH_3CN$ at a temperature of about 60° C. to obtain aldehydes of Formula 5.1, where $R_1$ and $R_2$ are as originally defined. Compounds of Formula 5.2, where $R_1$ and $R_2$ are as previously defined, can be prepared from aldehydes of Formula 5.1, where $R_1$ and $R_2$ are as previously defined, by treating with an glide precursor such as methyl 2-((tert-butoxycarbonyl)amino)-2-(dimethoxyphosphoryl)acetate and a base such as 1,8-diazabicyclo[5.4.0]undec-7-ene (DBU) in a solvent such as DCM to afford compounds of Formula 5.2, where $R_1$ and $R_2$ are as previously defined, as shown in b.

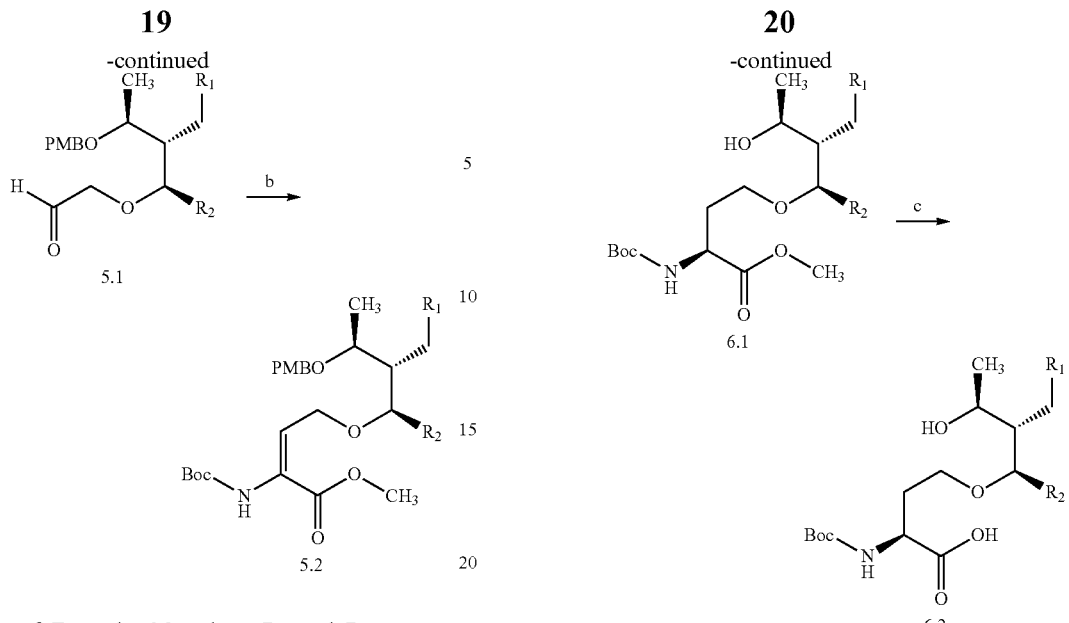

Compounds of Formula 6.2, where $R_1$ and $R_2$ are as originally defined, but $R_2$ is not alkenyl, can be prepared according to the methods outlined in Scheme 6, steps a-c. Compounds of Formula 5.2, where $R_1$ and $R_2$ are as originally defined, can be treated with a chiral catalyst such as (+)-1,2-bis((2S,5S)-2,5-diethylphospholano)benzene(1,5-cyclooctadiene)rhodium(I) trifluoromethanesulfonate in the presence of $H_2$, to afford compounds of Formula 6.0, where $R_1$ and $R_2$ are as originally defined, but $R_2$ is not alkenyl, as shown in a. Compounds of Formula 6.1, where $R_1$ and $R_2$ are as originally defined, can be obtained from compounds of Formula 6.0, where $R_1$ and $R_2$ are as previously defined, by treating with an oxidant such as 2,3-dichloro-5,6-dicyano-p-benzoquinone (DDQ) in a solvent mixture such as DCM and water, as shown in b. Treating compounds of Formula 6.1, where $R_1$ and $R_2$ are as previously defined, with a hydroxide base such as lithium hydroxide (LiOH) in a solvent mixture such as THF and water, as depicted in c, provides compounds of Formula 6.2, where $R_1$ and $R_2$ are as previously defined.

Compounds of Formula 7.0, where $R_1$ and $R_2$ are as originally defined, can be prepared according to the method outlined in Scheme 7, step a. Compounds of Formula 7.0, where $R_1$ and $R_2$ are as previously defined, can be obtained by the addition of a solution of compounds of Formula 6.2, where $R_1$ and $R_2$ are as originally defined, in a halogenated solvent such as DCM to a mixture of a base, such as 4-dimethylaminopyridine (DMAP), and a mixed anhydride, such as 2-methyl-6-nitrobenzoic anhydride (MNBA), in an aprotic solvent such as DCM over a period of 4-12 hours (h), as shown in a.

Scheme 6

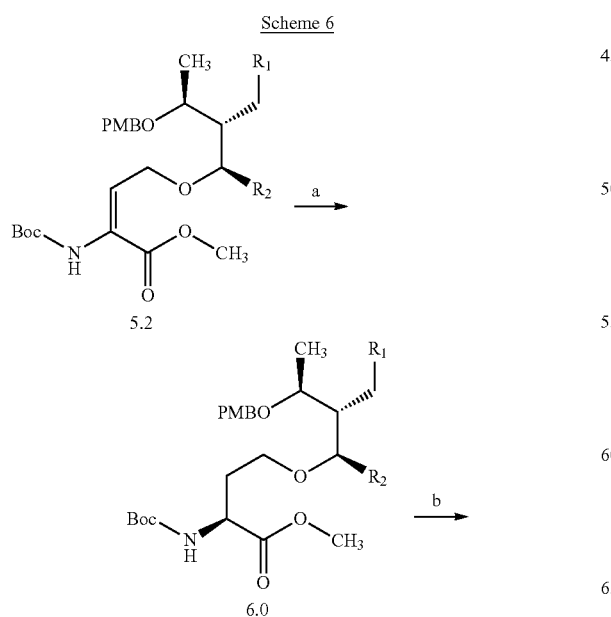

Scheme 7

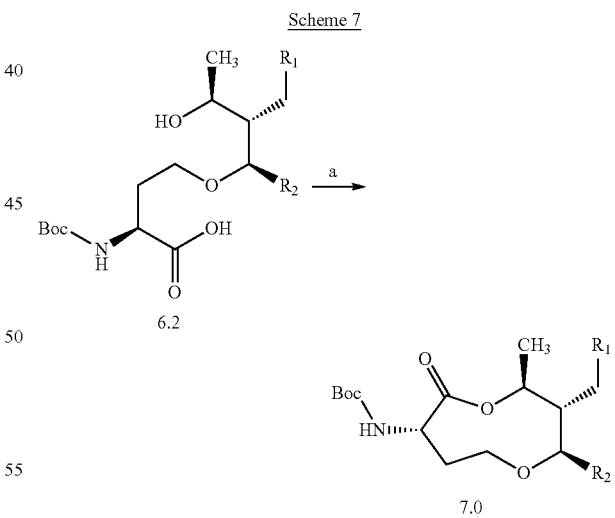

Compounds of Formula 8.2, where $R_1$ is as originally defined and $R_6$ is acyl, can be prepared according to the method outlined in Scheme 8, steps a-b. Compounds of Formula 8.1, where $R_1$ is as originally defined, can be prepared from compounds of Formula 8.0, where $R_1$ is as originally defined, by treating with a catalyst such as Pd/C in the presence of $H_2$ in a solvent such as EtOAc as shown in a. Alcohols of Formula 8.1, where $R_1$ is as previously defined, can be acylated with an acylating agent such as isobutryl chloride in the presence of a base such as triethylamine (NEt₃) and a catalyst such as DMAP in a halogenated solvent such as DCM, as depicted in b, to afford compounds of Formula 8.2, where $R_1$ and $R_6$ are as previously defined.

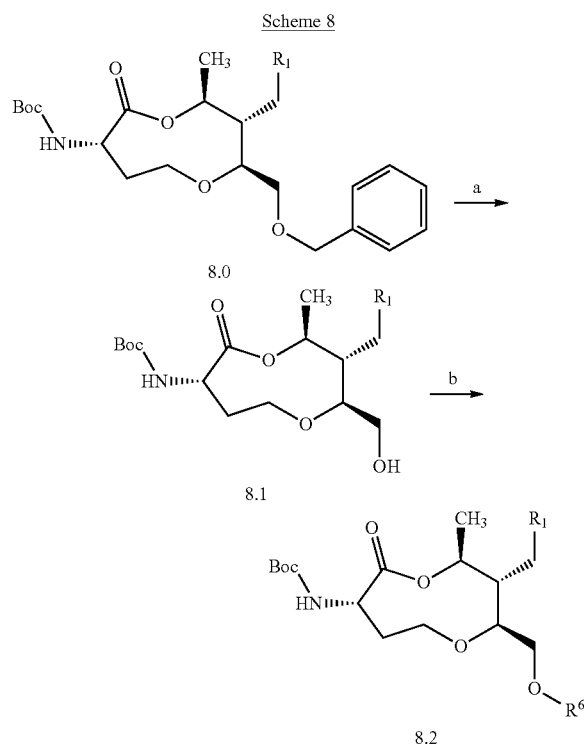

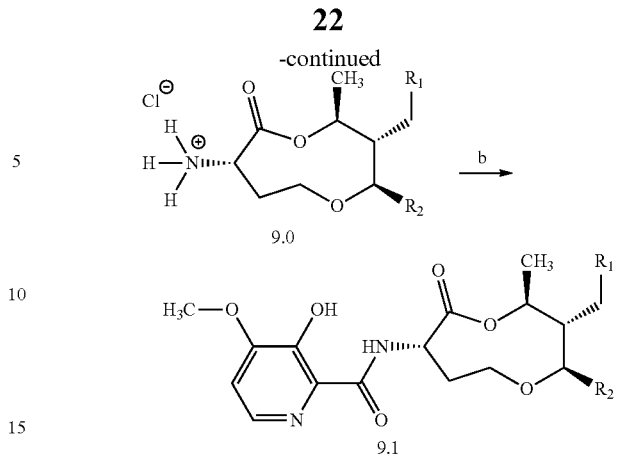

Compounds of Formula 9.1, where $R_1$ and $R_2$ are as originally defined, can be prepared through the methods shown in Scheme 9, steps a-b. Compounds of Formula 7.1, where $R_1$ and $R_2$ are as originally defined, can be treated with an acid such as a 4N solution of hydrogen chloride (HCl) in dioxane in a halogenated solvent such as DCM to afford compounds of Formula 9.0, where $R_1$ and $R_2$ are as originally defined, as depicted in a. The resulting hydrochloride salt may be neutralized prior to use to give the free amine or neutralized in situ in step b. Compounds of Formula 9.1, where $R_1$ and $R_2$ are as originally defined, can be prepared from compounds of Formula 9.0, where $R_1$ and $R_2$ are as defined above, by treating with 3-hydroxy-4-methoxypicolinic acid in the presence of a base, such as diisopropylethylamine, and a peptide coupling reagent, such as benzotriazol-1-yl-oxytripyrrolidinophosphonium hexafluorophosphate (PyBOP) or O-(7-azabenzotriazol-1-yl)-N,N,N',N'-tetramethyluronium hexafluorophosphate (HATU), in an halogenated solvent such as DCM, as shown in b.

Compounds of Formula 10.0, where $R_1$, $R_2$, and $R_4$ are as originally defined, can be prepared according to the method outlined in Scheme 10. Compounds of Formula 10.0, where $R_1$, $R_2$, and $R_4$ are as defined above, can be prepared from compounds of Formula 9.1, where $R_1$ and $R_2$ are as originally defined, by treatment with the appropriate alkyl halide with or without a reagent such as sodium iodide (NaI) and an alkali carbonate base such as sodium carbonate (Na₂CO₃) or potassium carbonate (K₂CO₃) in a solvent such as acetone or by treatment with an acyl halide in the presence of an amine base, such as pyridine, TEA, DMAP, or mixtures thereof in an aprotic solvent such as DCM, as shown in a.

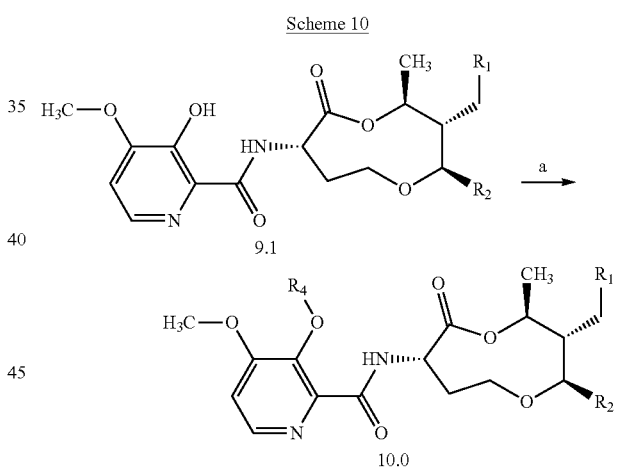

EXAMPLES

Example 1, Step 1: Preparation of (S)-methyl 2-((S)-1-hydroxyethyl)-5-methylhex-4-enoate

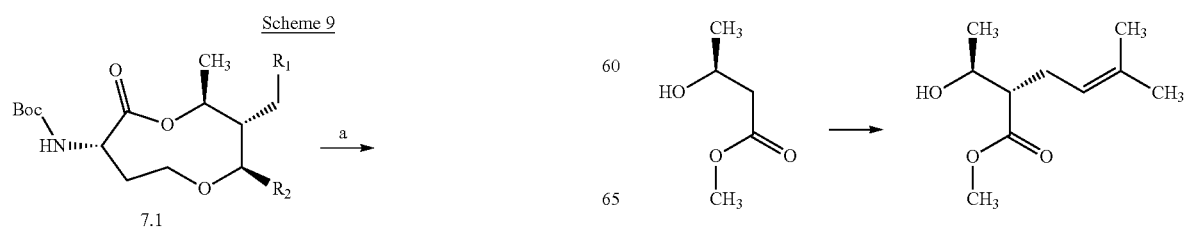

To a solution of diisopropylamine (19.9 milliliters (mL), 142 millimoles (mmol)) in anhydrous THF (99 mL) at −50° C. (deficient dry ice/acetone bath) was added n-butyllithium (n-BuLi; 54.3 mL, 130 mmol, 2.5 M in hexanes). This solution was removed from the cold bath for 15 minutes (min), then re-cooled to −50° C. To the LDA was added a solution of (S)-methyl 3-hydroxybutanoate (6.64 mL, 59.3 mmol) in THF (20.0 mL) dropwise over 15 min using a cannula. This solution was allowed to warm to −30° C. over 30 min, stirred at −30° C. for 1 hour (h), and recooled to −78° C. To the enolate was added a solution of 1-bromo-3-methylbut-2-ene (13.7 mL, 119 mmol) in anhydrous 1,2-dimethoxyethane (20.0 mL, 193 mmol) dropwise over 15 min. The cold bath was at −60° C. after 1 h at which time the reaction flask was removed from the bath and the mixture stirred without cooling for 1.5 h. The reaction mixture was quenched by the addition of saturated (sat.) aqueous (aq.) ammonium chloride (NH$_4$Cl; 50 mL), diluted with EtOAc (50 mL), and the phases were separated. The aqueous phase was further extracted with EtOAc (2×50 mL) and the combined organic extracts were washed with sat. aq. sodium chloride (NaCl, brine; 50 mL), dried over sodium sulfate (Na$_2$SO$_4$), filtered, and concentrated to dryness. The crude residue was purified by flash column chromatography (silica gel (SiO$_2$), 040% EtOAc in hexanes) to afford the title compound (9.5 g, 86%) as a slightly yellow oil: IR (thin film) 3452, 2971, 2929, 1730, 1437, 1198, 1160 cm$^{-1}$; $^1$H NMR (400 MHz, CDCl$_3$) δ 5.11-5.01 (m, 1H), 3.92 (p, J=6.3 Hz, 1H), 3.70 (s, 3H), 2.78 (s, 1H), 2.46-2.28 (m, 3H), 1.69 (d, J=1.4 Hz, 3H), 1.62 (s, 3H), 1.23 (d, J=6.4 Hz, 3H); $^{13}$C NMR (101 MHz, CDCl$_3$) δ 175.54, 134.14, 120.30, 67.78, 52.72, 51.52, 27.90, 25.73, 21.46, 17.64.

Example 1, Step 2: Preparation of (S)-methyl 2-((S)-1-hydroxyethyl)-5-methylhexanoate

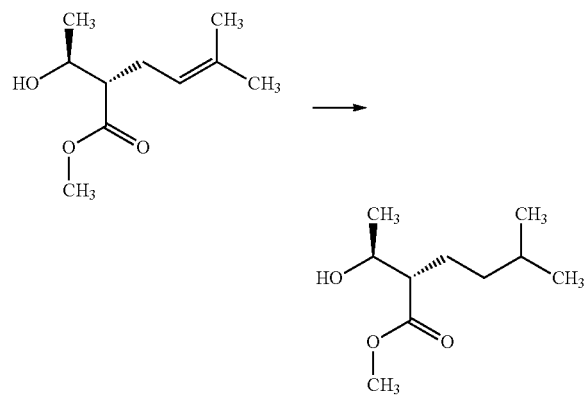

To a well stirred solution of (S)-methyl 2-((S)-1-hydroxyethyl)-5-methylhex-4-enoate (9.5 g, 51.0 mmol) in MeOH (51 mL) was added 10% Pd/C (0.543 g, 5.10 mmol). The reaction mixture was put under an H$_2$ atmosphere (balloon) and stirred at room temperature for 20 h. The mixture was filtered through a plug of Celite® and the plug was washed with MeOH (20 mL). The filtrate and washes were combined, the solvent was removed under reduced pressure, and the residue was dissolved in DCM (50 mL). The solution was passed through a phase separator to remove residual water (H$_2$O), and the solvent was removed under reduced pressure to afford the title compound (9.45 g, 98%) as a slightly yellow oil: IR (thin film) 3451, 2954, 2871, 1736, 1719, 1169 cm$^{-1}$; $^1$H NMR (400 MHz, CDCl$_3$) δ 3.91 (p, J=6.4 Hz, 1H), 3.72 (s, 3H), 2.77 (s, 1H), 2.36 (ddd, J=9.2, 6.3, 5.0 Hz, 1H), 1.72-1.45 (m, 3H), 1.28-1.05 (m, 5H), 0.88 (dd, J=6.6, 3.2 Hz, 6H); $^{13}$C NMR (75 MHz, CDCl$_3$) δ 176.13, 68.55, 53.29, 51.67, 36.55, 28.16, 27.37, 22.74, 22.44, 21.68.

Example 1, Step 3: Preparation of (S)-methyl 2-((S)-1-((4-methoxybenzyl)oxy)ethyl)-5-methyl-hexanoate

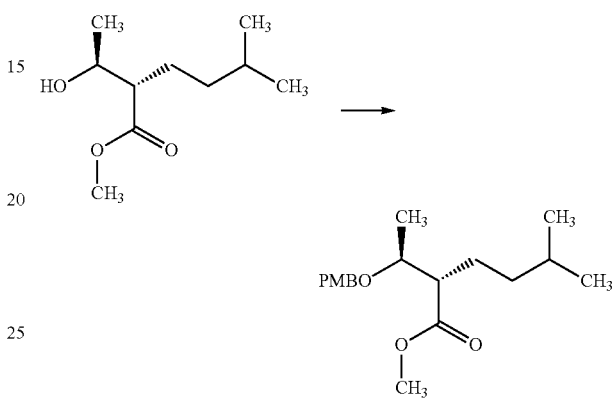

To a solution of (S)-methyl 2-((S)-1-hydroxyethyl)-5-methylhexanoate (5.00 g, 26.6 mmol) and CSA (0.617 g, 2.66 mmol) in DCM (53.1 mL) was added 4-methoxybenzyl 2,2,2-trichloroacetimidate (8.27 mL, 39.8 mmol) at 0° C. The reaction mixture was removed from the cold bath and stirred at room temperature for 17 h. Hexane (50 mL) was added to the reaction mixture and the precipitate was removed by filtration. The solids were washed with hexanes (2×10 mL), and Celite® was added to the combined filtrate and washes and the solvent was removed under reduced pressure. The resulting adsorbed material was directly loaded onto a column and purified using flash column chromatography (SiO$_2$, 1→35% EtOAc in hexanes) to afford the title compound (6.3 g, 77%) as a colorless oil: $^1$H NMR (400 MHz, CDCl$_3$) δ 7.24-7.16 (m, 2H), 6.89-6.79 (m, 2H), 4.49 (d, J=11.2 Hz, 1H), 4.33 (d, J=11.1 Hz, 1H), 3.75 (s, 3H), 3.74-3.62 (m, 4H), 2.49 (ddd, J=10.7, 8.2, 4.0 Hz, 1H), 1.62-1.40 (m, 3H), 1.23-1.16 (m, 3H), 1.16-1.03 (m, 2H), 0.87 (d, J=3.9 Hz, 3H), 0.85 (d, J=3.9 Hz, 3H); $^{13}$C NMR (101 MHz, CDCl$_3$) δ 175.03, 159.10, 130.63, 129.14, 113.62, 76.16, 70.71, 55.11, 52.64, 51.25, 36.58, 27.97, 26.00, 22.69, 22.17, 17.08; ESIMS m/z 331 ([M+Na]$^+$).

Example 2, Steps 1 and 2: Preparation of (3S,4R)-4-((S)-1-((4-methoxy-benzyl)oxy)ethyl)-7-methyl-oct-1-en-3-ol and (3R,4R)-4-((S)-1-(4-methoxybenzyl)oxy)ethyl)-7-methyloct-1-en-3-ol

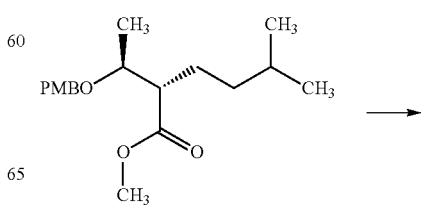

-continued

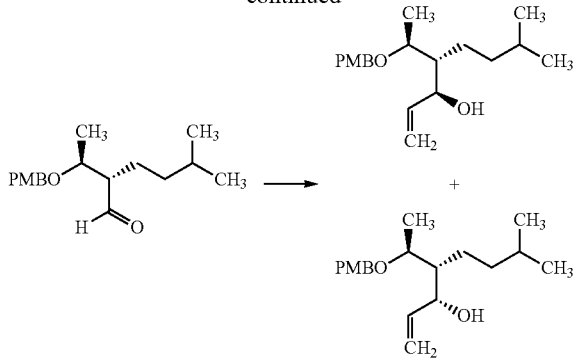

Step 1

To a solution of (S)-methyl 2-((S)-1-((4-methoxybenzyl)oxy)ethyl)-5-methylhexanoate (6.00 g, 19.5 mmol) and chlorobis(cyclooctene)-iridium(I) dimer (0.349 g, 0.389 mmol) in dry DCM (19.5 mL) was slowly added $Et_2SiH_2$ (3.76 mL, 29.2 mmol) at 0° C. The flask was removed from the cold bath and the reaction mixture was stirred at room temperature for 20 h under nitrogen ($N_2$). The reaction mixture was transferred via cannula to an ice-cooled mixture of diethyl ether ($Et_2O$; 60 mL) and 2 Normal (N) aq. hydrogen chloride (HCl; 20 mL) over a 15 min period. The mixture was removed from the cold bath and stirred at room temperature for 30 min. The phases were separated and the aq. phase was further extracted with $Et_2O$ (2×50 mL). The organics were combined, washed with sat. aq. sodium bicarbonate ($NaHCO_3$; 25 mL) and brine (25 mL), dried over $Na_2SO_4$, filtered, and the filtrate treated with Celite®. The solvent was removed under reduced pressure and the resulting adsorbed material was directly loaded onto a column and purified using flash column chromatography ($SiO_2$, 0→75% EtOAc in hexanes) to afford the intermediate aldehyde, (S)-2-((S)-1-((4-methoxybenzyl)oxy)ethyl)-5-methylhexanal.

Step 2

The intermediate aldehyde was dissolved in THF (30 mL) and the mixture was cooled to −78° C. and treated dropwise with vinylmagnesium bromide (29.2 mL, 29.2 mmol, 1M in THF). The resulting solution was stirred at −78° C. for 30 min, removed from the cold bath, warmed to and stirred at room temperature for 30 min, and then quenched by the addition of sat. aq. $NH_4Cl$ (30 mL). The phases were separated and the aq. phase was further extracted with $Et_2O$ (3×50 mL). The combined organics were dried over $Na_2SO_4$, filtered, and concentrated to dryness. The residue was dissolved in DCM (20 mL) and the resulting solution was treated with Celite®. The solvent was removed under reduced pressure and the resulting adsorbed material was directly loaded onto a column and purified using flash column chromatography ($SiO_2$, 0→15% acetone in hexanes) to afford the individual diastereomers as colorless oils:

(3S,4R)-4-((S)-1-((4-methoxybenzyl)oxy)ethyl)-7-methyloct-1-en-3-ol (2.35 g, 39%): $^1$H NMR (400 MHz, $CDCl_3$) δ 7.27-7.19 (m, 2H), 6.91-6.82 (m, 2H), 5.84 (ddd, J=17.2, 10.6, 4.7 Hz, 1H), 5.29 (apparent (app) dt, J=17.2, 1.9 Hz, 1H), 5.16 (app dt, J=10.6, 1.9 Hz, 1H), 4.58 (d, J=11.0 Hz, 1H), 4.53-4.45 (m, 1H), 4.27 (d, J=10.9 Hz, 1H), 3.83 (d, J=4.3 Hz, 1H), 3.79 (s, 3H), 3.76-3.65 (m, 1H), 1.52-1.26 (m, 7H), 1.20-1.06 (m, 2H), 0.85 (app dd, J=6.6, 2.2 Hz, 6H); $^{13}$C NMR (101 MHz, $CDCl_3$) δ 159.33, 139.16, 130.02, 129.54, 114.61, 113.88, 76.55, 72.08, 70.65, 55.26, 49.31, 37.35, 28.25, 23.51, 22.63, 22.52, 17.71; ESIMS m/z 329 ([M+Na]$^+$).

(3R,4R)-4-((S)-1-((4-methoxybenzyl)oxy)ethyl)-7-methyloct-1-en-3-ol (1.48 g, 25%): $^1$H NMR (400 MHz, $CDCl_3$) δ 7.30-7.22 (m, 2H), 6.91-6.83 (m, 2H), 5.89 (ddd, J=17.1, 10.3, 6.7 Hz, 1H), 5.24 (ddd, J=17.2, 1.8, 1.2 Hz, 1H), 5.12 (ddd, J=10.4, 1.8, 1.1 Hz, 1H), 4.58 (d, J=11.1 Hz, 1H), 4.35 (d, J=11.1 Hz, 1H), 4.22-4.13 (m, 1H), 3.80 (s, 3H), 3.70 (p, J=6.3 Hz, 1H), 3.66 (d, J=3.2 Hz, 1H), 1.56 (tt, J=6.8, 5.2 Hz, 1H), 1.49-1.24 (m, 6H), 1.19-1.08 (m, 2H), 0.84 (dd, J=6.7, 2.0 Hz, 6H); $^{13}$C NMR (101 MHz, $CDCl_3$) δ 159.24, 140.20, 130.22, 129.41, 115.17, 113.87, 78.10, 75.83, 70.43, 55.28, 48.98, 36.07, 28.53, 26.08, 22.52, 17.93; ESIMS m/z 329 ([M+Na]$^+$).

Example 2, Steps 3 and 4: Preparation of (2R,3R,4S)-3-benzyl-4-((4-methoxybenzyl)oxy)-1-phenylpentan-2-ol

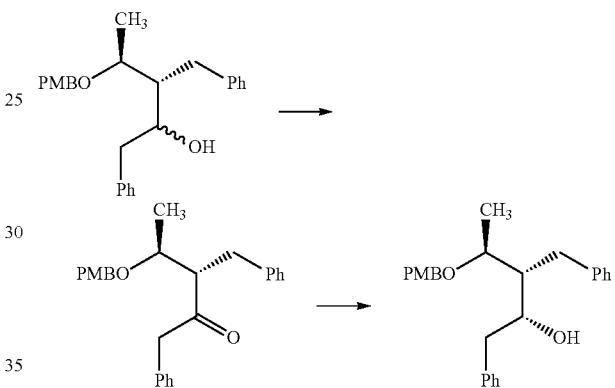

Step 3

To a solution of (3R,4S)-3-benzyl-4-((4-methoxybenzyl)oxy)-1-phenylpentan-2-ol (3.1 g, 7.94 mmol) in DCM (31.8 mL) was added $NaHCO_3$ (0.767 g, 9.13 mmol) and the reaction was cooled to 0° C. and treated with DMP (3.87 g, 9.13 mmol). The flask was removed from the cold bath, allowed to warm to room temperature, and stirred for 3 h. The reaction mixture was diluted with DCM and quenched with a half sat. aq. solution of sodium thiosulfate ($Na_2S_2O_3$). The biphasic mixture was stirred for 5 min, during which time the layers became clear. The aqueous phase was extracted DCM (2×) and then the combined organic phases were washed with sat. aq. $NaHCO_3$ and dried by passing through a phase separator cartridge. The solvent was removed and the crude oil was purified by flash column chromatography ($SiO_2$, 1→20% acetone in hexanes) to afford the intermediate ketone, (3S,4S)-3-benzyl-4-((4-methoxybenzyl)oxy)-1-phenylpentan-2-one, (2.28 g, 74%) as a colorless oil: $^1$H NMR (400 MHz, $CDCl_3$) δ 7.29-7.22 (m, 3H), 7.22-7.19 (m, 1H), 7.17 (ddd, J=5.5, 2.5, 1.1 Hz, 4H), 7.10-7.05 (m, 2H), 6.89-6.81 (m, 2H), 6.74-6.70 (m, 2H), 4.48 (d, J=10.8 Hz, 1H), 4.26 (d, J=10.8 Hz, 1H), 3.80 (s, 3H), 3.85-3.73 (m, 1H), 3.53 (d, J=17.2 Hz, 1H), 3.14 (d, J=17.1 Hz, 1H), 3.09 (ddd, J=10.8, 8.5, 4.7 Hz, 1H), 2.81 (dd, J=13.0, 10.7 Hz, 1H), 2.75 (dd, J=13.1, 4.8 Hz, 1H), 1.30 (d, J=6.1 Hz, 3H); $^{13}$C NMR (101 MHz, $CDCl_3$) δ 210.45, 159.19, 139.07, 133.70, 130.43, 129.76, 129.45, 129.02, 128.54, 128.18, 126.55, 126.33, 113.75, 77.21, 71.10, 59.67, 55.29, 53.08, 34.91, 17.51; ESIMS m/z 411 ([M+Na]$^+$).

Step 4

To a solution of (3S,4S)-3-benzyl-4-((4-methoxybenzyl)oxy)-1-phenylpentan-2-one (1.5 g, 3.86 mmol) in toluene (25.7 mL) was added (S)-1-methyl-3,3-diphenylhexahydro-pyrrolo-[1,2-c][1,3,2]oxazaborole (0.386 mL, 0.386 mmol) followed by the slow addition of a solution of BH$_3$-DMS (0.403 mL, 4.25 mmol) in toluene (5 mL) at room temperature. The reaction mixture was stirred for 3 h, quenched with MeOH (3.12 mL, 77 mmol), and partitioned between EtOAc and water. The phases were separated and the aqueous phase was extracted with EtOAc (2×). The combined organic phases were washed with brine, dried over Na$_2$SO$_4$, filtered, concentrated, and the crude oil purified by flash column chromatography (SiO$_2$, 1→20% acetone in hexanes) to afford the title compound (878 mg, 58%) as a colorless oil: $^1$H NMR (400 MHz, CDCl$_3$) δ 7.30-7.24 (m, 6H), 7.23-7.17 (m, 2H), 7.16-7.08 (m, 4H), 6.92-6.86 (m, 2H), 4.58 (d, J=11.3 Hz, 1H), 4.34 (d, J=11.3 Hz, 1H), 4.05-3.91 (m, 1H), 3.81 (s, 3H), 3.76 (qd, J=6.4, 4.0 Hz, 1H), 2.96 (dd, J=13.8, 3.4 Hz, 1H), 2.83 (dd, J=12.3, 5.8 Hz, 1H), 2.81-2.75 (m, 1H), 2.69 (dd, J=13.8, 9.7 Hz, 1H), 2.31 (d, J=4.2 Hz, 1H), 2.04 (tt, J=7.1, 4.3 Hz, 1H), 1.30 (d, J=6.4 Hz, 3H); $^{13}$C NMR (101 MHz, CDCl$_3$) δ 159.15, 141.29, 139.47, 130.82, 129.30, 129.20, 129.17, 128.47, 128.32, 126.25, 125.80, 113.84, 75.10, 73.54, 70.33, 55.31, 50.02, 42.21, 34.15, 18.21; ESIMS m/z 413 ([M+Na]$^+$).

Example 2, Step 5a: Preparation of (2R,3S)-2-benzyl-3-((4-methoxybenzyl)-oxy)butan-1-ol

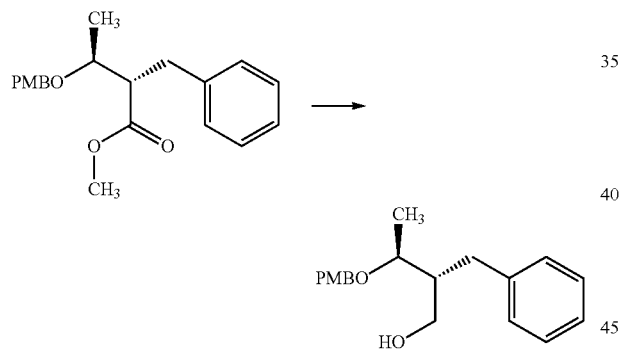

To a solution of (2S,3S)-methyl 2-benzyl-3-((4-methoxybenzyl)oxy)butanoate (1 g, 3.05 mmol) in THF (15.2 mL) at 0° C. was added LAH (3.20 mL, 3.20 mmol, 1 M in THF). The reaction was left to stir at 0° C. for 2 h, then removed from the cold bath and let warm to room temperature for 1 h. The flask was cooled to 0° C. and the mixture was diluted with EtOAc (15 mL) and quenched with a sat. aq. solution of Rochelle's salt (~30 mL). The biphasic mixture was removed from the cold bath and stirred over the weekend, at which point the phases became clear. The phases were separated and the aqueous phase was extracted with EtOAc (3×). The combined organic phases were washed with brine and dried over Na$_2$SO$_4$ and filtered. The solvent was evaporated and the crude oil was purified by flash chromatography (SiO$_2$, 1→30% acetone in hexanes) to afford the title compound (788 mg, 86%) as a colorless oil: $^1$H NMR (400 MHz, CDCl$_3$) δ 7.31-7.22 (m, 4H), 7.22-7.17 (m, 1H), 7.16-7.10 (m, 2H), 6.92-6.86 (m, 2H), 4.60 (d, J=11.2 Hz, 1H), 4.31 (d, J=11.2 Hz, 1H), 3.90 (ddd, J=11.3, 3.9, 2.6 Hz, 1H), 3.82 (s, 3H), 3.67 (qd, J=6.1, 4.2 Hz, 1H), 3.51 (ddd, J=11.3, 7.6, 4.9 Hz, 1H), 2.86 (dd, J=7.5, 3.9 Hz, 1H), 2.80 (dd, J=13.7, 6.6 Hz, 1H), 2.73 (dd, J=13.7, 8.4 Hz, 1H), 1.76 (ddtd, J=9.0, 7.0, 4.6, 2.5 Hz, 1H), 1.31 (d, J=6.2 Hz, 3H); $^{13}$C NMR (101 MHz, CDCl$_3$) δ 159.29, 140.56, 130.29, 129.37, 129.17, 128.34, 125.95, 113.90, 77.45, 70.69, 62.37, 55.30, 47.79, 35.15, 17.68; ESIMS m/z 323 ([M+Na]$^+$).

Example 2, Step 5b: Preparation of (2R,3S)-2-isopentylbutane-1,3-diol

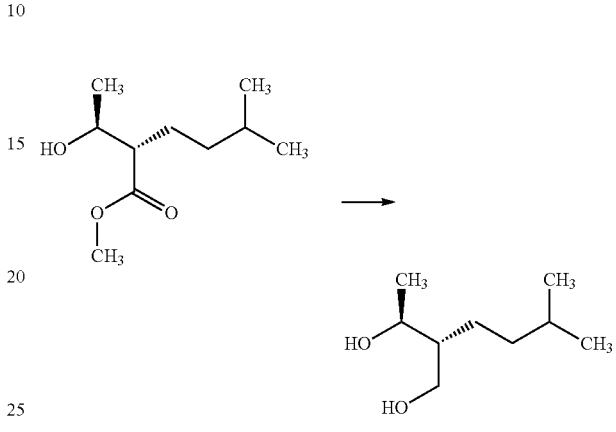

To a solution of (S)-methyl 2-((S)-1-hydroxyethyl)-5-methylhexanoate (1 g, 5.31 mmol) in THF (21.3 mL) at 0° C. was added LAH (5.84 mL, 5.84 mmol, 1 M in THF). The reaction mixture was left to stir at 0° C. for 10 min, removed from the cold bath, and allowed to warm to room temperature. After stirring for 3 h, H$_2$O (0.222 mL), 15% aq. NaOH (0.222 mL), H$_2$O (0.666 mL), and then Et$_2$O (25 mL) were sequentially added to the reaction flask. The mixture was stirred vigorously at room temperature for 1 h, MgSO$_4$ was added, and the suspension was filtered through a pad of Celite®. The pad was washed with Et$_2$O (3×20 mL) and the filtrate and washings were combined and concentrated under reduced pressure to afford the title compound (825 mg, 97%) as a colorless oil: $^1$H NMR (400 MHz, CDCl$_3$) δ 3.96-3.82 (m, 2H), 3.71-3.61 (m, 1H), 2.96 (t, J=5.2 Hz, 1H), 2.82 (d, J=4.1 Hz, 1H), 1.60-1.08 (m, 9H), 0.89 (app dd, J=6.6, 3.8 Hz, 6H); $^{13}$C NMR (101 MHz, CDCl$_3$) δ 72.19, 64.67, 46.51, 36.42, 28.31, 26.26, 22.72, 22.37, 22.16.

Example 3, Step 1a: Preparation of ((2R,3S)-2-(allyloxy)-3-((S)-1-((4-methoxybenzyl)oxy)ethyl)butane-1,4-diyl)dibenzene

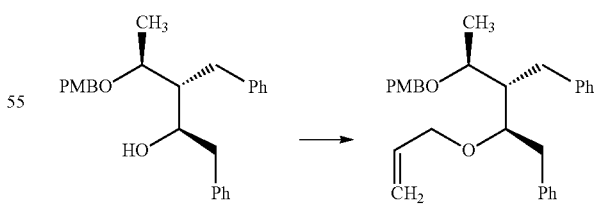

To a solution of (2R,3R,4S)-3-benzyl-4-((4-methoxybenzyl)oxy)-1-phenylpentan-2-ol (878 mg, 2.25 mmol) in DMF (9 mL) at 0° C. was added a 60% dispersion of NaH (225 mg, 5.62 mmol) in mineral oil. The reaction mixture was stirred at 0° C. for 5 min, treated with 3-bromoprop-1-ene (535 microliters (μL), 6.18 mmol), removed from the cold bath, and then heated to 50° C. The reaction mixture was maintained at 50° C. for 5 h, cooled to room temperature, diluted with EtOAc, and quenched with sat. aq. NH₄Cl. The phases were separated and the aqueous phase was extracted with EtOAc (2×). The combined organic phases were washed with brine (4×), dried over Na₂SO₄, filtered, and the solvent evaporated. The residual colorless oil was purified by flash chromatography (SiO₂, 1→20% acetone in hexanes) to give the title compound (782 mg, 81%) as a colorless oil: ¹H NMR (400 MHz, CDCl₃) δ 7.29-7.24 (m, 3H), 7.24-7.20 (m, 3H), 7.18 (dt, J=2.9, 1.5 Hz, 1H), 7.17-7.13 (m, 1H), 7.15-7.03 (m, 4H), 6.92-6.84 (m, 2H), 5.74 (ddt, J=17.2, 10.6, 5.4 Hz, 1H), 5.15 (dq, J=17.2, 1.7 Hz, 1H), 5.05 (dq, J=10.4, 1.5 Hz, 1H), 4.50 (d, J=11.3 Hz, 1H), 4.29 (d, J=11.3 Hz, 1H), 3.87-3.81 (m, 1H), 3.81 (s, 3H), 3.79-3.74 (m, 1H), 3.74-3.69 (m, 2H), 2.97 (dd, J=13.9, 4.4 Hz, 1H), 2.89 (dd, J=13.6, 6.5 Hz, 1H), 2.79 (dd, J=13.5, 7.6 Hz, 1H), 2.76 (dd, J=13.9, 8.8 Hz, 1H), 2.10 (tdd, J=6.6, 5.3, 3.6 Hz, 1H), 1.25 (d, J=6.3 Hz, 3H); ¹³C NMR (101 MHz, CDCl₃) δ 159.00, 141.94, 140.22, 135.34, 131.27, 129.33, 129.18, 128.99, 128.21, 128.09, 125.81, 125.59, 115.96, 113.75, 79.99, 73.77, 70.99, 70.17, 55.31, 48.07, 38.38, 31.83, 17.68; ESIMS m/z 453 ([M+Na]⁺).

Example 3, Step 1b: Preparation of (2S,3R)-3-((allyloxy)methyl)-6-methylheptan-2-ol

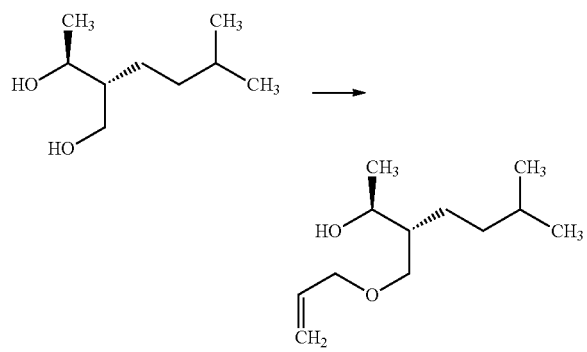

To a suspension of NaH (404 mg, 10.1 mmol, 60% dispersion in mineral oil) in anhydrous THF (20 mL) was added a solution of (2R,3S)-2-isopentylbutane-1,3-diol (810 mg, 5.05 mmol) in THF (9 mL) dropwise at 0° C. The mixture was removed from the cold bath and stirred at room temperature for 30 minutes, recooled to 0° C., and then treated with 3-bromoprop-1-ene (416 μL, 4.81 mmol). After 4 h, DMF (3.2 mL) was added to the reaction and the mixture was maintained at room temperature for 14 h. The reaction mixture was quenched with sat. aq. NH₄Cl (20 mL) and extracted with Et₂O (3×20 mL). The combined organic extracts were washed with brine (15 mL), dried (Na₂SO₄), filtered, and concentrated to dryness. The crude residue was purified by flash chromatography (SiO₂, 0→25% EtOAc in hexanes) to give the title compound (425 mg, 44%) as a colorless oil: ¹H NMR (400 MHz, CDCl₃) δ 5.89 (ddt, J=17.3, 10.4, 5.6 Hz, 1H), 5.27 (dq, J=17.3, 1.6 Hz, 1H), 5.19 (dq, J=10.4, 1.4 Hz, 1H), 3.98 (ddt, J=5.8, 3.0, 1.4 Hz, 2H), 3.86-3.77 (m, 1H), 3.69 (dd, J=9.4, 3.5 Hz, 1H), 3.47 (dd, J=9.4, 6.6 Hz, 1H), 3.32-3.26 (m, 1H), 1.57-1.37 (m, 3H), 1.34-1.14 (m, 6H), 0.88 (app dd, J=6.6, 3.7 Hz, 6H); ¹³C NMR (101 MHz, CDCl₃) δ 134.31, 117.18, 72.46, 72.29, 70.99, 44.98, 36.47, 28.32, 26.43, 22.73, 22.39, 21.48.

Example 3, Step 2: Preparation of 2-((2R,3S,4S)-3-benzyl-4-((4-methoxybenzyl)-oxy)-1-phenylpentan-2-yl)oxy)acetaldehyde

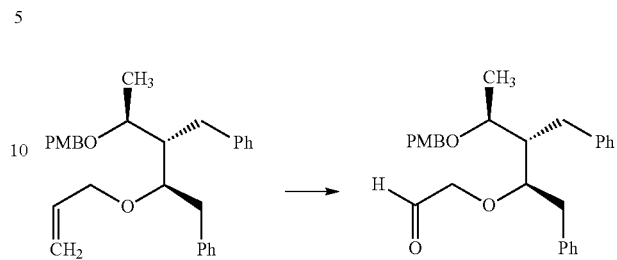

To a solution of ((2R,3S)-2-(allyloxy)-3-((S)-1-((4-methoxybenzyl)oxy)ethyl)butane-1,4-diyl)dibenzene (772 mg, 1.79 mmol) in DCM (16.3 mL) and MeOH (1.63 mL), was added NaHCO₃ (30.1 mg, 0.359 mmol) and Sudan III (10 μL, 1.79 mmol, 10% solution in DCM). The flask was connected to an ozonator and cooled to −78° C. and ozone was bubbled into the flask until the color turned from red to colorless (~10 min). The introduction of ozone was stopped and O₂ was bubbled through the reaction mixture to purge any remaining ozone for (~5 min). While still at −78° C., Ph₃P (705 mg, 2.69 mmol) was added in one portion and the flask was removed from the cold bath, fitted to a nitrogen balloon, and let warm to room temperature overnight. A scoop of Celite® was added to the mixture, the majority of the solvent was evaporated, and the resulting slurry was purified by flash column chromatography (SiO₂, 1→20% acetone in hexanes) to afford the title compound (730 mg, 94%) as a colorless oil: ¹H NMR (400 MHz, CDCl₃) δ 9.39 (d, J=1.0 Hz, 1H), 7.31-7.19 (m, 6H), 7.21-7.15 (m, 2H), 7.15-7.10 (m, 2H), 7.08 (dd, J=7.6, 1.3 Hz, 2H), 6.91-6.86 (m, 2H), 4.54 (d, J=11.3 Hz, 1H), 4.29 (d, J=11.3 Hz, 1H), 3.81 (d, J=0.6 Hz, 3H), 3.81-3.79 (m, 1H), 3.76 (dt, J=9.4, 3.5 Hz, 1H), 3.73-3.72 (m, 1H), 3.72-3.66 (m, 1H), 3.04 (dd, J=14.0, 3.6 Hz, 1H), 2.93 (dd, J=13.8, 6.3 Hz, 1H), 2.83-2.75 (m, 2H), 2.22-2.04 (m, 1H), 1.25 (d, J=6.4 Hz, 3H); ¹³C NMR (101 MHz, CDCl₃) δ 201.77, 159.09, 141.43, 139.70, 131.00, 129.29, 129.10, 129.07, 128.34, 128.34, 126.19, 125.82, 113.80, 82.70, 75.95, 73.68, 70.28, 55.31, 48.62, 38.45, 32.06, 17.82; ESIMS m/z 455 ([M+Na]⁺).

Example 3, Step 3: Preparation of methyl 4-(((2R,3S,4S)-3-benzyl-4-((4-methoxybenzyl)oxy)-1-phenylpentan-2-yl)oxy)-2-((tert-butoxycarbonyl)amino)but-2-enoate

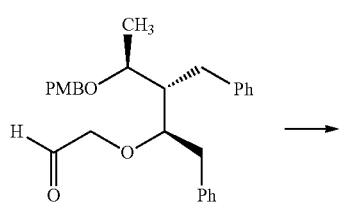

-continued

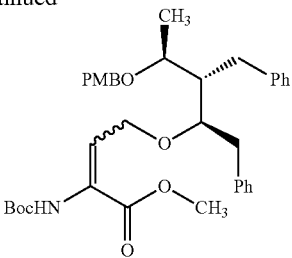

To a solution of 2-(((2R,3S,4S)-3-benzyl-4-((4-methoxybenzyl)oxy)-1-phenylpentan-2-yl)oxy)acetaldehyde (725 mg, 1.68 mmol) in DCM (13.5 mL) was added methyl 2-((tert-butoxycarbonyl)amino)-2-(dimethoxyphosphoryl)acetate (508 mg, 1.71 mmol), and the reaction mixture was cooled to 0° C. and treated with DBU (0.203 mL, 1.76 mmol). The vial was sealed and allowed to slowly warm to room temperature overnight as the ice melted. The reaction mixture was quenched with sat. aq. NH$_4$Cl, the phases were separated, and the aqueous phase was extracted with DCM (3×). The combined organic phase was dried by passing through a phase separator cartridge and the solvent was evaporated. The resulting oil was purified by flash column chromatography (SiO$_2$, 1→15% acetone in hexanes) to afford the title compound (818 mg, 81%) as a colorless oil: $^1$H NMR (400 MHz, CDCl$_3$) major isomer δ 7.30-7.23 (m, 4H), 7.24-7.20 (m, 3H), 7.19-7.16 (m, 1H), 7.12-7.02 (m, 4H), 6.88 (d, J=8.6 Hz, 2H), 6.31 (s, 1H), 6.25 (t, J=5.8 Hz, 1H), 4.51 (d, J=11.3 Hz, 1H), 4.28 (d, J=11.3 Hz, 1H), 4.03 (dd, J=14.9, 5.7 Hz, 1H), 3.89 (dd, J=14.8, 5.9 Hz, 1H), 3.81 (s, 3H), 3.78 (s, 3H), 3.74-3.65 (m, 2H), 2.99 (dd, J=14.0, 4.1 Hz, 1H), 2.87 (dd, J=13.7, 6.4 Hz, 1H), 2.78 (dd, J=13.6, 7.7 Hz, 1H), 2.73 (dd, J=13.9, 8.8 Hz, 1H), 2.15-2.02 (m, 1H), 1.43 (s, 9H), 1.23 (d, J=6.3 Hz, 3H); $^{13}$C NMR (101 MHz, CDCl$_3$) major isomer, (two aromatic signals overlap) δ 164.97, 159.01, 152.95, 141.66, 139.99, 131.17, 129.25, 129.15, 129.02, 128.25, 128.18, 125.88, 125.66, 113.75, 80.86, 80.77, 73.62, 70.18, 66.70, 55.30, 52.46, 48.11, 38.35, 31.94, 28.13, 17.74; ESIMS m/z 626 ([M+Na]$^+$).

Example 4, Step 1: Preparation of 1-((2S,3R)-3-(2,2-diethoxyethoxy)-2-((S)-1-((4-methoxybenzyl)oxy)ethyl)pent-4-en-1-yl)-4-fluorobenzene

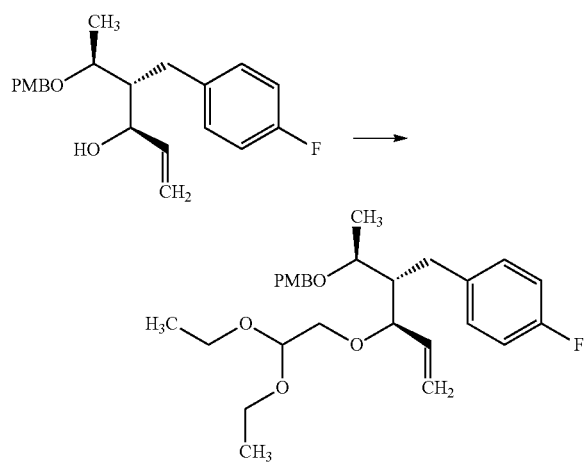

To a solution of (3R,4R,5S)-4-(4-fluorobenzyl)-5-((4-methoxybenzyl)oxy)hex-1-en-3-ol (711 mg, 2.06 mmol) in a mixture of CH$_3$CN (6.88 mL) and DMF (2 mL) was added NaH (140 mg, 3.51 mmol, 60% dispersion in mineral oil) at room temperature. The mixture was stirred for 10 min, treated with 2-bromo-1,1-diethoxyethane (559 μL, 3.72 mmol), and then warmed to and stirred at 55° C. overnight. The reaction mixture was cooled to room temperature, additional 2-bromo-1,1-diethoxyethane (200 μL, 1.33 mmol) was added, and the reaction mixture was again heated to 55° C. and stirred for an additional 2 h. The reaction mixture was quenched with sat. aq. NH$_4$Cl and the phases were separated. The aqueous phase was extracted with EtOAc (3×) and the combined organic phases were washed with brine, dried over Na$_2$SO$_4$, filtered and then the solvent was evaporated. The crude oil was purified by flash column chromatography (SiO$_2$, 1→15% acetone in hexanes) to give the title compound (652 mg, 69%) as a colorless oil: $^1$H NMR (400 MHz, CDCl$_3$) δ 7.23 (d, J=8.6 Hz, 2H), 7.14-7.07 (m, 2H), 6.92 (t, J=8.7 Hz, 2H), 6.87 (d, J=8.6 Hz, 2H), 5.67 (ddd, J=16.7, 10.6, 7.2 Hz, 1H), 5.22-5.10 (m, 2H), 4.60 (dd, J=5.7, 4.9 Hz, 1H), 4.45 (d, J=11.4 Hz, 1H), 4.33 (d, J=11.4 Hz, 1H), 3.80 (s, 3H), 3.77-3.63 (m, 4H), 3.63-3.48 (m, 3H), 3.24 (dd, J=10.2, 5.8 Hz, 1H), 2.70 (dd, J=6.8, 2.7 Hz, 2H), 2.17-2.05 (m, 1H), 1.33-1.12 (m, 9H); $^{19}$F NMR (376 MHz, CDCl$_3$) δ −118.13; ESIMS m/z 483 ([M+Na]$^+$).

Example 4, Step 2: Preparation of 1-((2S,3R)-3-(2,2-diethoxyethoxy)-2-((S)-1-((4-methoxybenzyl)oxy)ethyl)-5-phenylpentyl)-4-fluorobenzene

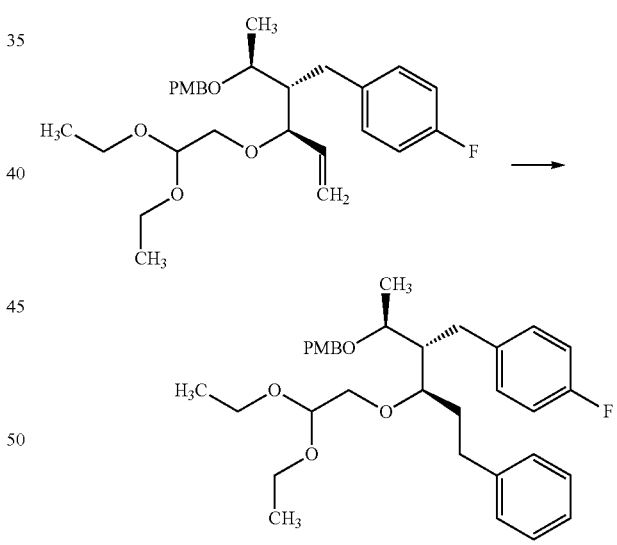

To a solution of 1-((2S,3R)-3-(2,2-diethoxyethoxy)-2-((S)-1-((4-methoxybenzyl)-oxy)ethyl)pent-4-en-1-yl)-4-fluorobenzene (650 mg, 1.41 mmol) in THF (2823 μL) was added 9-BBN (5363 μL, 2.68 mmol, 0.5M in THF). The flask was fitted with a Vigreux column and heated to 50° C. for 2 h. The reaction mixture was quenched with a 3 M aq. solution of K$_3$PO$_4$ (847 μL, 2.54 mmol), and then DMF (2823 μL) and bromobenzene (PhBr; 296 μL, 2.82 mmol) were added, followed by Pd(dppf)Cl$_2$.CH$_2$Cl$_2$ (103 mg, 0.126 mmol). The vial was evacuated under vacuum and backfilled with N$_2$ (3×). The mixture was then heated to and stirred at 65° C. overnight, during which time the reaction turned from homogenous orange/red solution to a nearly black solution. The reaction mixture was cooled to room temperature, diluted with EtOAc, and then treated with sat. aq. NaHCO₃. The phases were separated and the aq. phase was extracted with EtOAc (3×), the combined organic phases were washed with brine, dried over Na₂SO₄, filtered, and the solvent was evaporated. The crude oil was purified by flash column chromatography (SiO₂, 1→15% acetone in hexanes) to afford the title compound (759 mg, 85%): ¹H NMR (400 MHz, CDCl₃) δ 7.23 (t, J=7.8 Hz, 4H), 7.18-7.12 (m, 1H), 7.11-7.02 (m, 4H), 6.92 (t, J=8.8 Hz, 2H), 6.87 (d, J=8.6 Hz, 2H), 4.60 (t, J=5.2 Hz, 1H), 4.49 (d, J=11.4 Hz, 1H), 4.25 (d, J=11.4 Hz, 1H), 3.80 (s, 3H), 3.73 (dt, J=9.3, 7.0 Hz, 2H), 3.62-3.54 (m, 3H), 3.48-3.45 (m, 3H), 2.78 (dd, J=13.7, 6.1 Hz, 1H), 2.73-2.60 (m, 2H), 2.55 (ddd, J=13.7, 9.7, 6.5 Hz, 1H), 2.12-2.01 (m, 1H), 1.93 (dddd, J=14.0, 10.3, 6.5, 4.1 Hz, 1H), 1.78 (dddd, J=13.9, 9.8, 8.3, 5.5 Hz, 1H), 1.24 (t, J=7.0 Hz, 6H), 1.11 (d, J=6.3 Hz, 3H); ¹⁹F NMR (376 MHz, CDCl₃) δ -118.13; ESIMS m/z 561 ([M+Na]⁺).

Example 4, Step 3: Preparation of (3R,4S,5S)-3-(2, 2-diethoxyethoxy)-4-(4-fluorobenzyl)-5-((4-methoxybenzyl)oxy)hexan-1-ol

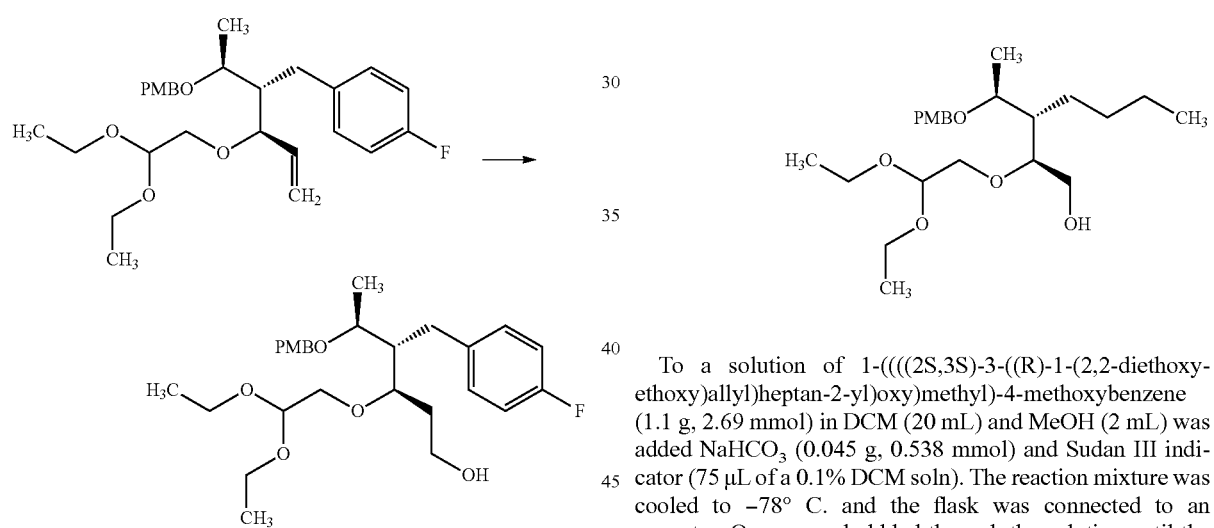

To neat 1-((2S,3R)-3-(2,2-diethoxyethoxy)-2-((S)-1-((4-methoxybenzyl)oxy)ethyl)-pent-4-en-1-yl)-4-fluorobenzene (480 mg, 1.04 mmol) was added 9-BBN (3127 μL, 1.56 mmol, 0.5M in THF). After 4 h at room temperature, the reaction was cooled to 0° C. and treated with 2 M NaOH (2084 μL, 4.17 mmol) followed by H₂O₂ (426 μL, 4.17 mmol, 30 weight %, wt. % in H₂O). After 45 min at 0° C., the cooling bath was removed and the mixture was stirred for 30 min, recooled to 0° C., and quenched with sat. aq. NaHSO₃. The phases were separated and the aqueous phase was extracted with EtOAc (3×) and the combined organic phases were washed with brine, dried over Na₂SO₄, filtered, and the solvent was evaporated. The crude material was purified by flash column chromatography (SiO₂, 1→25% acetone in hexanes) to afford the title compound (448 mg, 90%): ¹H NMR (400 MHz, CDCl₃) δ 7.28-7.18 (m, 2H), 7.02 (dd, J=8.5, 5.6 Hz, 2H), 6.98-6.82 (m, 4H), 4.56 (dd, J=5.9, 4.3 Hz, 1H), 4.51 (d, J=11.4 Hz, 1H), 4.19 (d, J=11.3 Hz, 1H), 3.92 (dt, J=10.1, 3.3 Hz, 1H), 3.82 (s, 1H), 3.76-3.69 (m, 3H), 3.61-3.51 (m, 3H), 3.48-3.36 (m, 2H), 3.12 (td, J=7.6, 4.3 Hz, 1H), 2.84 (dd, J=13.9, 4.3 Hz, 1H), 2.56 (dd, J=13.8, 9.1 Hz, 1H), 2.09-2.00 (m, 1H), 1.90-1.69 (m, 3H), 1.23 (t, J=7.1 Hz, 3H), 1.21 (t, J=6.9 Hz, 3H), 1.16 (d, J=6.3 Hz, 3H); ¹⁹F NMR (376 MHz, CDCl₃) δ -117.92; ESIMS m/z 501 ([M+Na]⁺).

Example 4, Step 4: Preparation of (2S,3S,4S)-2-(2, 2-diethoxyethoxy)-3-(4-fluorobenzyl)-4-((4-methoxybenzyl)oxy)pentan-1-ol

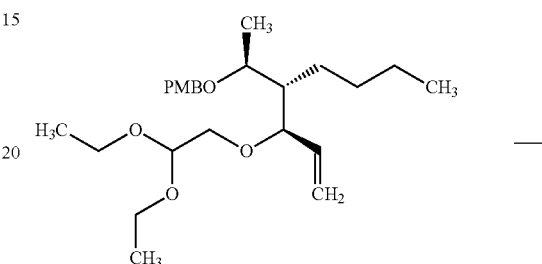

To a solution of 1-(((((2S,3S)-3-((R)-1-(2,2-diethoxyethoxy)allyl)heptan-2-yl)oxy)methyl)-4-methoxybenzene (1.1 g, 2.69 mmol) in DCM (20 mL) and MeOH (2 mL) was added NaHCO₃ (0.045 g, 0.538 mmol) and Sudan III indicator (75 μL of a 0.1% DCM soln). The reaction mixture was cooled to -78° C. and the flask was connected to an ozonator. Ozone was bubbled through the solution until the solution became colorless. Oxygen was then bubbled through the solution for 5 min and the solution was treated with MeOH (3 mL) and NaBH₄ (0.306 g, 8.08 mmol). The flask was removed from the cold bath and allowed to slowly warm to room temperature overnight. The reaction mixture was quenched with water (15 mL) and the phases were separated. The aqueous phase was extracted with DCM (2×) and the combined organic phases were dried over magnesium sulfate (MgSO₄), filtered, and concentrated. The crude, colorless oil was purified by flash column chromatography (SiO₂, 0→35% EtOAc in hexanes) to give the title compound (0.632 g, 57%) as a colorless oil: IR (Thin Film) 3449, 2955, 2931, 2871, 1612, 1513 cm⁻¹; ¹H NMR (400 MHz, CDCl₃) δ 7.26-7.20 (m, 2H), 6.89-6.84 (m, 2H), 4.63-4.58 (m, 1H), 4.51 (d, J=11.3 Hz, 1H), 4.33 (d, J=11.3 Hz, 1H), 3.80 (s, 3H), 3.78-3.51 (m, 8H), 3.49-3.38 (m, 2H), 1.74 (ddd, J=10.7, 6.1, 4.3 Hz, 1H), 1.63 (s, 1H), 1.42-1.33 (m, 2H), 1.32-1.16 (m, 13H), 0.87 (t, J=7.0 Hz, 3H); ESIMS m/z 435 ([M+Na]⁺).

Example 4, Step 5: Preparation of 1-((((2S,3S,4R)-4-(2,2-diethoxyethoxy)-3-(4-fluorobenzyl)-6-methoxyhexan-2-yl)oxy)methyl)-4-methoxybenzene Example 4, Step 6: Preparation of 1-((((2S,3S)-3-((S)-1-(2,2-diethoxyethoxy)-2-phenoxyethyl)heptan-2-yl)oxy)methyl)-4-methoxybenzene

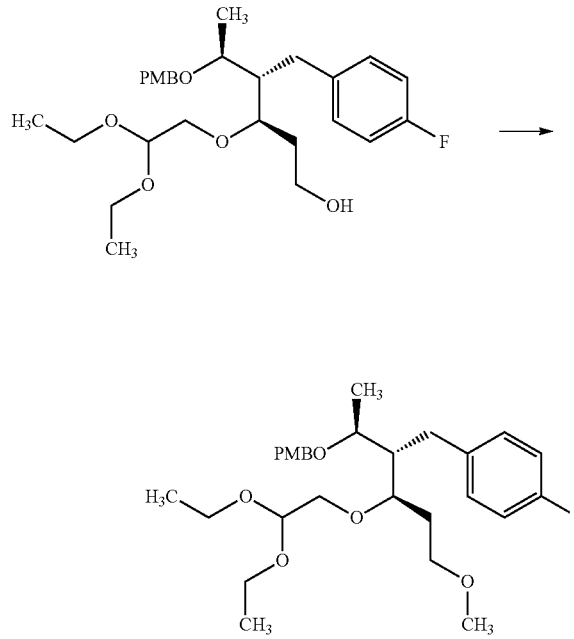

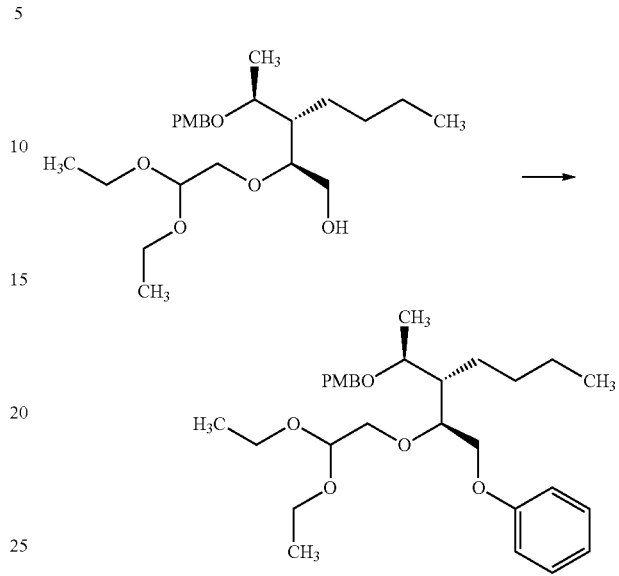

To a solution of 3R,4S,5S)-3-(2,2-diethoxyethoxy)-4-(4-fluorobenzyl)-5-((4-methoxybenzyl)oxy)hexan-1-ol (443 mg, 0.926 mmol) in THF (9256 μL) at 0° C. was added NaH (59.2 mg, 1.48 mmol, 60 wt. % in mineral oil). The reaction mixture was maintained at 0° C. for 15 min, treated with MeI (173 μL, 2.78 mmol), removed from the cold bath, and allowed to slowly warm to room temperature over a 2 h period. Additional NaH (37 mg, 0.93 mmol, 60 wt. % in mineral oil) was added at room temperature and the mixture was stirred overnight. TLC analysis indicated that some of the alcohol starting material (SM) still remained, so additional NaH (37 mg, 0.93 mmol, 60 wt % in mineral oil) and MeI (86 μL, 1.44 mmol) were added and stirring was continued for another 1 h. The reaction mixture was quenched with sat. aq. NH₄Cl and the phases were separated. The aqueous phase was extracted with EtOAc (3×). The combined organic phases were washed with brine, dried over Na₂SO₄, filtered, and the solvent evaporated. The crude oil was purified by flash column chromatography (SiO₂, 1→25% acetone in hexanes) to afford the title compound (283 mg, 62%) as a colorless oil: $^1$H NMR (400 MHz, CDCl₃) δ 7.30-7.23 (m, 2H), 7.05 (dd, J=8.5, 5.6 Hz, 2H), 6.98-6.80 (m, 4H), 4.58 (t, J=5.2 Hz, 1H), 4.50 (d, J=11.4 Hz, 1H), 4.24 (d, J=11.4 Hz, 1H), 3.81 (s, 3H), 3.78-3.62 (m, 3H), 3.61-3.51 (m, 3H), 3.50-3.35 (m, 4H), 3.28 (s, 3H), 2.79 (dd, J=13.8, 5.4 Hz, 1H), 2.64 (dd, J=13.7, 8.2 Hz, 1H), 2.06-1.90 (m, 2H), 1.78-1.59 (m, 1H), 1.23 (t, J=7.0 Hz, 6H), 1.17 (d, J=6.4 Hz, 3H); $^{19}$F NMR (376 MHz, CDCl₃) δ −118.16; ESIMS m/z 515 ([M+Na]⁺).

To a solution of (2S,3S)-2-(2,2-diethoxyethoxy)-3-((S)-1-((4-methoxybenzyl)-oxy)ethyl)heptan-1-ol (1.00 g, 2.42 mmol) in toluene (15 mL) were added bis(acetato-O)triphenylbismuth(V) (2.98 g, 5.33 mmol), N-cyclohexyl-N-methylcyclohexanamine (1.14 mL, 5.33 mmol), and diacetoxycopper (0.110 g, 0.606 mmol) at room temperature. The reaction mixture was heated to and stirred at 50° C. for 6 h and then left at room temperature for 2 days (d). The reaction mixture was filtered through a pad of Celite® and the filtrate was concentrated. The crude residue was purified via flash column chromatography (SiO₂, 0→20% EtOAc in hexanes) to furnish the title compound (1.12 g, 95%) as a colorless oil: IR (Thin Film) 2972, 2930, 2871, 1612, 1513 cm⁻¹; $^1$H NMR (400 MHz, CDCl₃) δ 7.29-7.18 (m, 4H), 6.91 (tt, J=7.4, 1.1 Hz, 1H), 6.84-6.80 (m, 4H), 4.59 (dd, J=5.6, 4.9 Hz, 1H), 4.51 (d, J=11.2 Hz, 1H), 4.34 (d, J=11.3 Hz, 1H), 4.09 (dd, J=10.3, 3.1 Hz, 1H), 4.03 (dd, J=10.3, 7.0 Hz, 1H), 3.88 (dt, J=6.9, 3.4 Hz, 1H), 3.77 (s, 3H), 3.74 (dd, J=10.5, 5.0 Hz, 1H), 3.72-3.63 (m, 3H), 3.60-3.49 (m, 3H), 1.88-1.79 (m, 1H), 1.49-1.38 (m, 2H), 1.36-1.25 (m, 4H), 1.24-1.14 (m, 9H), 0.89 (t, J=7.0 Hz, 3H); ESIMS m/z 511 ([M+Na]⁺).

Example 5, Steps 1 and 2: Preparation methyl 2-((tert-butoxycarbonyl)amino)-4-(((3R,4S,5S)-4-(4-fluorobenzyl)-5-((4-methoxybenzyl)oxy)-1-phenylhexan-3-yl)oxy)but-2-enoate

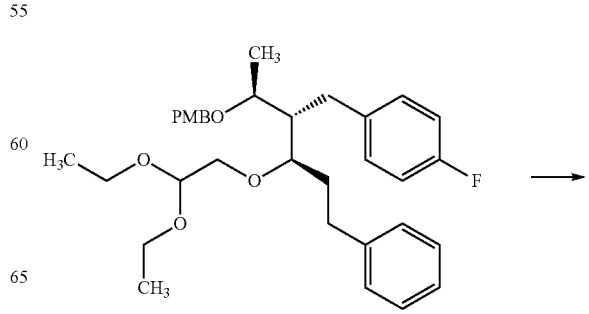

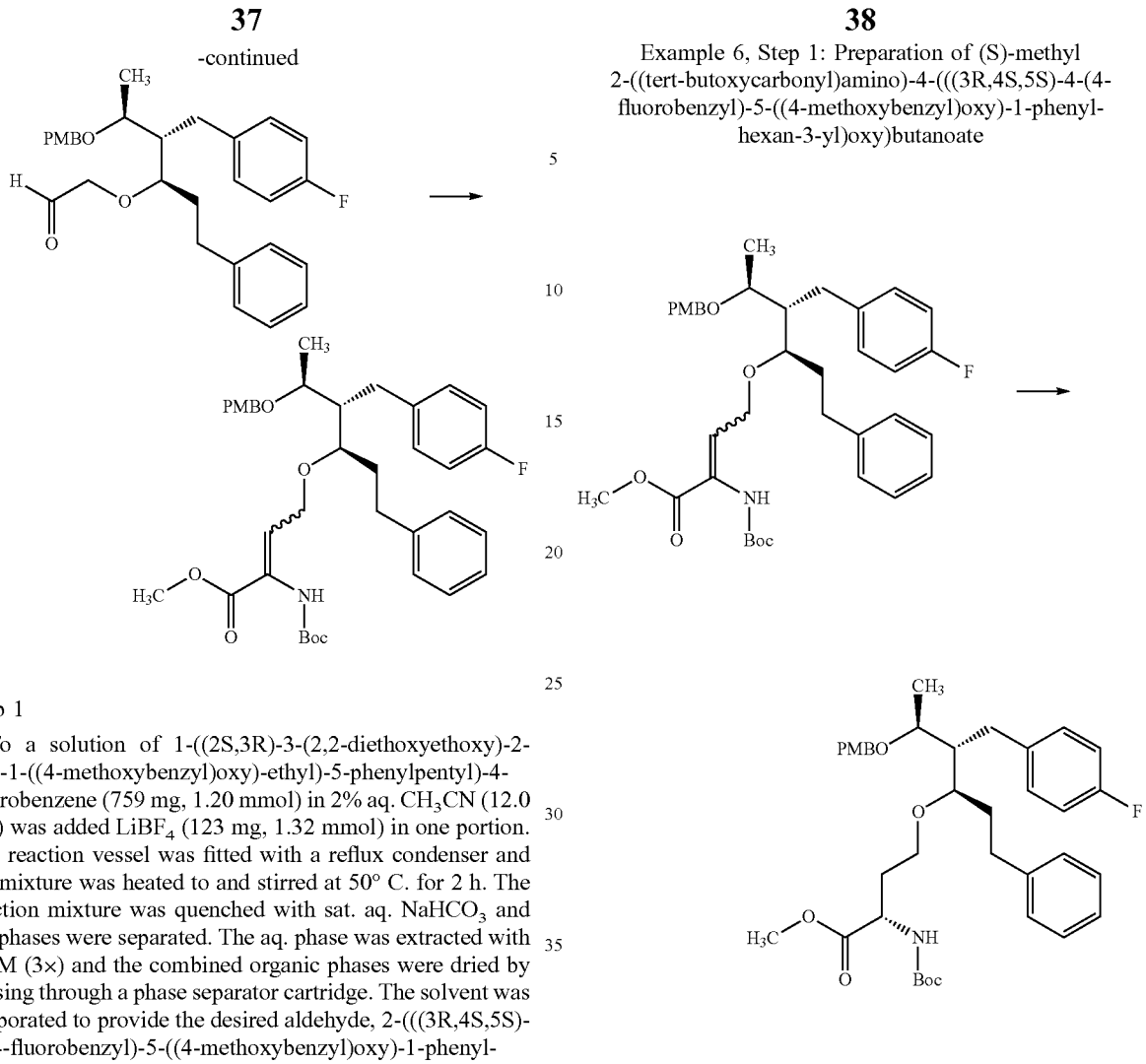

Example 6, Step 1: Preparation of (S)-methyl 2-((tert-butoxycarbonyl)amino)-4-(((3R,4S,5S)-4-(4-fluorobenzyl)-5-((4-methoxybenzyl)oxy)-1-phenyl-hexan-3-yl)oxy)butanoate Step 1

To a solution of 1-((2S,3R)-3-(2,2-diethoxyethoxy)-2-((S)-1-((4-methoxybenzyl)oxy)-ethyl)-5-phenylpentyl)-4-fluorobenzene (759 mg, 1.20 mmol) in 2% aq. CH$_3$CN (12.0 mL) was added LiBF$_4$ (123 mg, 1.32 mmol) in one portion. The reaction vessel was fitted with a reflux condenser and the mixture was heated to and stirred at 50° C. for 2 h. The reaction mixture was quenched with sat. aq. NaHCO$_3$ and the phases were separated. The aq. phase was extracted with DCM (3×) and the combined organic phases were dried by passing through a phase separator cartridge. The solvent was evaporated to provide the desired aldehyde, 2-(((3R,4S,5S)-4-(4-fluorobenzyl)-5-((4-methoxybenzyl)oxy)-1-phenyl-hexan-3-yl)oxy)acetaldehyde as a colorless oil.

Step 2

To a solution of 2-(((3R,4S,5S)-4-(4-fluorobenzyl)-5-((4-methoxybenzyl)oxy)-1-phenylhexan-3-yl)oxy)acetaldehyde in DCM (13.5 mL) was added methyl 2-((tert-butoxycarbonyl)amino)-2-(dimethoxyphosphoryl)acetate (356 mg, 1.20 mmol) and the reaction mixture was cooled to 0° C. and treated with DBU (0.145 mL, 1.26 mmol). The reaction vessel was sealed, left in the ice bath, and allowed to slowly warm to room temperature over the weekend. The reaction mixture was quenched with sat. aq. NH$_4$Cl and then the phases were separated. The aq. phase was extracted with DCM (3×) and the combined organic phases were dried by passing through a phase separator cartridge. The solvent was evaporated and the crude residue was purified by flash column chromatography (SiO$_2$, 1→15% acetone in hexanes) to afford the title compound (566 mg, 74%) as a predominately single alkene isomer: $^1$H NMR (400 MHz, CDCl$_3$) δ 7.26-7.19 (m, 4H), 7.19-7.11 (m, 1H), 7.09-6.98 (m, 4H), 6.96-6.83 (m, 4H), 6.49 (t, J=5.7 Hz, 2H), 4.50 (d, J=11.4 Hz, 1H), 4.25 (d, J=11.4 Hz, 1H), 4.11 (d, J=5.8 Hz, 2H), 3.81 (s, 3H), 3.80 (d, J=2.3 Hz, 3H), 3.56 (dt, J=6.5, 3.2 Hz, 1H), 3.48 (dt, J=7.8, 3.8 Hz, 1H), 2.78-2.66 (m, 2H), 2.63 (dd, J=9.6, 5.3 Hz, 1H), 2.54 (ddd, J=13.8, 9.8, 6.6 Hz, 1H), 2.08 (tt, J=7.8, 3.9 Hz, 1H), 2.03-1.88 (m, 1H), 1.84-1.71 (m, 1H), 1.45 (s, 9H), 1.12 (d, J=6.3 Hz, 3H); $^{19}$F NMR (376 MHz, CDCl$_3$) δ −117.92; ESIMS m/z 658 ([M+Na]$^+$).

To a steel high pressure reactor was added methyl 2-((tert-butoxycarbonyl)amino)-4-(((3R,4S,5S)-4-(4-fluorobenzyl)-5-((4-methoxybenzyl)oxy)-1-phenylhexan-3-yl)oxy)but-2-enoate (566 mg, 0.890 mmol) and MeOH (15 mL). The mixture was sparged with N$_2$ for 20 min, treated with (S,S)-Et-DUPHOS-Rh (9.65 mg, 0.013 mmol), and then the reactor was sealed, pressurized with H$_2$ 200 pounds per square inch (psi), and vented. The process was repeated three times, and then the reactor was pressurized to 200 psi with H$_2$ and stirred vigorously over the weekend. The solvent was evaporated and the resulting pale yellow oil was purified by flash column chromatography (SiO$_2$, 1→25% acetone in hexanes) to afford the title compound (565 mg, 100%) as a colorless oil: $^1$H NMR (400 MHz, CDCl$_3$) δ 7.23 (t, J=8.0 Hz, 4H), 7.15 (t, J=7.3 Hz, 1H), 7.10-7.00 (m, 4H), 6.93 (t, J=8.7 Hz, 2H), 6.88 (d, J=8.6 Hz, 2H), 5.60 (d, J=7.8 Hz, 1H), 4.49 (d, J=11.3 Hz, 1H), 4.46-4.37 (m, 1H), 4.24 (d, J=11.4 Hz, 1H), 3.80 (s, 3H), 3.73 (s, 3H), 3.55 (dd, J=6.4, 4.7 Hz, 1H), 3.51-3.45 (m, 1H), 3.45-3.36 (m, 2H), 2.79-2.59 (m, 3H), 2.53 (ddd, J=13.7, 9.8, 6.6 Hz, 1H), 2.12-2.03 (m, 2H), 2.01-1.85 (m, 2H), 1.81-1.64 (m, 1H), 1.41 (s, 9H), 1.12 (d, J=6.2 Hz, 3H); $^{19}$F NMR (376 MHz, CDCl$_3$) δ −117.93; ESIMS m/z 660 ([M+Na]$^+$).

Example 6, Step 2: Preparation of (S)-methyl 2-((tert-butoxycarbonyl)amino)-4-(((3R,4S,5S)-4-(4-fluorobenzyl)-5-hydroxy-1-phenylhexan-3-yl)oxy)butanoate

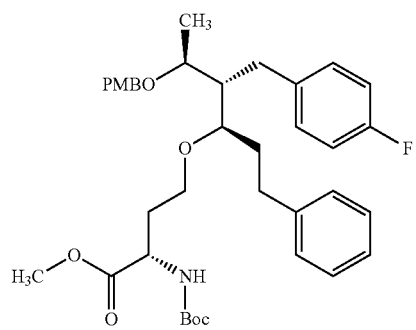

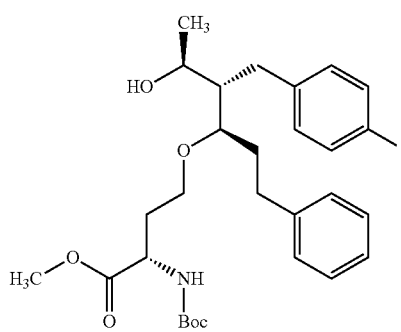

To a solution of (S)-methyl 2-((tert-butoxycarbonyl)amino)-4-(((3R,4S,5S)-4-(4-fluorobenzyl)-5-((4-methoxybenzyl)oxy)-1-phenylhexan-3-yl)oxy)butanoate (565 mg, 0.886 mmol) in DCM (3 mL) and water (0.3 mL) at 0° C. was added 4,5-dichloro-3,6-dioxocyclohexa-1,4-diene-1,2-dicarbonitrile (211 mg, 0.930 mmol) and the mixture was vigorously stirred for 45 min, and then treated with 1 M aq. NaOH (930 µL, 0.930 mmol) and water (6 mL). The reaction was removed from the cold bath and the phases were separated. The aqueous phase was extracted with DCM (3×) and the combined organic phases were dried by passing through a phase separator cartridge. The solvent was evaporated and the resulting oil was purified by flash column chromatography (SiO$_2$, 1→20% acetone in hexanes) to afford the title compound (440 mg, 96%) as a colorless oil: $^1$H NMR (400 MHz, CDCl$_3$) δ 7.25-7.20 (m, 2H), 7.19-7.08 (m, 3H), 7.08-7.03 (m, 2H), 6.96 (t, J=8.7 Hz, 2H), 5.46 (d, J=8.2 Hz, 1H), 4.45 (td, J=9.1, 8.4, 5.2 Hz, 1H), 3.96-3.81 (m, 1H), 3.74 (s, 3H), 3.50 (ddd, J=9.3, 8.2, 4.3 Hz, 1H), 3.43 (dt, J=9.5, 5.1 Hz, 1H), 3.35 (td, J=6.2, 5.6, 3.1 Hz, 1H), 2.73-2.60 (m, 2H), 2.60-2.47 (m, 2H), 2.28-2.17 (m, 1H), 2.17-2.02 (m, 1H), 2.03-1.79 (m, 4H), 1.42 (s, 9H), 1.22 (d, J=6.4 Hz, 3H); $^{19}$F NMR (376 MHz, CDCl$_3$) δ −117.51; ESIMS m/z 518 ([M+H]$^+$).

Example 6, Step 3: Preparation of (S)-2-((tert-butoxycarbonyl)amino)-4-(((3R,4S,5S)-4-(4-fluorobenzyl)-5-hydroxy-1-phenylhexan-3-yl)oxy)butanoic acid

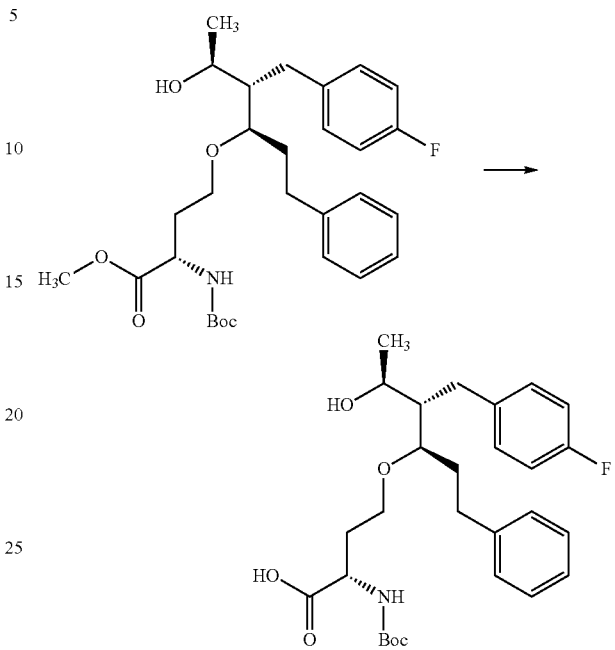

To a solution of (S)-methyl 2-((tert-butoxycarbonyl)amino)-4-(((3R,4S,5S)-4-(4-fluorobenzyl)-5-hydroxy-1-phenylhexan-3-yl)oxy)butanoate (430 mg, 0.831 mmol) in THF (5.5 mL) and water (2.8 mL) was added LiOH.H$_2$O (105 mg, 2.49 mmol). After 3 h, the reaction mixture was diluted with EtOAc (10 mL) and washed with 0.2 M aq. HCl (10 mL) followed by brine. The organic phase was dried over Na$_2$SO$_4$, filtered, and the solvent was evaporated to afford the title compound (423 mg, 96%) as a colorless oil: $^1$H NMR (400 MHz, CDCl$_3$) δ 7.25-7.17 (m, 2H), 7.16-7.13 (m, 1H), 7.10 (dd, J=8.5, 5.5 Hz, 2H), 7.05-7.00 (m, 2H), 6.95 (t, J=8.7 Hz, 2H), 5.55 (d, J=7.4 Hz, 1H), 4.42 (q, J=6.4 Hz, 1H), 3.93 (p, J=6.2 Hz, 1H), 3.63-3.51 (m, 1H), 3.44 (dt, J=9.7, 5.4 Hz, 1H), 3.36 (td, J=6.2, 3.0 Hz, 1H), 2.71-2.57 (m, 2H), 2.58-2.44 (m, 2H), 2.21-2.06 (m, 1H), 2.05-1.77 (m, 5H), 1.42 (s, 9H), 1.41-1.40 (m, 1H), 1.23 (d, J=6.2 Hz, 3H); $^{19}$F NMR (376 MHz, CDCl$_3$) δ −117.37; ESIMS m/z 504 ([M+H]$^+$).

Example 7, Step 1: Preparation of tert-butyl ((2R,3S,4S,7S)-3-(4-fluorobenzyl)-4-methyl-6-oxo-2-phenethyl-1,5-dioxonan-7-yl)carbamate (Cmpd 97)

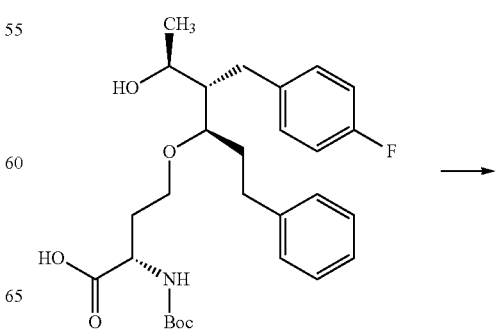

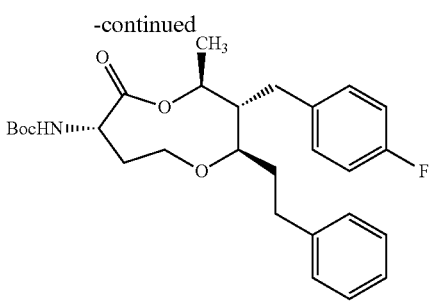

To a solution of MNBA (572 mg, 1.66 mmol) and DMAP (608 mg, 4.98 mmol) in DCM (70 mL) was added a solution of (S)-2-((tert-butoxycarbonyl)amino)-4-(((3R,4S,5S)-4-(4-fluorobenzyl)-5-hydroxy-1-phenylhexan-3-yl)oxy)butanoic acid (418 mg, 0.830 mmol) in DCM (50 mL) dropwise over an 8 h period. Upon completion of the addition, the reaction mixture was stirred overnight at room temperature and then quenched with 0.2 M aq. HCl (100 mL). The phases were separated and the organic phase was washed with half sat. aq. NaHCO$_3$ (100 mL) and dried by passing through a phase separator cartridge. The solvent was evaporated and the crude residue was purified by flash column chromatography (SiO$_2$, 1→25% acetone in hexanes) to give the title compound (249 mg, 62%) as a white foam: See Table 2 for characterization data.

Example 8, Step 1: Preparation of tert-butyl ((2S,3S,4S,7S)-3-butyl-2-(hydroxymethyl)-4-methyl-6-oxo-1,5-dioxonan-7-yl)carbamate

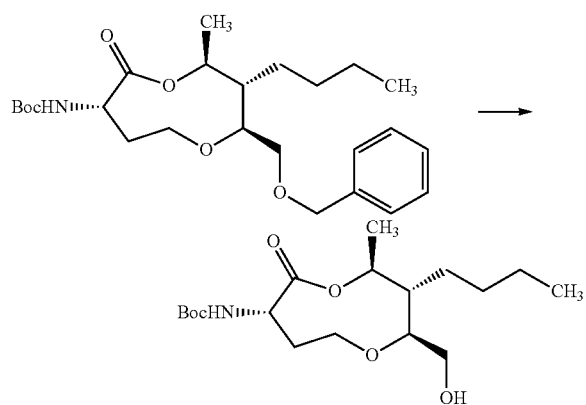

To a solution of tert-butyl ((2S,3S,4S,7S)-2-((benzyloxy)methyl)-3-butyl-4-methyl-6-oxo-1,5-dioxonan-7-yl)carbamate (110 mg, 0.245 mmol) in MeOH (5 mL) was added 10% Pd/C (25 mg, 0.023 mmol). A balloon of H$_2$ gas was fitted to the reaction vessel. After 24 h of vigorous stirring, the reaction mixture was filtered through a pad of Celite® and the pad was washed with MeOH. The solvent was removed to afford the title compound (85.5 mg, 97%) as a colorless oil; $^1$H NMR (400 MHz, CDCl$_3$) δ 5.18 (d, J=8.0 Hz, 1H), 5.15-5.06 (m, 1H), 4.25 (q, J=8.4 Hz, 1H), 3.82-3.63 (m, 4H), 3.58-3.49 (m, 1H), 2.30 (dd, J=15.2, 7.6 Hz, 1H), 2.05 (s, 1H), 1.93-1.80 (m, 1H), 1.81-1.68 (m, 1H), 1.68-1.54 (m, 2H), 1.44 (s, 9H), 1.34 (d, J=6.4 Hz, 3H), 1.32-1.20 (m, 4H), 0.89 (t, J=7.0 Hz, 3H); $^{13}$C NMR (101 MHz, CDCl$_3$) δ 172.45, 155.00, 81.06, 79.83, 74.51, 61.30, 59.17, 51.11, 40.27, 34.56, 28.34, 27.61, 27.29, 23.32, 19.21, 13.82; ESIMS m/z 360 ([M+H]$^+$).

Example 8, Step 2: Preparation of ((2S,3S,4S,7S)-7-((tert-butoxycarbonyl)amino)-3-butyl-4-methyl-6-oxo-1,5-dioxonan-2-yl)methyl isobutyrate (Cmpd 105)

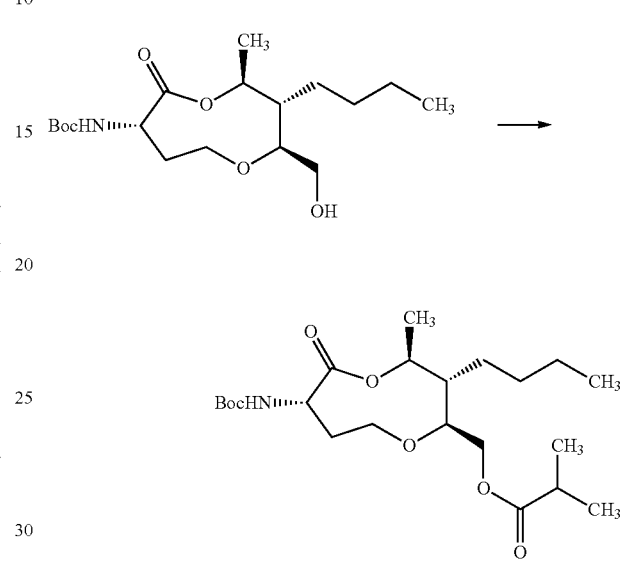

To a solution of tert-butyl ((2S,3S,4S,7S)-3-butyl-2-(hydroxymethyl)-4-methyl-6-oxo-1,5-dioxonan-7-yl)carbamate (0.090 g, 0.250 mmol) in pyridine (1.0 mL) was added DMAP (6.12 mg, 0.050 mmol) followed by isobutyryl chloride (0.052 mL, 0.501 mmol). The reaction mixture was stirred at room temperature for 16 h and then quenched with sat. aq. NH$_4$Cl (1 mL). The phases were separated and the aqueous phase was extracted with DCM (3×4 mL). The combined extracts were dried by passing through a phase separator and the solvent was evaporated. The resulting residue was purified by flash column chromatography (SiO$_2$, 0→30% EtOAc in hexanes) to afford the title compound (0.085 g, 79%) as a colorless oil: See Table 2 for characterization data.

Example 9, Steps 1 and 2: Preparation of N-((2R,3S,4S,7S)-3-(4-fluorobenzyl)-4-methyl-6-oxo-2-phenethyl-1,5-dioxonan-7-yl)-3-hydroxy-4-methoxypicolinamide (Cmpds 77 and 57)

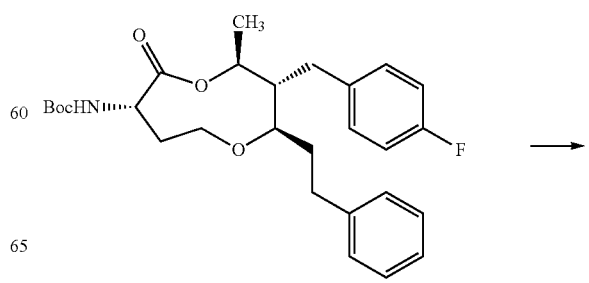

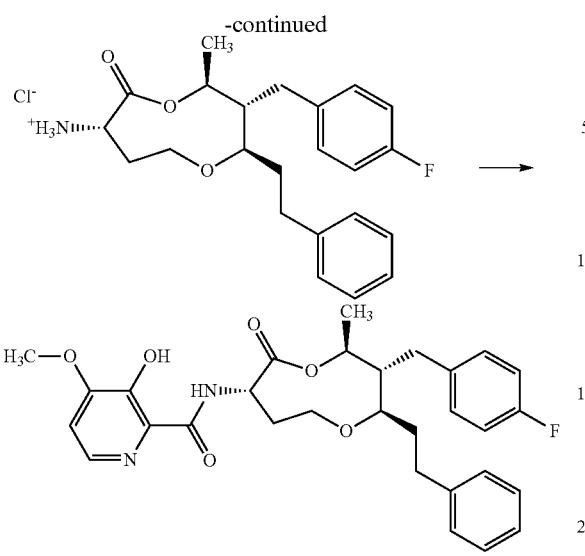

Step 1 (Cmpd 77)

To a solution of tert-butyl ((2R,3S,4S,7S)-3-(4-fluorobenzyl)-4-methyl-6-oxo-2-phenethyl-1,5-dioxonan-7-yl)carbamate (249 mg, 0.513 mmol) in DCM (3944 μL) was added a 4 M solution of HCl in dioxane (2.5 mL, 10.2 mmol). After 3 h at room temperature, the solvent was evaporated under a stream of N$_2$ to provide the intermediate amine hydrochloride, (2R,3S,4S,7S)-3-(4-fluorobenzyl)-4-methyl-6-oxo-2-phenethyl-1,5-dioxonan-7-aminium chloride, as a pale yellow solid: See Table 2 for characterization data.

Step 2 (Cmpd 57)

To a solution of (2R,3S,4S,7S)-3-(4-fluorobenzyl)-4-methyl-6-oxo-2-phenethyl-1,5-dioxonan-7-aminium chloride and 3-hydroxy-4-methoxypicolinic acid (95 mg, 0.56 mmol) in DCM (4 mL) were added N-ethyl-N-isopropylpropan-2-amine (295 μL, 1.69 mmol) and PYBOP (294 mg, 0.564 mmol). The reaction vessel was sealed and the mixture was stirred at room temperature for 4 h. The solvent was evaporated and the crude oil was purified by flash column chromatography (SiO$_2$, 1→50% acetone in hexanes) to afford the title compound (244 mg, 89%) as a white solid: See Table 2 for characterization data.

Example 10: Preparation of ((2-(((2R,3S,4S,7S)-3-(4-fluorobenzyl)-4-methyl-6-oxo-2-phenethyl-1,5-dioxonan-7-yl)carbamoyl)-4-methoxypyridin-3-yl)oxy)methyl acetate (Cmpd 24)

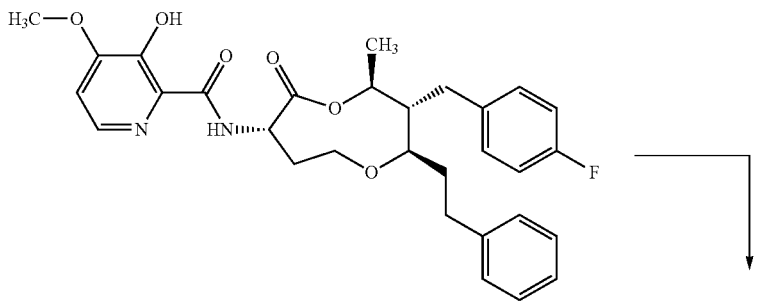

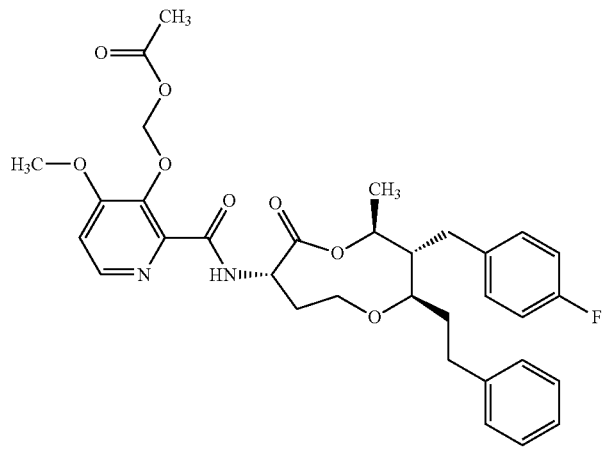

To a solution of N-((2R,3S,4S,7S)-3-(4-fluorobenzyl)-4-methyl-6-oxo-2-phenethyl-1,5-dioxonan-7-yl)-3-hydroxy-4-methoxypicolinamide (73 mg, 0.14 mmol) and $K_2CO_3$ (37.6 mg, 0.272 mmol) in acetone (1.4 mL) was added bromomethyl acetate (18.7 μL, 0.190 mmol) dropwise. The reaction vessel was sealed and heated to 50° C. and stirred for 4 h. The mixture was filtered through a fitted filter rinsing with a 3:1 mixture of hexanes and acetone. The solvent was evaporated and the crude residue was purified by flash column chromatography ($SiO_2$, 1→50% acetone in hexanes) to afford the title compound (66.8 mg, 81%) as a white foam: See Table 2 for characterization data.

Example 11: Preparation of 2-(((2R,3S,4S,7S)-3-(4-fluorobenzyl)-4-methyl-6-oxo-2-phenethyl-1,5-dioxonan-7-yl)carbamoyl)-4-methoxypyridin-3-yl acetate (Cmpd 7)

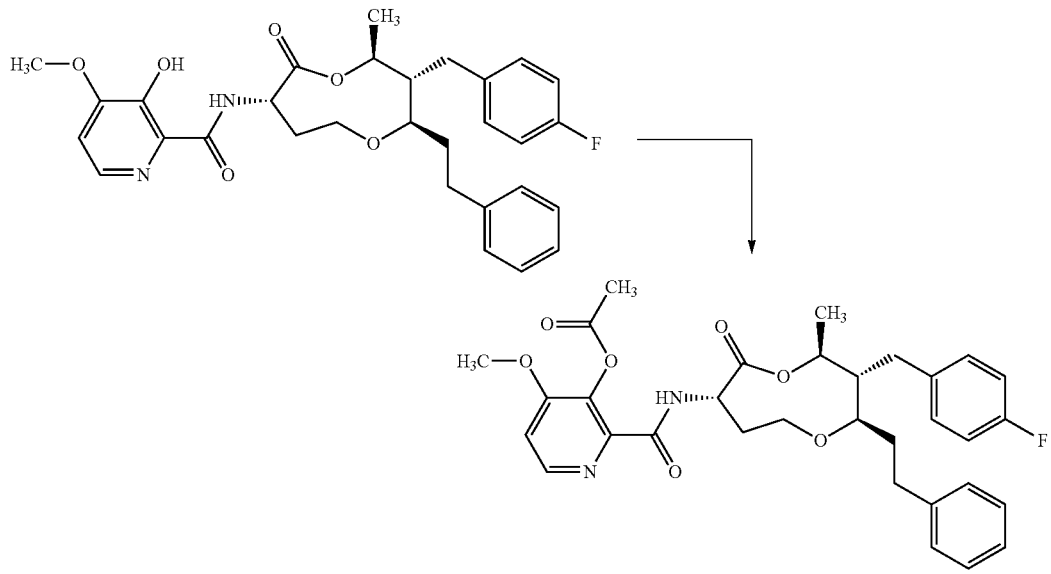

To a solution of N-((2R,3S,4S,7S)-3-(4-fluorobenzyl)-4-methyl-6-oxo-2-phenethyl-1,5-dioxonan-7-yl)-3-hydroxy-4-methoxypicolinamide (73 mg, 0.14 mmol), $NEt_3$ (38 μL, 0.272 mmol), and DMAP (3.3 mg, 0.027 mmol) in DCM (1.4 mL) was added acetyl chloride (14.56 μL, 0.204 mmol) and the mixture was stirred for 3 h at room temperature. The reaction mixture was diluted with DCM, poured into sat. aq. $NH_4Cl$, and the phases were separated. The aq. phase was extracted with DCM (3×) and the combined organics were dried by passing through a phase separator cartridge. The solvent was evaporated and the crude oil was purified by flash column chromatography ($SiO_2$, 1→50% acetone in hexanes) to afford the title compound (77.9 mg, 99%) as a white foam: See Table 2 for characterization data.

Example 12: Preparation of ((2-(((2R,3S,4S,7S)-2,3-dibenzyl-4-methyl-6-oxo-1,5-dioxonan-7-yl)carbamoyl)-4-methoxypyridin-3-yl)oxy)methyl isobutyrate (Cmpd. 37)

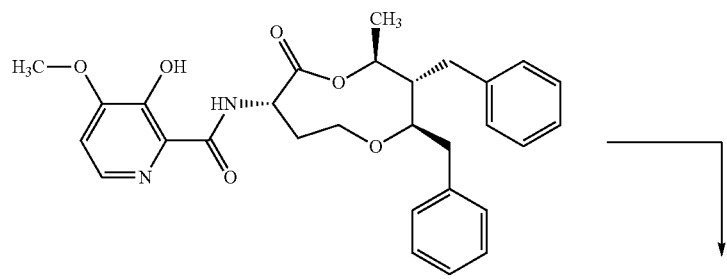

-continued

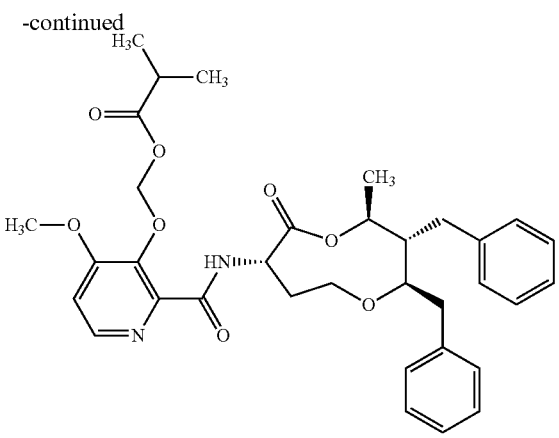

A 10 mL screw top vial was charged with N-((2R,3S,4S,7S)-2,3-dibenzyl-4-methyl-6-oxo-1,5-dioxonan-7-yl)-3-hydroxy-4-methoxypicolinamide (90.0 mg, 0.178 mmol), sodium carbonate (Na$_2$CO$_3$, 37.8 mg, 0.357 mmol), sodium iodide (NaI, 5.3 mg, 0.036 mmol), anhydrous acetone (1.78 mL) and chloromethyl isobutyrate (39.0 mg, 0.285 mmol). The resulting mixture was heated to 55° C. and stirred at that temperature overnight. The crude reaction mixture was cooled to room temperature, filtered through a pad of Celite® rinsing with a 3:1 mixture of hexanes and acetone, and the filtrate was concentrated. The resulting oil was purified via column chromatography (SiO$_2$, 1→50% acetone in hexanes) to give the title compound (84.2 mg, 78%) as a white foam: See Table 2 for characterization data.

Example 13: Preparation of 2-(((3R,4S,7S)-3-benzyl-4-methyl-6-oxo-1,5-dioxonan-7-yl)carbamoyl)-4-methoxypyridin-3-yl 2-ethoxyacetate (Cmpd. 48) and ((2-(((3R,4S,7S)-3-benzyl-4-methyl-6-oxo-1,5-dioxonan-7-yl)carbamoyl)-4-methoxypyridin-3-yl)oxy)methyl 2-ethoxyacetate (Cmpd. 42)

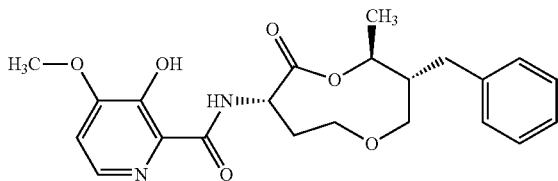

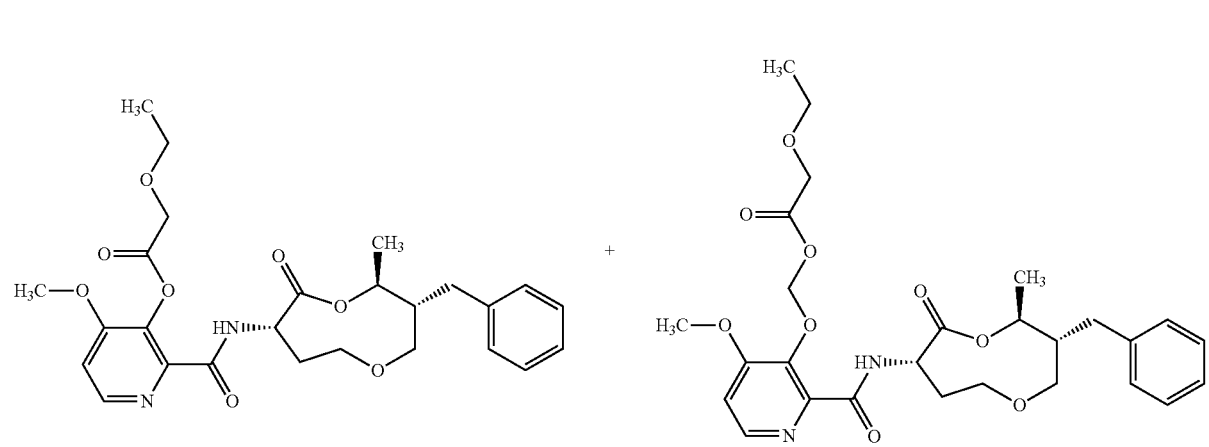

A 10 mL screw top vial was charged with N-((3R,4S,7S)-3-benzyl-4-methyl-6-oxo-1,5-dioxonan-7-yl)-3-hydroxy-4-methoxypicolinamide (83.0 mg, 0.182 mmol), $Na_2CO_3$ (41.9 mg, 0.396 mmol), NaI (5.93 mg, 0.040 mmol), anhydrous acetone (2.0 mL), and chloromethyl 2-ethoxyacetate (40.2 µl, 0.317 mmol), and the resulting mixture was heated to 55° C. and stirred at that temperature overnight. The reaction mixture was cooled to room temperature, treated with additional chloromethyl 2-ethoxyacetate (13 µL, 0.10 mmol), warmed to 55° C., and stirred for 5 h. The crude reaction mixture was cooled to room temperature, filtered through a plug of Celite® rinsing with a 3:1 mixture of hexanes and acetone, and concentrated. The crude concentrate was purified via column chromatography ($SiO_2$, 1→50% acetone in hexanes) to give the title compounds (42, 35.2 mg, 36% and 48, 53.5 mg, 51%) as white foams: See Table 2 for characterization data.

Example A: Evaluation of Fungicidal Activity: Leaf Blotch of Wheat (*Mycosphaerella graminicola*; Anamorph: *Zymoseptoria tritici*; Bayer code SEPTTR)

Technical grades of materials were dissolved in acetone, which were then mixed with nine volumes of water containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases, unless stated otherwise. Wheat leaf blotch and brown rust activity were also evaluated using track spray applications, in which case the fungicides were formulated as EC formulations, containing 0.1% Trycol 5941 in the spray solutions.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the $1^{st}$ leaves of untreated plants, infection levels were assessed on a scale of 0 to 100 percent disease severity. Percent disease control was calculated using the ratio of disease severity on treated plants relative to untreated plants.

Example B: Evaluation of Fungicidal Activity: Wheat Brown Rust (*Puccinia triticina*; Synonym: *Puccinia recondita* f. sp. *tritici*; Bayer code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A.

Example C: Evaluation of Fungicidal Activity: Wheat Glume Blotch (*Leptosphaeria nodorum*; Bayer code LEPTNO)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Leptosphaeria nodorum* 24 hr after fungicide treatments. After inoculation the plants were kept in 100% relative humidity (one day in a dark dew chamber followed by two days in a lighted dew chamber at 20° C.) to permit spores to germinate and infect the leaf. The plants were then transferred to a greenhouse set at 20° C. for disease to develop. Fungicide formulation, application and disease assessment followed the procedures as described in the Example A.

Example D: Evaluation of Fungicidal Activity: Apple Scab (*Venturia inaequalis*; Bayer Code VENTIN)

Apple seedlings (variety McIntosh) were grown in soil-less Metro mix, with one plant per pot. Seedlings with two expanding young leaves at the top (older leaves at bottom of the plants were trimmed) were used in the test. Plants were inoculated with a spore suspension of *Venturia inaequalis* 24 hr after fungicide treatment and kept in a 22° C. dew chamber with 100% relative humidity for 48 hr, and then moved to a greenhouse set at 20° C. for disease to develop. Fungicide formulation, application and disease assessment on the sprayed leaves followed the procedures as described in the Example A.

Example E: Evaluation of Fungicidal Activity: Grape Powdery Mildew (*Uncinula Necator*; Bayer Code UNCINE)

Grape seedlings (variety Carignane) were grown in soil-less Metro mix, with one plant per pot, and used in the test when approximately one month old. Plants were inoculated 24 hr after fungicide treatment by shaking spores from infected leaves over test plants. Plants were maintained in a greenhouse set at 20° C. until disease was fully developed. Fungicide formulation, application and disease assessment on the sprayed leaves followed the procedures as described in the Example A.

Example F: Evaluation of Fungicidal Activity: Powdery Mildew of Cucumber (*Erysiphe cichoracearum*; Bayer Code ERYSCI)

Cucumber seedlings (variety Bush Pickle) were grown in soil-less Metro mix, with one plant per pot, and used in the test when 12 to 14 days old. Plants were inoculated with a spore suspension 24 hr following fungicide treatments. After inoculation the plants remained in the greenhouse set at 20° C. until disease was fully expressed. Fungicide formulation, application and disease assessment on the sprayed leaves followed the procedures as described in the Example A.

Example G: Evaluation of Fungicidal Activity: Leaf Spot of Sugar Beets (*Cercospora Beticola*; Bayer Code CERCBE)

Sugar beet plants (variety HH88) were grown in soil-less Metro mix and trimmed regularly to maintain a uniform plant size prior to test. Plants were inoculated with a spore suspension 24 hr after fungicide treatments. Inoculated plants were kept in a dew chamber at 22° C. for 48 hr then incubated in a greenhouse set at 24° C. under a clear plastic hood with bottom ventilation until disease symptoms were fully expressed. Fungicide formulation, application and disease assessment on the sprayed leaves followed the procedures as described in the Example A.

Example H: Evaluation of Fungicidal Activity: Asian Soybean Rust (*Phakopsora pachyrhizi*; Bayer Code PHAKPA)

Technical grades of materials were dissolved in acetone, which were then mixed with nine volumes of water containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two weeks old seedlings were used for testing. Plants were inoculated either 3 days prior to or 1 day after fungicide treatments. Plants were incubated for 24 h in a dark dew room at 22° C. and 100% relative humidity then transferred to a growth room at 23° C. for disease to develop. Disease severity was assessed on the sprayed leaves.

Example I: Evaluation of Fungicidal Activity: Wheat Powdery Mildew (*Blumeria Graminis* f. Sp. *Tritici*; Synonym: *Erysiphe graminis* f. Sp. *Tritici*; Bayer Code ERYSGT)

Wheat plants (variety Yuma) were grown from seed in a greenhouse in 50% mineral soil/50% soil-less Metro mix until the first leaf was fully emerged, with 7-10 seedlings per pot. These plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example J: Evaluation of Fungicidal Activity: Barley Powdery Mildew (*Blumeria graminis* f. sp. *hordei*; Synonym: *Erysiphe graminis* f. sp. *hordei*; Bayer Code ERYSGH)

Barley seedlings (variety Harrington) were propagated in soil-less Metro mix, with each pot having 8 to 12 plants, and used in the test when first leaf was fully emerged. Test plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example K: Evaluation of Fungicidal Activity: Barley Scald (*Rhyncosporium secalis*; Bayer Code RHYNSE)

Barley seedlings (variety Harrington) were propagated in soil-less Metro mix, with each pot having 8 to 12 plants, and used in the test when first leaf was fully emerged. Test plants were inoculated by an aqueous spore suspension of *Rhyncosporium secalis* 24 hr after fungicide treatments. After inoculation the plants were kept in a dew room at 20° C. with 100% relative humidity for 48 hr. The plants were then transferred to a greenhouse set at 20° C. for disease to develop. Fungicide formulation, application and disease assessment on the sprayed leaves followed the procedures as described in the Example A.

Example L: Evaluation of Fungicidal Activity: Rice Blast (*Magnaporthe grisea*; Anamorph: *Pyricularia oryzae*; Bayer Code PYRIOR)

Rice seedlings (variety *Japonica*) were propagated in soil-less Metro mix, with each pot having 8 to 14 plants, and used in the test when 12 to 14 days old. Test plants were inoculated with an aqueous spore suspension of *Pyricularia oryzae* 24 hr after fungicide treatments. After inoculation the plants were kept in a dew room at 22° C. with 100% relative humidity for 48 hr to permit spores to germinate and infect the leaf. The plants were then transferred to a greenhouse set at 24° C. for disease to develop. Fungicide formulation, application and disease assessment on the sprayed leaves followed the procedures as described in the Example A.

Example M: Evaluation of Fungicidal Activity: Tomato Early Blight (*Alternaria solani*; Bayer Code ALTESO)

Tomato plants (variety Outdoor Girl) were propagated in soil-less Metro mix, with each pot having one plant, and used when 12 to 14 days old. Test plants were inoculated with an aqueous spore suspension of *Alternaria solani* 24 hr after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a growth room at 22° C. for disease to develop. Fungicide formulation, application and disease assessment on the sprayed leaves followed the procedures as described in the Example A.

Example N: Evaluation of Fungicidal Activity: Cucumber Anthracnose (*Glomerella lagenarium*; Anamorph: *Colletotrichum lagenarium*; Bayer Code COLLLA)

Cucumber seedlings (variety Bush Pickle) were propagated in soil-less Metro mix, with each pot having one plant, and used in the test when 12 to 14 days old. Test plants were inoculated with an aqueous spore suspension of *Colletotrichum lagenarium* 24 hr after fungicide treatments. After inoculation the plants were kept in a dew room at 22° C. with 100% relative humidity for 48 hr to permit spores to germinate and infect the leaf. The plants were then transferred to a growth room set at 22° C. for disease to develop. Fungicide formulation, application and disease assessment on the sprayed leaves followed the procedures as described in the Example A.

TABLE 1

Compound Structure, Appearance, and Preparation Method

| Compound Number | Structure | Prepared According to Example | Appearance |
|---|---|---|---|
| 1 | 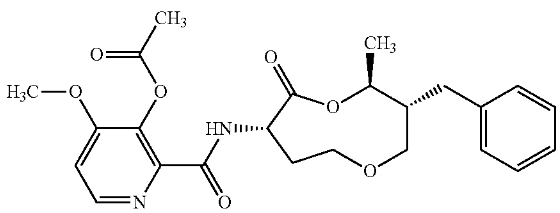 | Example 11 | White Foam |
| 2 | 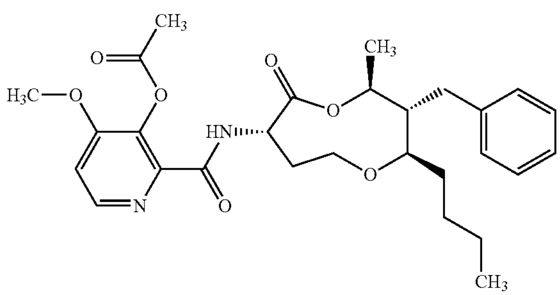 | Example 11 | White Foam |
| 3 | 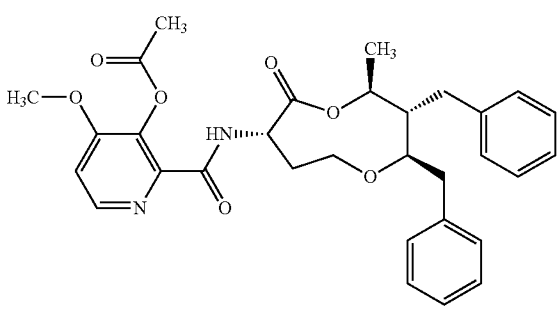 | Example 11 | White Foam |
| 4 | 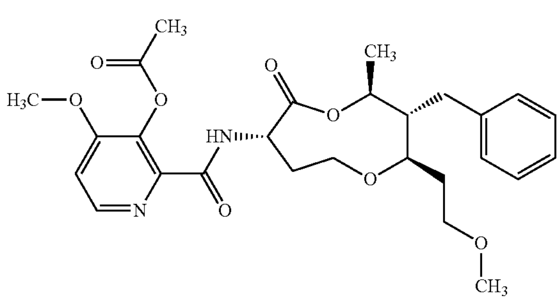 | Example 11 | White Foam |
| 5 | 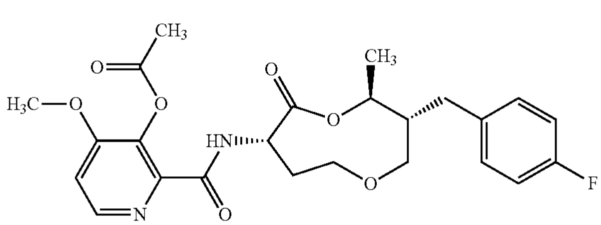 | Example 11 | White Foam |

TABLE 1-continued

Compound Structure, Appearance, and Preparation Method

| Compound Number | Structure | Prepared According to Example | Appearance |
|---|---|---|---|
| 6 | 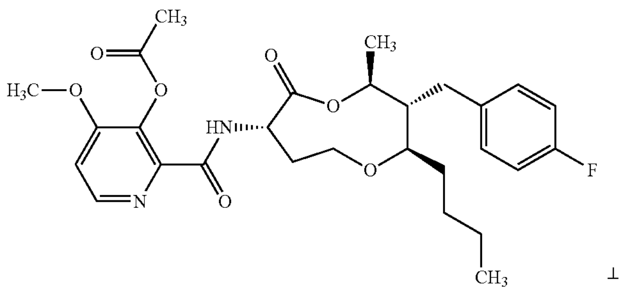 | Example 11 | White Foam |
| 7 | 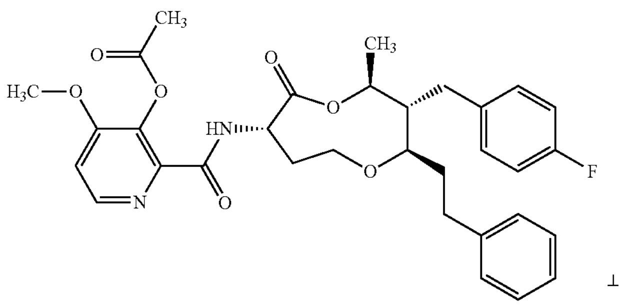 [SMILES: COc1ccnc(C(=O)N[C@H]2CCO[C@H](CCc3ccccc3)[C@@H](Cc3ccc(F)cc3)[C@H](C)OC2=O)c1OC(C)=O] | Example 11 | White Foam |
| 8 | 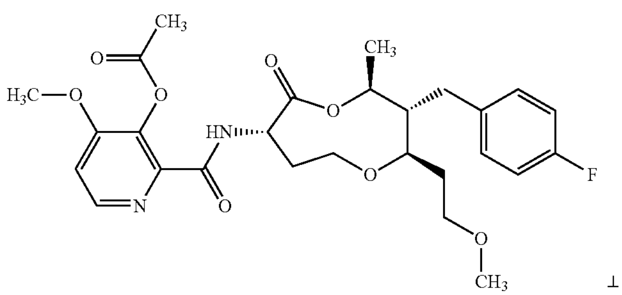 [SMILES: COCC[C@H]1OCC[C@H](NC(=O)c2nccc(OC)c2OC(C)=O)C(=O)O[C@@H](C)[C@@H]1Cc1ccc(F)cc1] | Example 11 | White Foam |
| 9 | 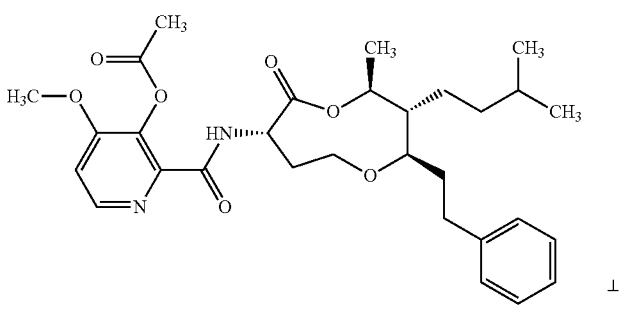 [SMILES: COc1ccnc(C(=O)N[C@H]2CCO[C@H](CCc3ccccc3)[C@@H](CCC(C)C)[C@H](C)OC2=O)c1OC(C)=O] | Example 11 | White Powder |
| 10 | 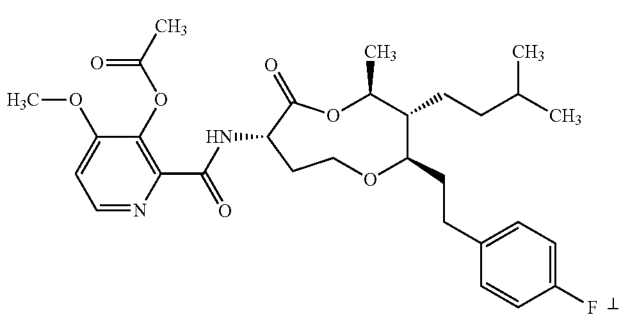 [SMILES: COc1ccnc(C(=O)N[C@H]2CCO[C@H](CCc3ccc(F)cc3)[C@@H](CCC(C)C)[C@H](C)OC2=O)c1OC(C)=O] | Example 11 | White Powder |

TABLE 1-continued

Compound Structure, Appearance, and Preparation Method

| Compound Number | Structure | Prepared According to Example | Appearance |
|---|---|---|---|
| 11 | 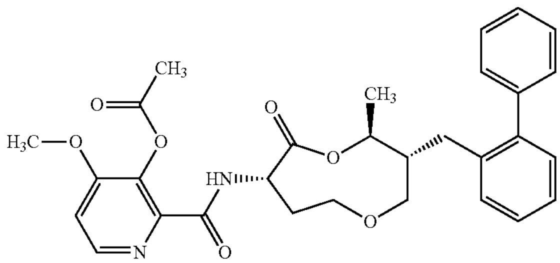 | Example 11 | White Powder |
| 12 | 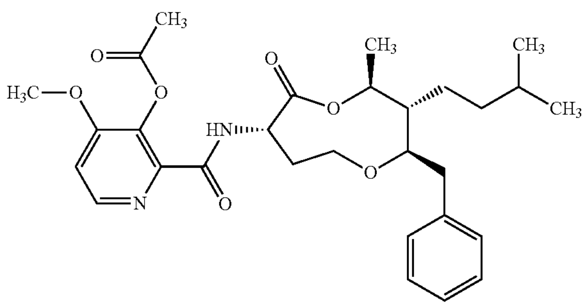 | Example 11 | White Powder |
| 13 | 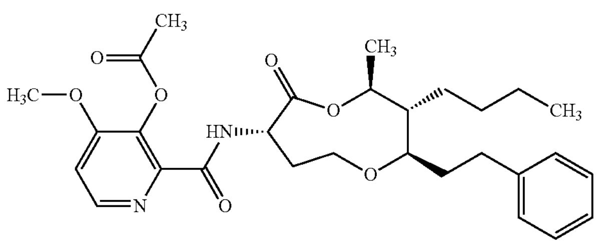 | Example 11 | White Foam |
| 14 | 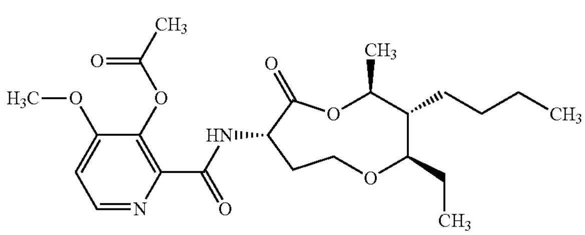 | Example 11 | Pale Yellow Solid |
| 15 | 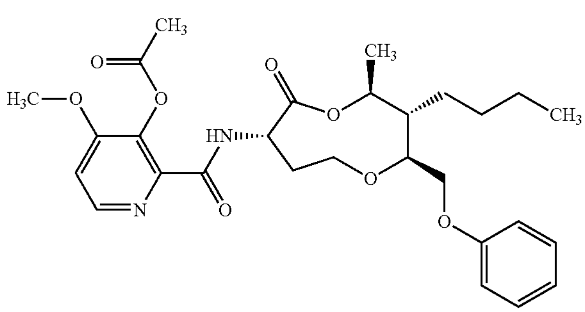 | Example 11 | Pale Yellow Oil |

TABLE 1-continued

Compound Structure, Appearance, and Preparation Method

| Compound Number | Structure | Prepared According to Example | Appearance |
|---|---|---|---|
| 16 | 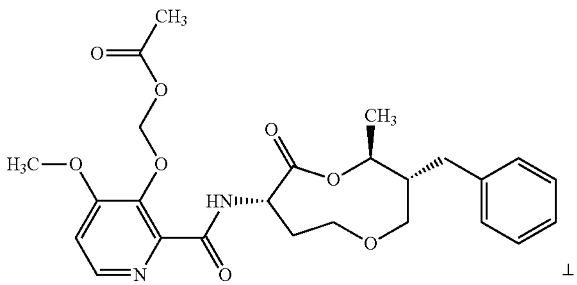 [SMILES: COc1ccnc(C(=O)N[C@H]2CCOC[C@@H](Cc3ccccc3)[C@H](C)OC2=O)c1OCOC(C)=O] | Example 10 | Off-White Solid |
| 17 | 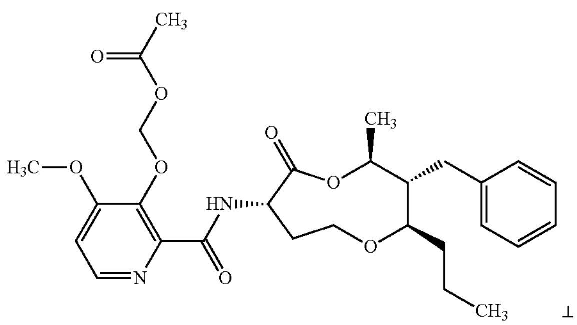 [SMILES: CCC[C@H]1OCC[C@H](NC(=O)c2nccc(OC)c2OCOC(C)=O)C(=O)O[C@@H](C)[C@@H]1Cc1ccccc1] | Example 10 | White Foam |
| 18 | 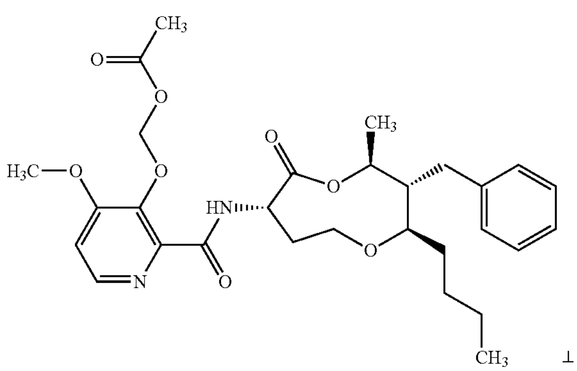 | Example 10 | White Foam |
| 19 | 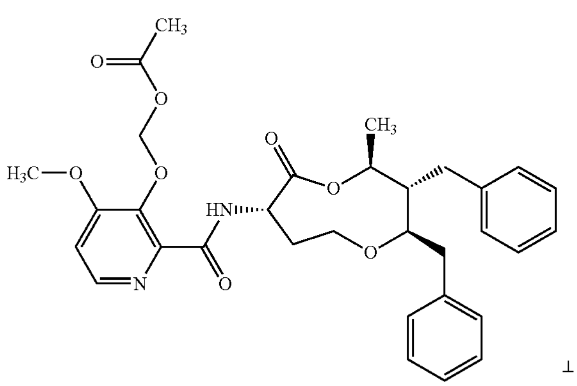 [SMILES: COc1ccnc(C(=O)N[C@H]2CCO[C@H](Cc3ccccc3)[C@@H](Cc3ccccc3)[C@H](C)OC2=O)c1OCOC(C)=O] | Example 10 | White Foam |

TABLE 1-continued

Compound Structure, Appearance, and Preparation Method

| Compound Number | Structure | Prepared According to Example | Appearance |
|---|---|---|---|
| 20 | (structure) | Example 10 | White Foam |
| 21 | (structure) | Example 10 | White Solid |
| 22 | (structure) | Example 10 | White Foam |
| 23 | (structure) | Example 10 | White Foam |

TABLE 1-continued

Compound Structure, Appearance, and Preparation Method

| Compound Number | Structure | Prepared According to Example | Appearance |
|---|---|---|---|
| 24 | 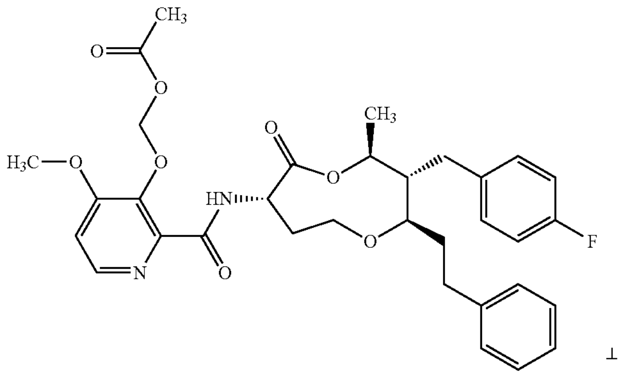 | Example 10 | White Foam |
| 25 | 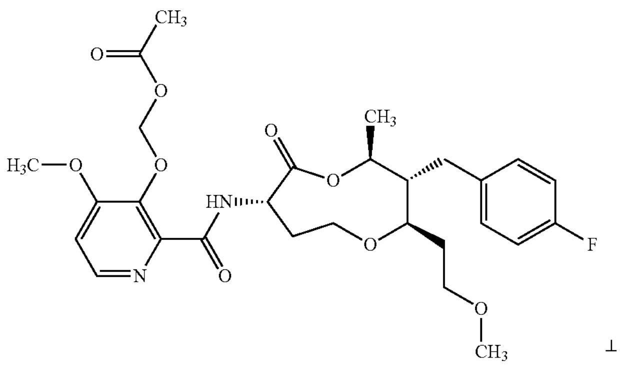 [SMILES: CCCC[C@H]1OCC[C@H](NC(=O)c2nccc(OC)c2OCOC(C)=O)C(=O)O[C@@H](C)[C@@H]1Cc1ccc(F)cc1] | Example 10 | White Foam |
| 26 | 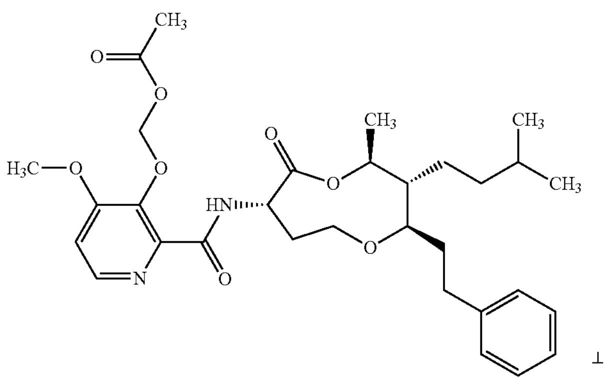 [SMILES: COc1ccnc(C(=O)N[C@H]2CCO[C@H](CCc3ccccc3)[C@@H](CCC(C)C)[C@H](C)OC2=O)c1OCOC(C)=O] | Example 10 | White Powder |
| 27 | 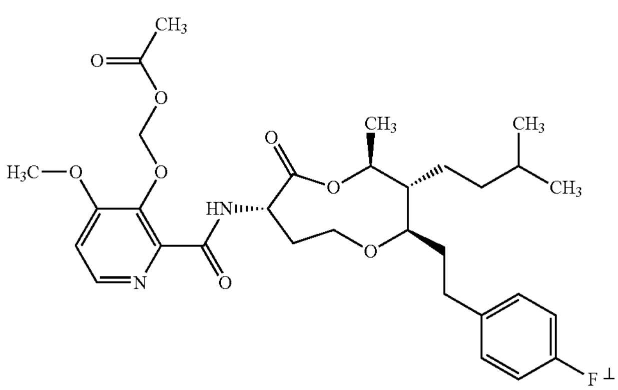 [SMILES: COc1ccnc(C(=O)N[C@H]2CCO[C@H](CCc3ccc(F)cc3)[C@@H](CCC(C)C)[C@H](C)OC2=O)c1OCOC(C)=O] | Example 10 | White Powder |

TABLE 1-continued
Compound Structure, Appearance, and Preparation Method
| Compound Number | Structure | Prepared According to Example | Appearance |
|---|---|---|---|
| 28 | 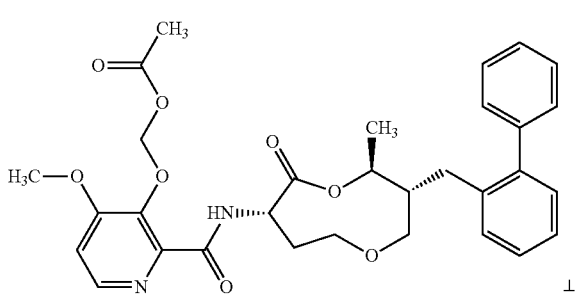 [SMILES: COc1ccnc(C(=O)N[C@H]2CCOC[C@@H](Cc3ccccc3-c3ccccc3)[C@H](C)OC2=O)c1OCOC(C)=O] | Example 10 | White Powder |
| 29 | 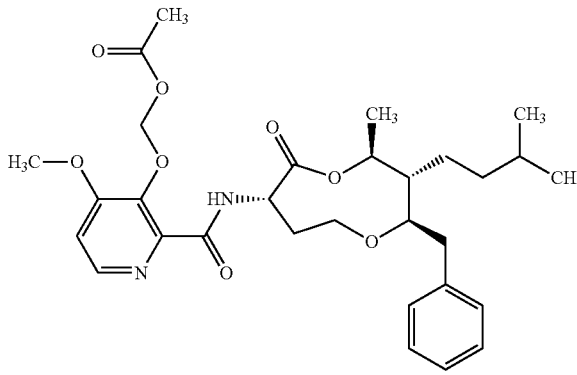 | Example 10 | White Powder |
| 30 | 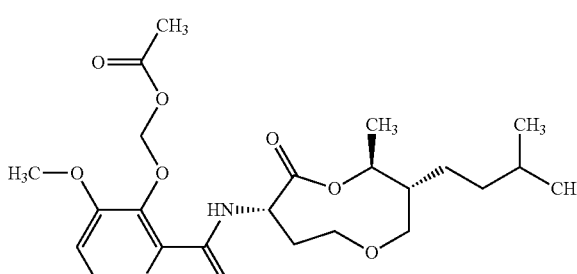 | Example 10 | White Solid |
| 31 | 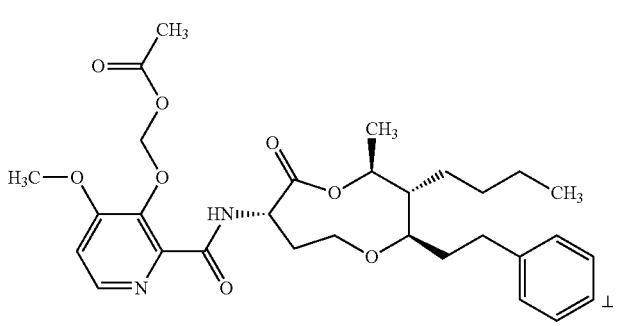 [SMILES: CCCC[C@H]1[C@H](C)OC(=O)[C@@H](NC(=O)c2nccc(OC)c2OCOC(C)=O)CCO[C@@H]1CCc1ccccc1] | Example 10 | White Foam |

TABLE 1-continued

Compound Structure, Appearance, and Preparation Method

| Compound Number | Structure | Prepared According to Example | Appearance |
|---|---|---|---|
| 32 | 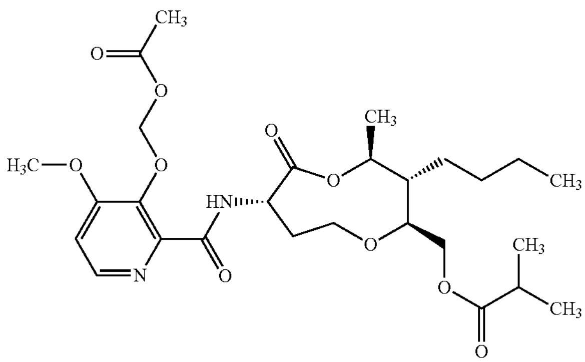 | Example 10 | Yellow Oil |
| 33 | 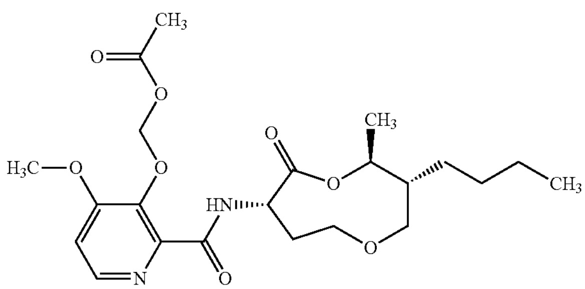 | Example 10 | White Solid |
| 34 | 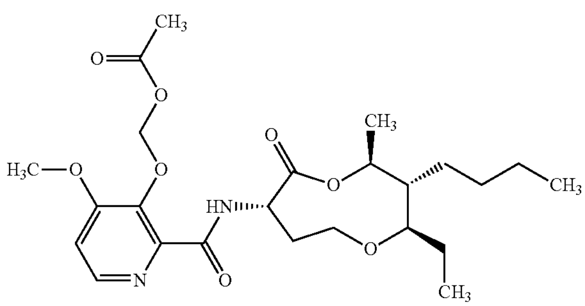 | Example 10 | Colorless Oil |
| 35 | 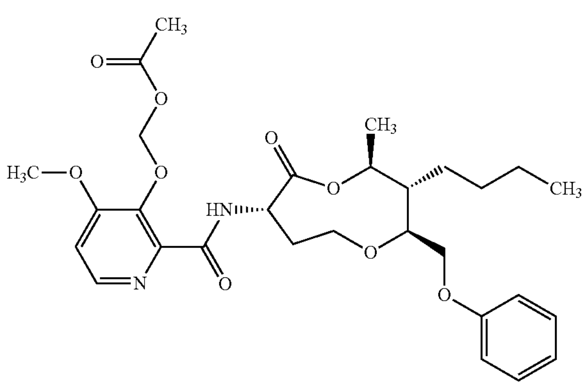 | Example 10 | Colorless Oil |

TABLE 1-continued

Compound Structure, Appearance, and Preparation Method

| Compound Number | Structure | Prepared According to Example | Appearance |
|---|---|---|---|
| 36 | (structure) | Example 12 | White Foam |
| 37 | (structure) | Example 12 | White Foam |
| 38 | (structure) | Example 12 | White Foam |

TABLE 1-continued

Compound Structure, Appearance, and Preparation Method

| Compound Number | Structure | Prepared According to Example | Appearance |
|---|---|---|---|
| 39 | 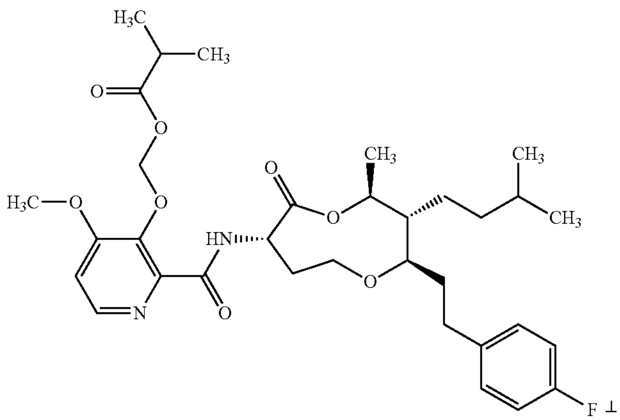 [SMILES: COc1ccnc(C(=O)N[C@H]2CCO[C@H](CCc3ccc(F)cc3)[C@@H](CCC(C)C)[C@H](C)OC2=O)c1OCOC(=O)C(C)C] | Example 12 | White Powder |
| 40 | 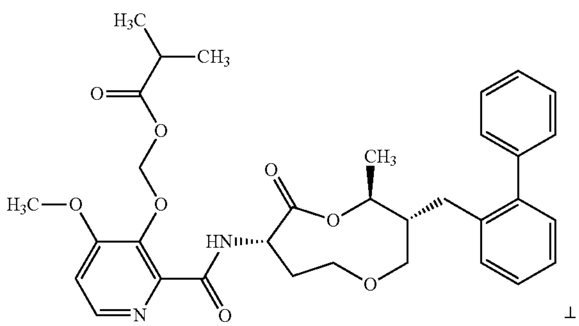 [SMILES: COc1ccnc(C(=O)N[C@H]2CCOC[C@@H](Cc3ccccc3-c3ccccc3)[C@H](C)OC2=O)c1OCOC(=O)C(C)C] | Example 12 | White Powder |
| 41 | 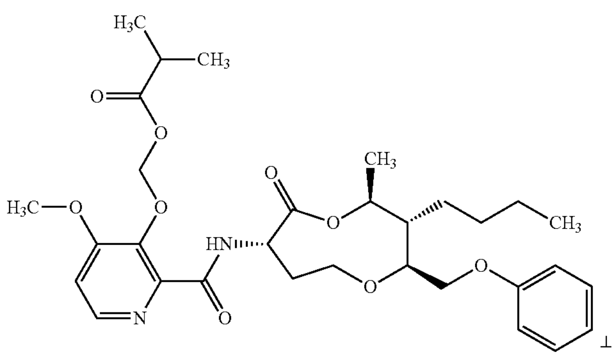 [SMILES: CCCC[C@H]1[C@H](C)OC(=O)[C@@H](NC(=O)c2nccc(OC)c2OCOC(=O)C(C)C)CCO[C@@H]1COc1ccccc1] | Example 12 | White Solid |
| 42 | 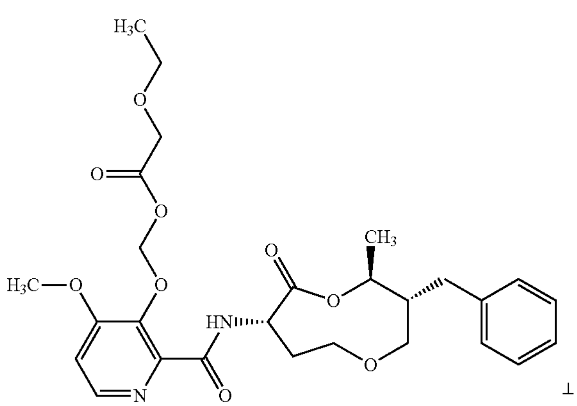 [SMILES: CCOCC(=O)OCOc1c(OC)ccnc1C(=O)N[C@H]1CCOC[C@@H](Cc2ccccc2)[C@H](C)OC1=O] | Example 13 | White Foam |

TABLE 1-continued
Compound Structure, Appearance, and Preparation Method
| Compound Number | Structure | Prepared According to Example | Appearance |
|---|---|---|---|
| 43 | 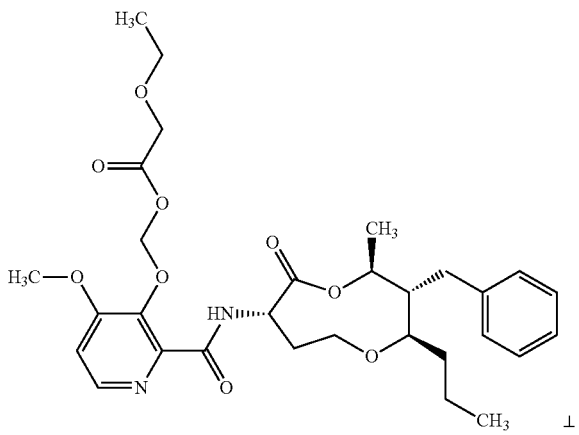 [SMILES: CCC[C@H]1OCC[C@H](NC(=O)c2nccc(OC)c2OCOC(=O)COCC)C(=O)O[C@@H](C)[C@@H]1Cc1ccccc1] | Example 13 | White Foam |
| 44 | 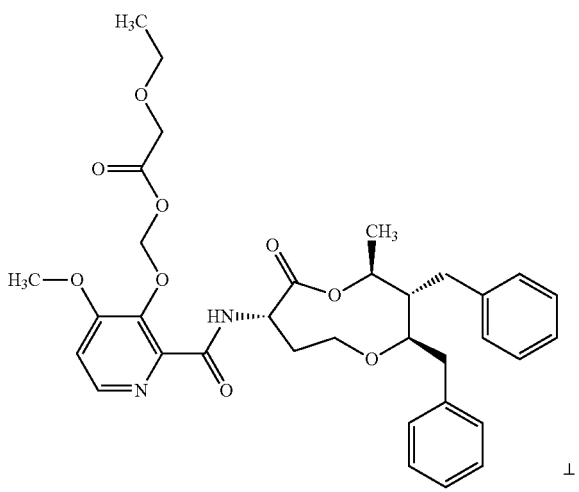 [SMILES: CCOCC(=O)OCOc1c(OC)ccnc1C(=O)N[C@H]1CCO[C@H](Cc2ccccc2)[C@@H](Cc2ccccc2)[C@H](C)OC1=O] | Example 13 | White Foam |
| 45 | 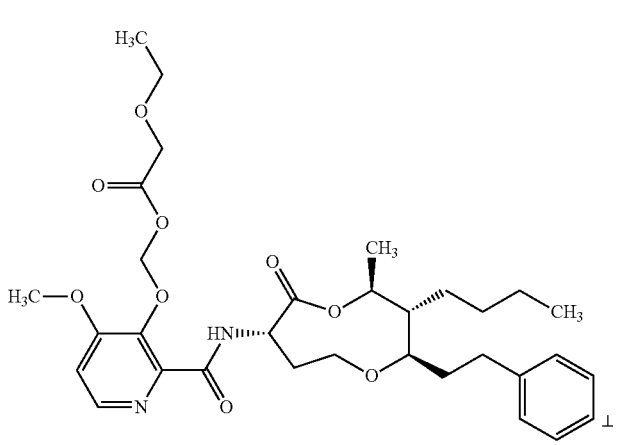 [SMILES: CCCC[C@H]1[C@H](C)OC(=O)[C@@H](NC(=O)c2nccc(OC)c2OCOC(=O)COCC)CCO[C@@H]1CCc1ccccc1] | Example 13 | White Foam |

TABLE 1-continued
Compound Structure, Appearance, and Preparation Method
| Compound Number | Structure | Prepared According to Example | Appearance |
|---|---|---|---|
| 46 | 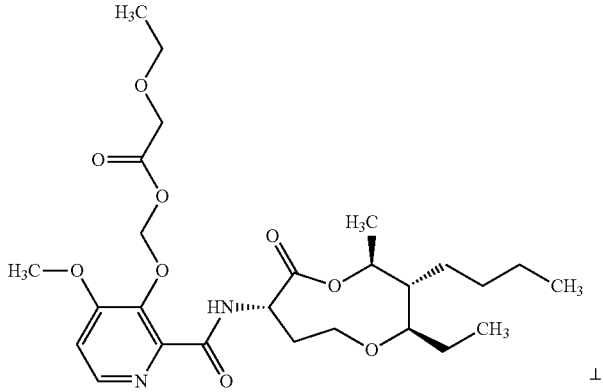 [SMILES: CCCC[C@H]1[C@H](C)OC(=O)[C@@H](NC(=O)c2nccc(OC)c2OCOC(=O)COCC)CCO[C@@H]1CC] | Example 13 | Colorless Oil |
| 47 | 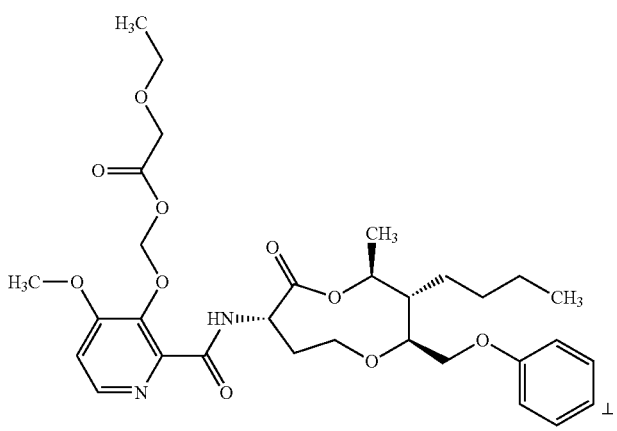 [SMILES: CCCC[C@H]1[C@H](C)OC(=O)[C@@H](NC(=O)c2nccc(OC)c2OCOC(=O)COCC)CCO[C@@H]1COc1ccccc1] | Example 13 | Colorless Oil |
| 48 | 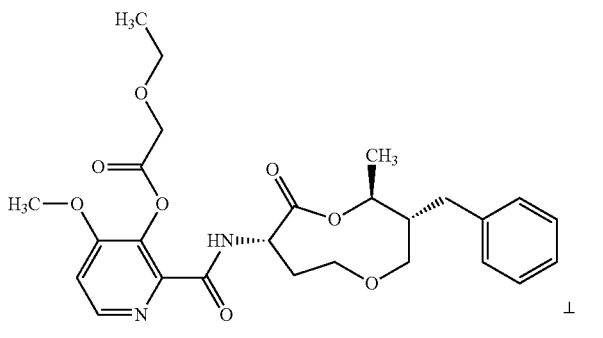 [SMILES: CCOCC(=O)Oc1c(OC)ccnc1C(=O)N[C@H]1CCOC[C@@H](Cc2ccccc2)[C@H](C)OC1=O] | Example 13 | White Foam |
| 49 | 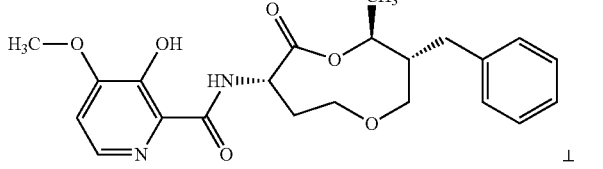 | Example 9, Step 2 | White Foam |

TABLE 1-continued

Compound Structure, Appearance, and Preparation Method

| Compound Number | Structure | Prepared According to Example | Appearance |
|---|---|---|---|
| 50 | 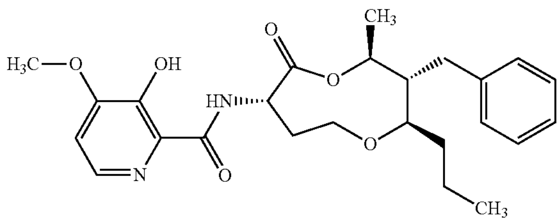 | Example 9, Step 2 | White Solid |
| 51 | 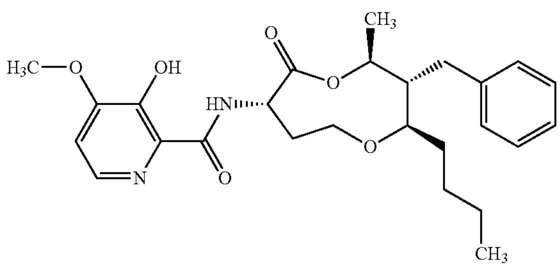 | Example 9, Step 2 | White Foam |
| 52 | 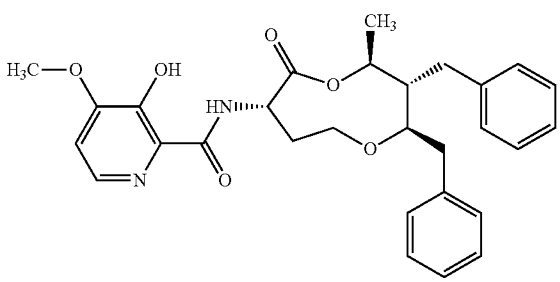 | Example 9, Step 2 | White Foam |
| 53 | 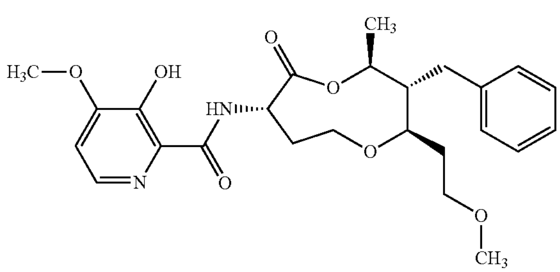 | Example 9, Step 2 | White Foam |
| 54 | 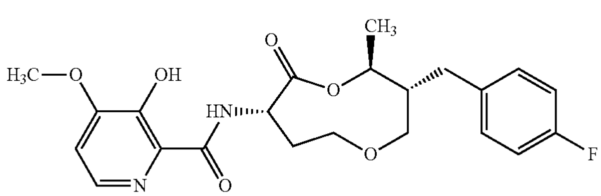 | Example 9, Step 2 | White Foam |
| 55 | 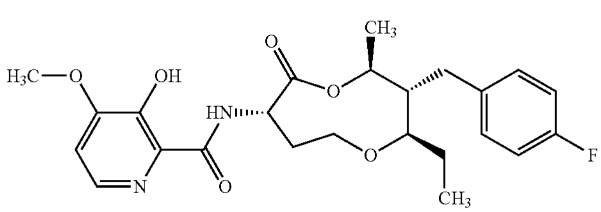 | Example 9, Step 2 | White Solid |

TABLE 1-continued

Compound Structure, Appearance, and Preparation Method

| Compound Number | Structure | Prepared According to Example | Appearance |
|---|---|---|---|
| 56 | 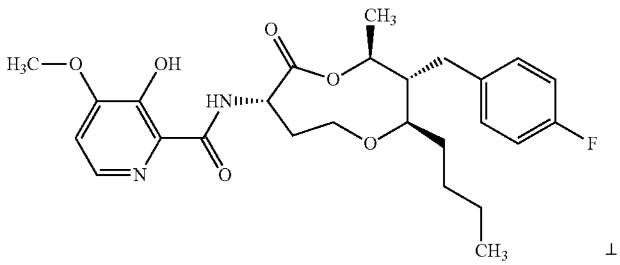 [SMILES: CCCC[C@H]1OCC[C@H](NC(=O)c2nccc(OC)c2O)C(=O)O[C@@H](C)[C@@H]1Cc1ccc(F)cc1] | Example 9, Step 2 | White Solid |
| 57 | 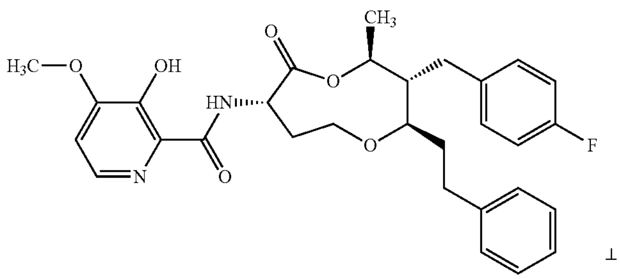 [SMILES: COc1ccnc(C(=O)N[C@H]2CCO[C@H](CCc3ccccc3)[C@@H](Cc3ccc(F)cc3)[C@H](C)OC2=O)c1O] | Example 9, Step 2 | White Solid |
| 58 | 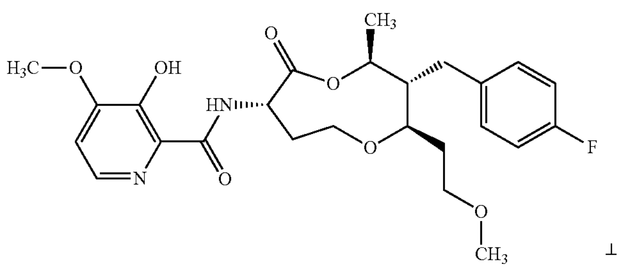 [SMILES: COCC[C@H]1OCC[C@H](NC(=O)c2nccc(OC)c2O)C(=O)O[C@@H](C)[C@@H]1Cc1ccc(F)cc1] | Example 9, Step 2 | White Foam |
| 59 | 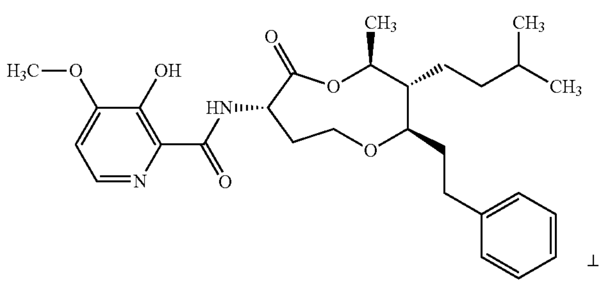 [SMILES: COc1ccnc(C(=O)N[C@H]2CCO[C@H](CCc3ccccc3)[C@@H](CCC(C)C)[C@H](C)OC2=O)c1O] | Example 9, Step 2 | White Solid |
| 60 | 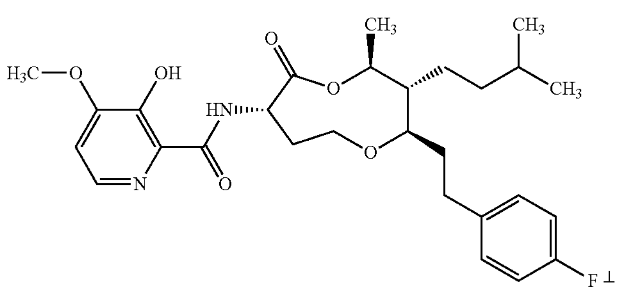 [SMILES: COc1ccnc(C(=O)N[C@H]2CCO[C@H](CCc3ccc(F)cc3)[C@@H](CCC(C)C)[C@H](C)OC2=O)c1O] | Example 9, Step 2 | White Solid |

TABLE 1-continued

Compound Structure, Appearance, and Preparation Method

| Compound Number | Structure | Prepared According to Example | Appearance |
|---|---|---|---|
| 61 | 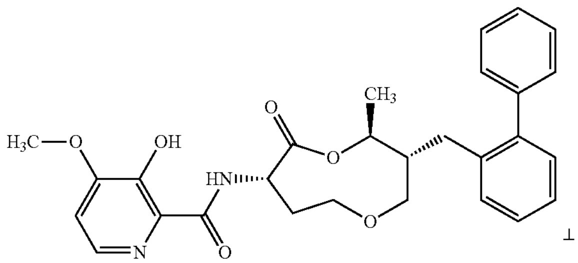 [SMILES: COc1ccnc(C(=O)N[C@H]2CCOC[C@@H](Cc3ccccc3-c3ccccc3)[C@H](C)OC2=O)c1O] | Example 9, Step 2 | White Powder |
| 62 | 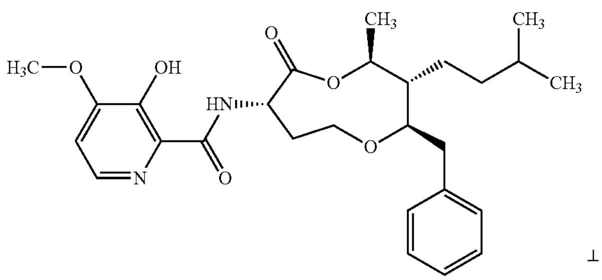 [SMILES: COc1ccnc(C(=O)N[C@H]2CCO[C@H](Cc3ccccc3)[C@@H](CCC(C)C)[C@H](C)OC2=O)c1O] | Example 9, Step 2 | White Solid |
| 63 | 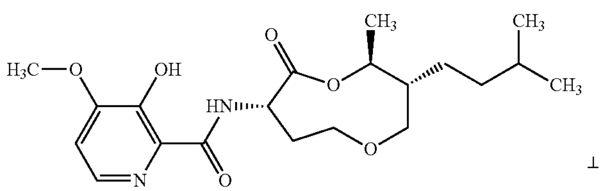 [SMILES: COc1ccnc(C(=O)N[C@H]2CCOC[C@@H](CCC(C)C)[C@H](C)OC2=O)c1O] | Example 9, Step 2 | Sticky White Solid |
| 64 | 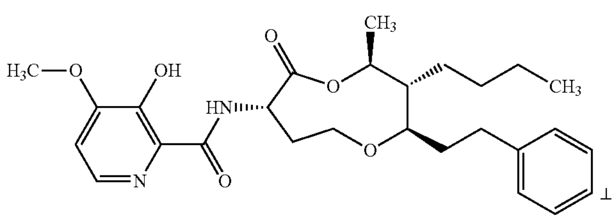 [SMILES: CCCC[C@H]1[C@H](C)OC(=O)[C@@H](NC(=O)c2nccc(OC)c2O)CCO[C@@H]1CCc1ccccc1] | Example 9, Step 2 | White Solid |
| 65 | 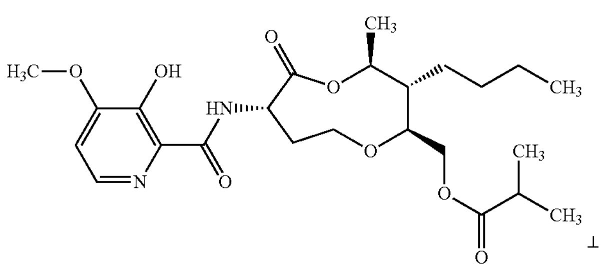 [SMILES: CCCC[C@H]1[C@H](C)OC(=O)[C@@H](NC(=O)c2nccc(OC)c2O)CCO[C@@H]1COC(=O)C(C)C] | Example 9, Step 2 | White Foam |
| 66 | 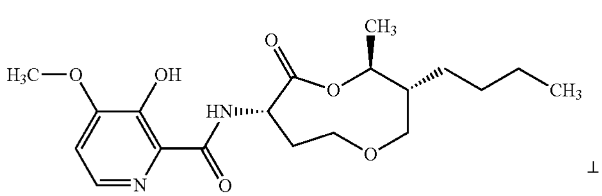 [SMILES: CCCC[C@@H]1COCC[C@H](NC(=O)c2nccc(OC)c2O)C(=O)O[C@H]1C] | Example 9, Step 2 | Colorless Oil |

TABLE 1-continued

Compound Structure, Appearance, and Preparation Method

| Compound Number | Structure | Prepared According to Example | Appearance |
|---|---|---|---|
| 67 | 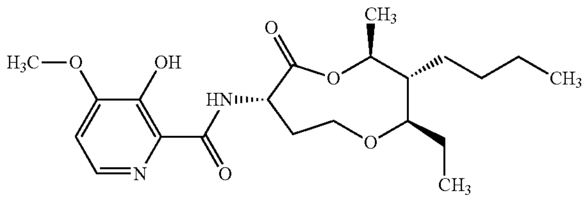 | Example 9, Step 2 | Colorless Solid |
| 68 | 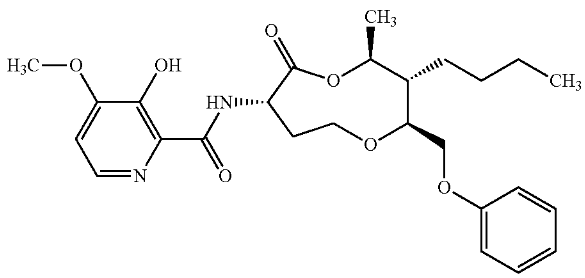 | Example 9, Step 2 | White Solid |
| 69 | 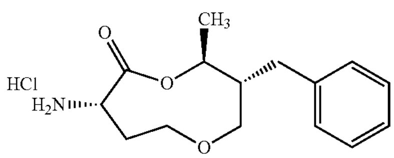 | Example 9, Step 1 | White Solid |
| 70 | 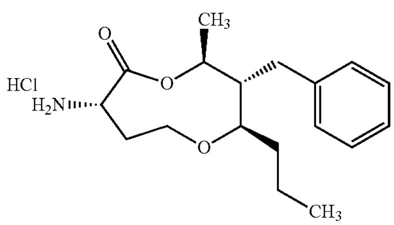 | Example 9, Step 1 | White Solid |
| 71 | 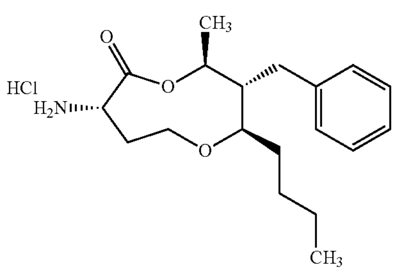 | Example 9, Step 1 | White Solid |
| 72 | 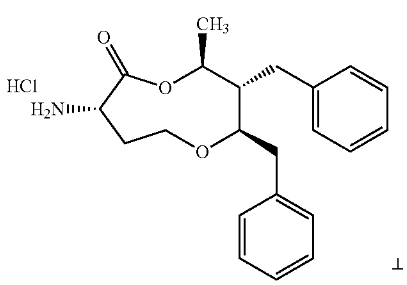 [SMILES: Cl ; C[C@@H]1OC(=O)[C@@H](N)CCO[C@H](Cc2ccccc2)[C@H]1Cc1ccccc1] | Example 9, Step 1 | White Solid |

TABLE 1-continued

Compound Structure, Appearance, and Preparation Method

| Compound Number | Structure | Prepared According to Example | Appearance |
|---|---|---|---|
| 73 | 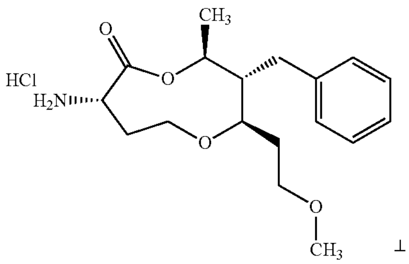 [SMILES: Cl ; COCC[C@H]1OCC[C@H](N)C(=O)O[C@@H](C)[C@@H]1Cc1ccccc1] | Example 9, Step 1 | White Foam |
| 74 | 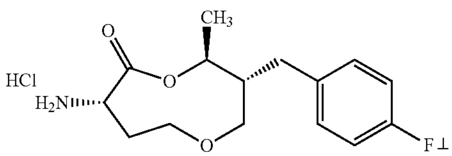 [SMILES: Cl ; C[C@@H]1OC(=O)[C@@H](N)CCOC[C@H]1Cc1ccc(F)cc1] | Example 9, Step 1 | White Solid |
| 75 | 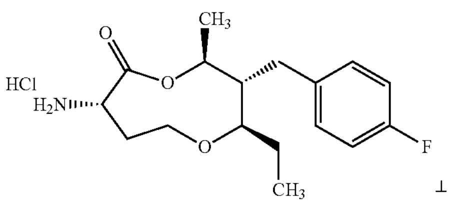 [SMILES: Cl ; CC[C@H]1OCC[C@H](N)C(=O)O[C@@H](C)[C@@H]1Cc1ccc(F)cc1] | Example 9, Step 1 | White Solid |
| 76 | 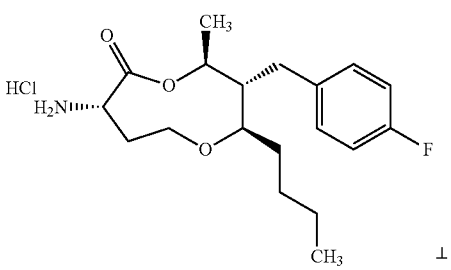 [SMILES: Cl ; CCCC[C@H]1OCC[C@H](N)C(=O)O[C@@H](C)[C@@H]1Cc1ccc(F)cc1] | Example 9, Step 1 | White Solid |
| 77 | 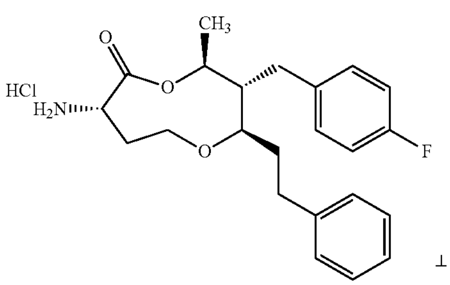 [SMILES: Cl ; C[C@@H]1OC(=O)[C@@H](N)CCO[C@H](CCc2ccccc2)[C@H]1Cc1ccc(F)cc1] | Example 9, Step 1 | White Solid |
| 78 | 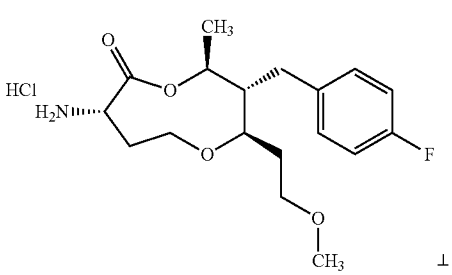 | Example 9, Step 1 | White Solid |

TABLE 1-continued
Compound Structure, Appearance, and Preparation Method
| Compound Number | Structure | Prepared According to Example | Appearance |
|---|---|---|---|
| 79 | 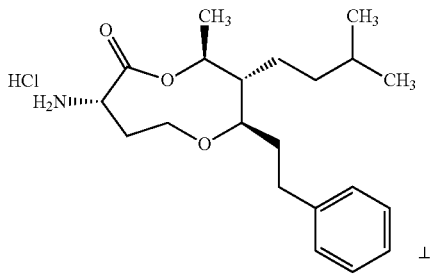 [SMILES: Cl ; CC(C)CC[C@H]1[C@H](C)OC(=O)[C@@H](N)CCO[C@@H]1CCc1ccccc1] | Example 9, Step 1 | White Powder |
| 80 | 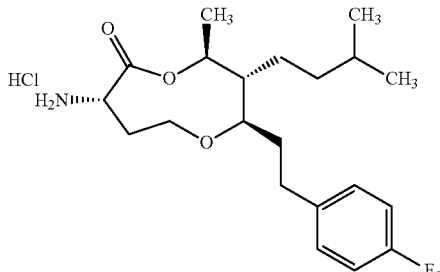 | Example 9, Step 1 | White Solid |
| 81 | 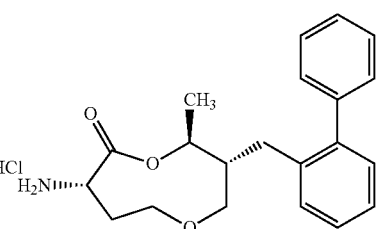 | Example 9, Step 1 | White Solid |
| 82 | 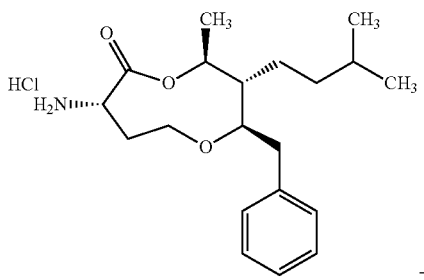 | Example 9, Step 1 | White Solid |
| 83 | 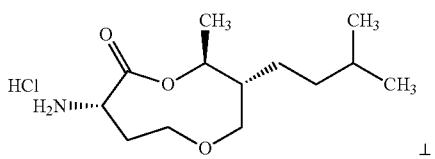 [SMILES: Cl ; CC(C)CC[C@@H]1COCC[C@H](N)C(=O)O[C@H]1C] | Example 9, Step 1 | White Solid |
| 84 | 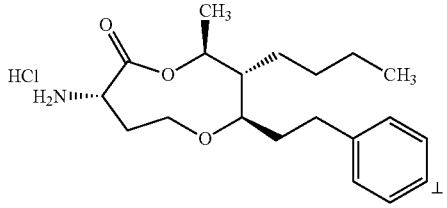 [SMILES: Cl ; CCCC[C@H]1[C@H](C)OC(=O)[C@@H](N)CCO[C@@H]1CCc1ccccc1] | Example 9, Step 1 | White Solid |

TABLE 1-continued

Compound Structure, Appearance, and Preparation Method

| Compound Number | Structure | Prepared According to Example | Appearance |
|---|---|---|---|
| 85 | 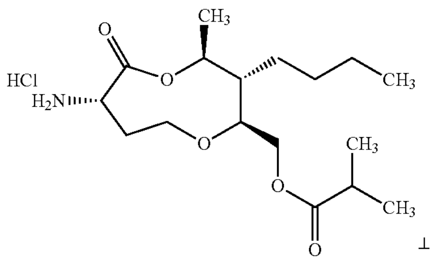 [SMILES: Cl ; CCCC[C@H]1[C@H](C)OC(=O)[C@@H](N)CCO[C@@H]1COC(=O)C(C)C] | Example 9, Step 1 | White Solid |
| 86 | 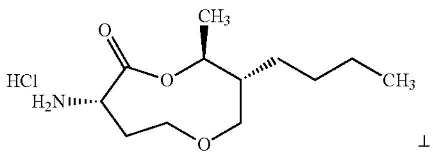 [SMILES: Cl ; CCCC[C@@H]1COCC[C@H](N)C(=O)O[C@H]1C] | Example 9, Step 1 | White Solid |
| 87 | 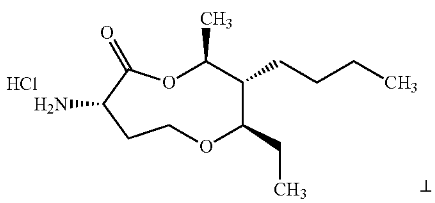 [SMILES: Cl ; CCCC[C@H]1[C@H](C)OC(=O)[C@@H](N)CCO[C@@H]1CC] | Example 9, Step 1 | White Solid |
| 88 | 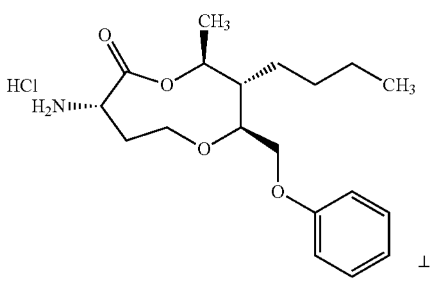 [SMILES: Cl ; CCCC[C@H]1[C@H](C)OC(=O)[C@@H](N)CCO[C@@H]1COc1ccccc1] | Example 9, Step 1 | Colorless Solid |
| 89 | 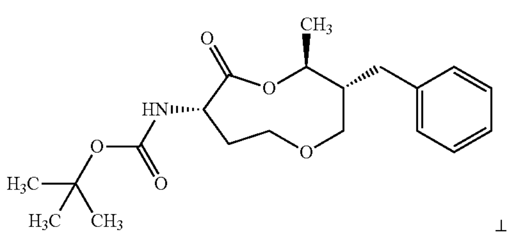 [SMILES: C[C@@H]1OC(=O)[C@@H](NC(=O)OC(C)(C)C)CCOC[C@H]1Cc1ccccc1] | Example 1 Steps 1, 3; Example 2, Step 5; Example 3, Steps 1, 2, 3; Example 6 Steps 1, 2, 3; Example 7, Step 1 | Pale Yellow Oil |
| 90 | 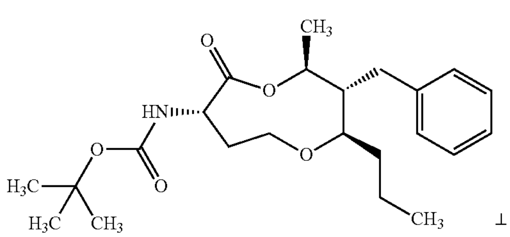 [SMILES: CCC[C@H]1OCC[C@H](NC(=O)OC(C)(C)C)C(=O)O[C@@H](C)[C@@H]1Cc1ccccc1] | Example 1 Steps 1, 3; Example 2, Steps 1, 2, 3, 4; Example 4, Step 1; Example 5, Steps 1, 2; Example 6, Steps 1, 2, 3; Example 7, Step 1 | Colorless Oil |

TABLE 1-continued

Compound Structure, Appearance, and Preparation Method

| Compound Number | Structure | Prepared According to Example | Appearance |
|---|---|---|---|
| 91 | 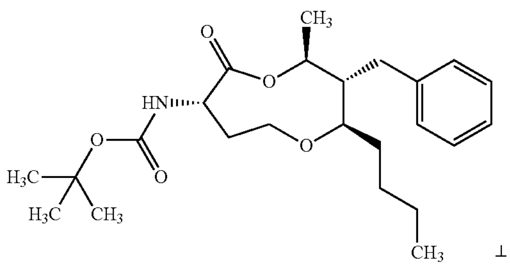 | Example 1, Steps 1, 3; Example 2, Steps 1, 2; Example 4 Steps 1, 2; Example 5, Steps 1, 2; Example 6, Steps 1, 2, 3; Example 7, Step 1 | White Foam |
| 92 | 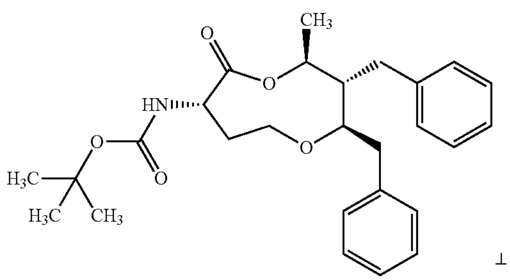 [SMILES: C[C@@H]1OC(=O)[C@@H](NC(=O)OC(C)(C)C)CCO[C@H](Cc2ccccc2)[C@H]1Cc1ccccc1] | Example 1, Steps 1, 3; Example 2, Steps 1, 2, 3, 4; Example 3, Steps 1, 2, 3; Example 6, Steps 1, 2, 3; Example 7, Step 1 | White Foam |
| 93 | 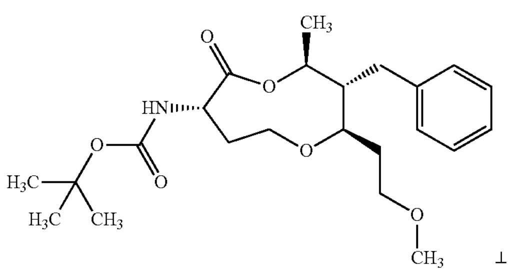 [SMILES: COCC[C@H]1OCC[C@H](NC(=O)OC(C)(C)C)C(=O)O[C@@H](C)[C@@H]1Cc1ccccc1] | Example 1 Steps 1, 3; Example 2, Steps 1, 2; Example 4, Steps 1, 3, 5; Example 5, Steps 1, 2; Example 6, Steps 1, 2, 3; Example 7, Step 1 | White Foam |
| 94 | 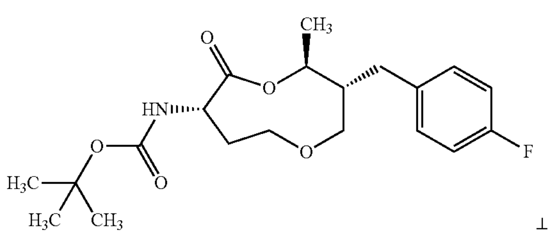 [SMILES: C[C@@H]1OC(=O)[C@@H](NC(=O)OC(C)(C)C)CCOC[C@H]1Cc1ccc(F)cc1] | Example 1, Steps 1, 3; Example 2, Step 5; Example 3, Steps 1, 2, 3; Example 6, Steps 1, 2, 3; Example 7, Step 1 | Pale Yellow Oil |
| 95 | 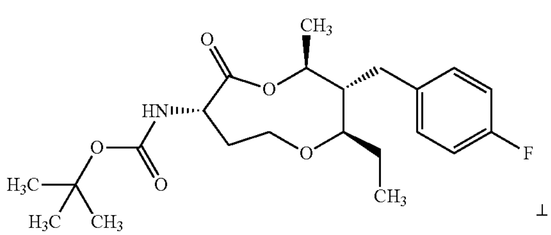 [SMILES: CC[C@H]1OCC[C@H](NC(=O)OC(C)(C)C)C(=O)O[C@@H](C)[C@@H]1Cc1ccc(F)cc1] | Example 1, Steps 1, 3; Example 2, Steps 1, 2; Example 4, Step 1; Example 5 Steps 1, 2; Example 6, Steps 1, 2, 3; Example 7, Step 1 | White Foam |

TABLE 1-continued

Compound Structure, Appearance, and Preparation Method

| Compound Number | Structure | Prepared According to Example | Appearance |
|---|---|---|---|
| 96 | 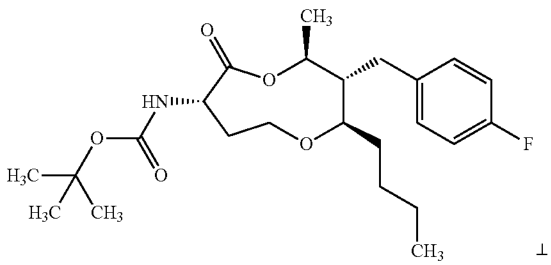 | Example 1, Steps 1, 3; Example 2, Steps 1, 2; Example 4, Steps 1, 2; Example 5, Steps 1, 2; Example 6, Steps 1, 2, 3; Example 7, Step 1 | White Foam |
| 97 | 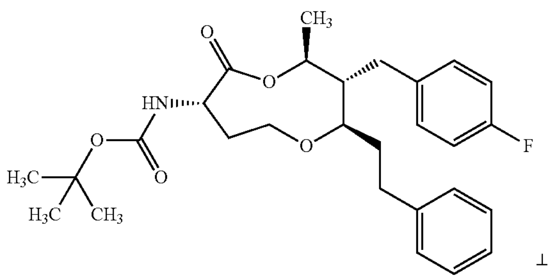 [SMILES: C[C@@H]1OC(=O)[C@@H](NC(=O)OC(C)(C)C)CCO[C@H](CCc2ccccc2)[C@H]1Cc1ccc(F)cc1] | Example 1, Steps 1, 3; Example 2, Steps 1, 2; Example 4, Steps 1, 2; Example 5, Steps 1, 2; Example 6, Steps 1, 2, 3; Example 7, Step 1 | White Foam |
| 98 | 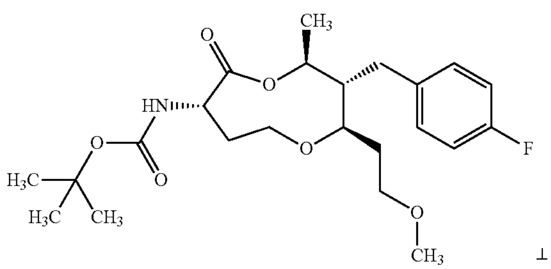 [SMILES: COCC[C@H]1OCC[C@H](NC(=O)OC(C)(C)C)C(=O)O[C@@H](C)[C@@H]1Cc1ccc(F)cc1] | Example 1, Steps 1, 3; Example 2, Steps 1, 2; Example 4, Steps 1, 3, 5; Example 5, Steps 1, 2; Example 6, Steps 1, 2, 3; Example 7, Step 1 | White Foam |
| 99 | 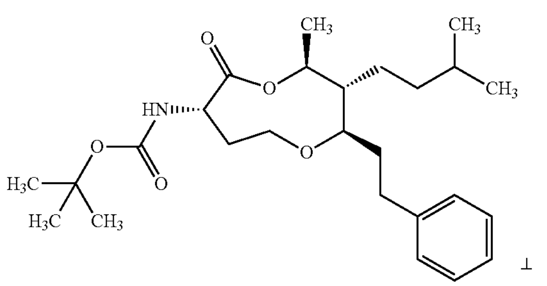 [SMILES: CC(C)CC[C@H]1[C@H](C)OC(=O)[C@@H](NC(=O)OC(C)(C)C)CCO[C@@H]1CCc1ccccc1] | Example 1, Steps 1, 2, 3; Example 2, Steps 1, 2; Example 4, Steps 1, 2; Example 5, Steps 1, 2; Example 6, Steps 1, 2, 3; Example 7, Step 1 | Sticky White Solid |
| 100 | 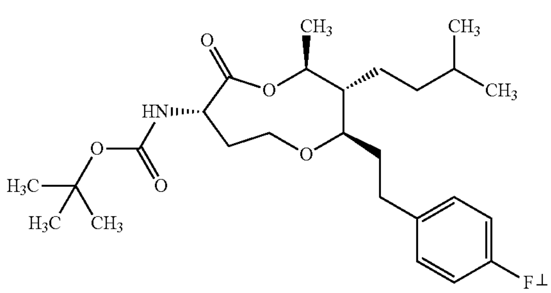 [SMILES: CC(C)CC[C@H]1[C@H](C)OC(=O)[C@@H](NC(=O)OC(C)(C)C)CCO[C@@H]1CCc1ccc(F)cc1] | Example 1, Steps 1, 2, 3; Example 2, Steps 1, 2; Example 4, Steps 1, 2; Example 5, Steps 1, 2; Example 6, Steps 1, 2, 3; Example 7, Step 1 | White Powder |

TABLE 1-continued

Compound Structure, Appearance, and Preparation Method

| Compound Number | Structure | Prepared According to Example | Appearance |
|---|---|---|---|
| 101 | 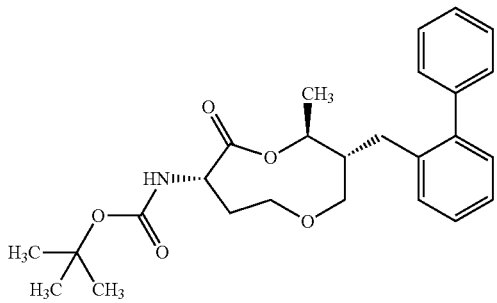 | Example 1, Step 1; Example 2, Step 5b; Example 3, Steps 1b, 2, 3; Example 6, Steps 1, 3; Example 7, Step 1 | Sticky Solid |
| 102 | 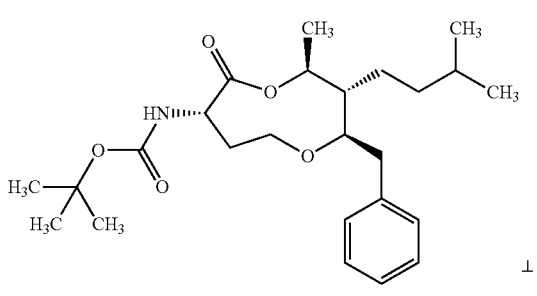 [SMILES: CC(C)CC[C@H]1[C@H](C)OC(=O)[C@@H](NC(=O)OC(C)(C)C)CCO[C@@H]1Cc1ccccc1] | Example 1, Steps 1, 2, 3; Example 2, Steps 1, 2, 3, 4; Example 3, Steps 1a, 2, 3; Example 6, Steps 1, 2, 3; Example 7, Step 1 | White Solid |
| 103 | 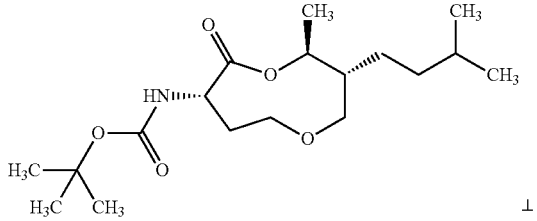 [SMILES: CC(C)CC[C@@H]1COCC[C@H](NC(=O)OC(C)(C)C)C(=O)O[C@H]1C] | Example 1, Steps 1, 2; Example 2, Step 5b; Example 3, Steps 1b, 2, 3; Example 6, Steps 1, 3; Example 7, Step 1 | White Solid |
| 104 | 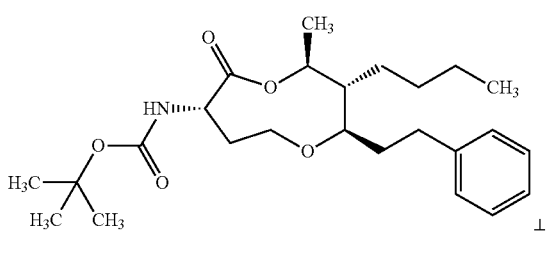 [SMILES: CCCC[C@H]1[C@H](C)OC(=O)[C@@H](NC(=O)OC(C)(C)C)CCO[C@@H]1CCc1ccccc1] | Example 1, Steps 1, 2, 3; Example 2, Steps 1, 2; Example 4, Steps 1, 2; Example 5, Steps 1, 2; Example 6, Steps 1, 2, 3; Example 7, Step 1 | Colorless Oil |
| 105 | 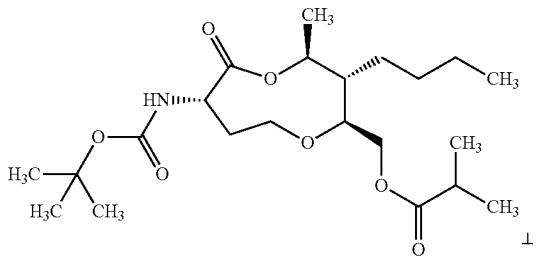 [SMILES: CCCC[C@H]1[C@H](C)OC(=O)[C@@H](NC(=O)OC(C)(C)C)CCO[C@@H]1COC(=O)C(C)C] | Example 1, Steps 1, 2, 3; Example 2, Steps 1, 2; Example 4, Steps 1, 4, 5; Example 5, Steps 1, 2; Example 6, Steps 1, 2, 3; Example 7, Step 1; Example 8, Steps 1, 2 | Colorless Oil |

TABLE 1-continued

Compound Structure, Appearance, and Preparation Method

| Compound Number | Structure | Prepared According to Example | Appearance |
|---|---|---|---|
| 106 | 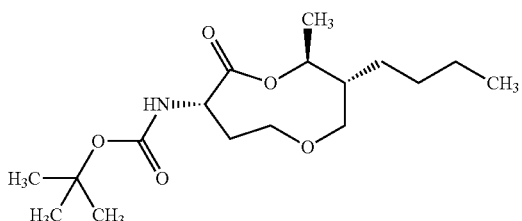 | Example 1, Steps 1, 2, 3; Example 2, Step 5; Example 3, Steps 1, 2, 3; Example 6, Steps 1, 2, 3; Example 7, Step 1 | White Solid |
| 107 | 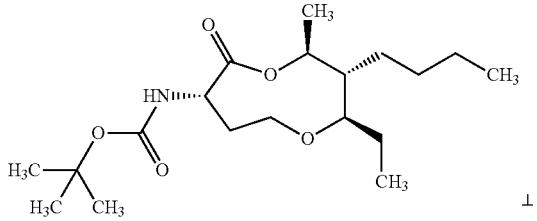 [SMILES: CCCC[C@H]1[C@H](C)OC(=O)[C@@H](NC(=O)OC(C)(C)C)CCO[C@@H]1CC] | Example 1, Steps 1, 2, 3; Example 2, Steps 1, 2, 3, 4; Example 4, Step 1; Example 5, Steps 1, 2; Example 6, Steps, 1, 2, 3; Example 7, Step 1 | Colorless Oil |
| 108 | 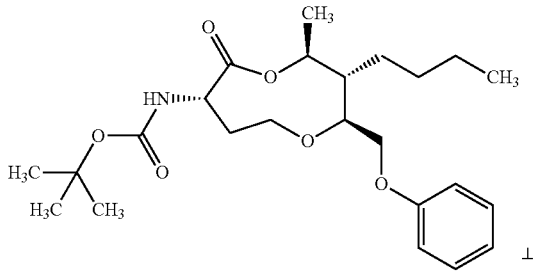 [SMILES: CCCC[C@H]1[C@H](C)OC(=O)[C@@H](NC(=O)OC(C)(C)C)CCO[C@@H]1COc1ccccc1] | Example 1, Steps 1, 2, 3; Example 2, Steps 1, 2, 3, 4; Example 4, Steps 1, 4, 6; Example 5, Steps 1, 2; Example 6, Steps 1, 2, 3; Example 7, Step 1 | Colorless Oil |

TABLE 2

Analytical Data

| Compound Number | MP (° C.) | IR (cm$^{-1}$) | MASS | NMR ($^1$H, $^{13}$H, $^{19}$F) |
|---|---|---|---|---|
| 1 | — | (Thin Film) 3378, 3025, 2930, 1770, 1740, 1677, 1506 | HRMS-ESI (m/z) [M + H]$^+$ calcd for C$_{24}$H$_{29}$N$_2$O$_7$, 457.1969; found, 457.1978 | $^1$H NMR (400 MHz, CDCl$_3$) δ 8.77 (d, J = 7.3 Hz, 1H), 8.34 (d, J = 5.4 Hz, 1H), 7.31-7.26 (m, 2H), 7.26-7.22 (m, 2H), 7.24-7.15 (m, 1H), 7.00 (d, J = 5.4 Hz, 1H), 5.18 (qd, J = 6.6, 3.6 Hz, 1H), 4.67 (td, J = 7.8, 5.4 Hz, 1H), 3.92 (ddd, J = 11.3, 7.4, 2.6 Hz, 1H), 3.89 (s, 3H), 3.63 (dd, J = 10.7, 4.2 Hz, 1H), 3.49 (dd, J = 10.8, 2.6 Hz, 1H), 3.43 (ddd, J = 11.3, 7.6, 2.5 Hz, 1H), 2.87 (dd, J = 13.5, 7.7 Hz, 1H), 2.77 (dd, J = 13.5, 8.4 Hz, 1H), 2.51-2.41 (m, 1H), 2.40 (s, 3H), 1.88 (dtd, J = 14.5, 7.9, 2.8 Hz, 1H), 1.83-1.76 (m, 1H), 1.24 (d, J = 6.6 Hz, 3H) |
| 2 | — | (Thin Film) 3379, 2934, 2871, 1770, 1743, 1676, 1506 | HRMS-ESI (m/z) [M + H]$^+$ calcd for C$_{28}$H$_{37}$N$_2$O$_7$, 513.2595; found, 513.2609 | $^1$H NMR (400 MHz, CDCl$_3$) δ 8.62 (d, J = 8.2 Hz, 1H), 8.32 (d, J = 5.4 Hz, 1H), 7.34-7.25 (m, 2H), 7.23-7.12 (m, 3H), 6.99 (d, J = 5.5 Hz, 1H), 5.17 (dq, J = 9.5, 6.5 Hz, 1H), 4.60 (dt, J = 10.0, 7.7 Hz, 1H), 3.88 (s, 3H), 3.61 (dd, J = 11.1, 9.4 Hz, 1H), 3.55-3.43 (m, 2H), 2.61 (dd, J = 15.8, 3.5 Hz, 1H), 2.51 (dd, J = 15.8, 6.6 Hz, 1H), 2.39 (s, 3H), 2.21 (dddd, J = 13.3, 10.0, 6.6, 3.4 Hz, 1H), 1.75-1.61 |

TABLE 2-continued

Analytical Data

| Compound Number | MP (° C.) | IR (cm$^{-1}$) | MASS | NMR ($^1$H, $^{13}$H, $^{19}$F) |
|---|---|---|---|---|
| | | | | (m, 1H), 1.61-1.53 (m5 2H)5 1.49-1.39 (m, 1H), 1.27 (d, J = 6.5 Hz, 3H), 1.37-1.19 (m, 3H), 0.87 (t, J = 7.1 Hz, 3H), 2.44-2.32 (m, 1H) |
| 3 | — | (Thin Film) 3378, 2936, 1770, 1744, 1677, 1507 | HRMS-ESI (m/z) [M + H]$^+$ calcd for C$_{31}$H$_{35}$N$_2$O$_7$, 547.2439; found, 547.2448 | $^1$H NMR (400 MHz, CDCl$_3$) δ 8.57 (d, J = 7.9 Hz, 1H), 8.29 (d, J = 5.4 Hz, 1H), 7.35-7.24 (m, 3H), 7.26-7.20 (m, 4H), 7.19-7.15 (m, 3H), 6.96 (d, J = 5.5 Hz, 1H), 5.21 (dq, J = 9.6, 6.5 Hz, 1H), 4.61 (ddd, J = 9.6, 8.1, 7.2 Hz, 1H), 3.99 (td, J = 10.6, 2.5 Hz, 1H), 3.86 (s, 3H), 3.62 (t, J = 9.9 Hz, 1H), 3.41 (ddd, J = 9.6, 4.7, 2.0 Hz, 1H), 3.00 (dd, J = 15.7, 2.5 Hz, 1H), 2.85 (dd, J = 15.7, 10.9 Hz, 1H), 2.75 (dd, J = 15.9, 3.8 Hz, 1H), 2.65 (dd, J = 15.8, 6.2 Hz, 1H), 2.37 (s, 3H), 2.42-2.32 (m, 1H), 2.27 (ddd, J = 14.2, 7.3, 4.9 Hz, 1H), 1.64-1.52 (m, 1H), 1.35 (d, J = 6.5 Hz, 3H) |
| 4 | — | (Thin Film) 3377, 2937, 2876, 1770, 1744, 1676, 1507 | HRMS-ESI (m/z) [M + H]$^+$ calcd for C$_{27}$H$_{35}$N$_2$O$_8$, 515.2388; found, 515.2390 | $^1$H NMR (400 MHz, CDCl$_3$) δ 8.63 (d, J = 8.1 Hz, 1H), 8.33 (d, J = 5.4 Hz, 1H), 7.33-7.24 (m, 2H), 7.23-7.16 (m, 3H), 6.99 (d, J = 5.5 Hz, 1H), 5.15 (dq, J = 9.5, 6.5 Hz, 1H), 4.61 (dt, J = 10.0, 7.7 Hz, 1H), 3.90 (s, 3H), 3.73-3.60 (m, 2H), 3.53-3.47 (m, 1H), 3.47-3.33 (m, 2H), 3.31 (s, 3H), 2.61 (dd, J = 15.9, 3.5 Hz, 1H), 2.51 (dd, J = 15.9, 6.4 Hz, 1H), 2.44-2.40 (m, 1H), 2.39 (s, 3H), 2.26 (tdd, J = 10.0, 6.3, 3.4 Hz, 1H), 2.02-1.80 (m, 2H), 1.75-1.66 (m, 1H), 1.28 (d, J = 6.5 Hz, 3H) |
| 5 | — | — | HRMS-ESI (m/z) [M + H]$^+$ calcd for C$_{24}$H$_{28}$FN$_2$O$_7$, 475.1875; found, 475.1887 | $^1$H NMR (400 MHz, CDCl$_3$) δ 8.81-8.71 (m, 1H), 8.35 (d, J = 5.4 Hz, 1H), 7.20 (dd, J = 8.5, 5.5 Hz, 2H), 7.01 (d, J = 5.5 Hz, 1H), 6.97 (t, J = 8.7 Hz, 2H), 5.16 (qd, J = 6.7, 3.2 Hz, 1H), 4.67 (td, J = 7.8, 5.3 Hz, 1H), 3.98-3.91 (m, 1H), 3.90 (s, 3H), 3.62 (dd, J = 10.7, 3.9 Hz, 1H), 3.49 (dd, J = 10.7, 2.4 Hz, 1H), 3.42 (ddd, J = 11.2, 7.6, 2.5 Hz, 1H), 2.85 (dd, J = 13.6, 7.9 Hz, 1H), 2.77 (dd, J = 13.6, 8.4 Hz, 1H), 2.52-2.41 (m, 1H), 2.40 (s, 3H), 1.88 (dtd, J = 15.8, 9.3, 8.6, 3.5 Hz, 1H), 1.72 (ttd, J = 7.8, 3.7, 2.3 Hz, 1H), 1.24 (d, J = 6.7 Hz, 3H)<br>$^{19}$F NMR (376 MHz, CDCl$_3$) δ −117.23 |
| 6 | — | — | HRMS-ESI (m/z) [M + H]$^+$ calcd for C$_{28}$H$_{36}$FN$_2$O$_7$, 531.2501, found, 531.2501 | $^1$H NMR (400 MHz, CDCl$_3$) δ 8.62 (d, J = 8.9 Hz, 1H), 8.33 (d, J = 5.4 Hz, 1H), 7.13 (dd, J = 8.5, 5.4 Hz, 2H), 7.03-6.95 (m, 3H), 5.15 (dq, J = 9.4, 6.5 Hz, 1H), 4.60 (dt, J = 10.0, 7.7 Hz, 1H), 3.90 (s, 3H), 3.61 (dd, J = 11.1, 9.4 Hz, 1H), 3.55-3.40 (m, 2H), 2.58 (dd, J = 15.9, 3.5 Hz, 1H), 2.50 (dd, J = 15.8, 6.5 Hz, 1H), 2.39 (s, 3H), 2.44-2.32 (m, 1H), 2.21-2.09 (m, 1H), 1.74-1.62 (m, 1H), 1.62-1.48 (m, 2H), 1.38-1.19 (m, 4H), 1.26 (d, J = 6.4 Hz, 3H), 0.88 (t, J = 7.0 Hz, 3H)<br>$^{19}$F NMR (376 MHz, CDCl$_3$) δ −116.89 |
| 7 | — | — | HRMS-ESI (m/z) [M + H]$^+$ calcd for C$_{32}$H$_{36}$FN$_2$O$_7$, 579.2501; found, 579.2495 | $^1$H NMR (400 MHz, CDCl$_3$) δ 8.64 (d, J = 7.8 Hz, 1H), 8.33 (d, J = 5.4 Hz, 1H), 7.31-7.23 (m, 2H), 7.19 (t, J = 7.3 Hz, 1H), 7.13 (d, J = 8.0 Hz, 2H), 7.03-6.97 (m, 3H), 6.91 (t, J = 8.6 Hz, 2H), 5.13 (dq, J = 9.5, 6.4 Hz, 1H), 4.62 (dt, J = 10.1, 7.7 Hz, 1H), 3.89 (s, 3H), 3.71-3.57 (m, 2H), 3.52 (td, J = 10.7, 2.3 Hz, 1H), 2.78 (ddd, J = 13.7, 8.9, 4.6 Hz, 1H), 2.62-2.49 (m, 2H), 2.51-2.38 (m, 2H), 2.39 (s, 3H), 2.22-2.10 (m, 1H), 2.01-1.66 (m, 3H), 1.27 (d, J = 6.5 Hz, 3H)<br>$^{19}$F NMR (376 MHz, CDCl$_3$) δ −116.76 |

TABLE 2-continued

| Compound Number | MP (° C.) | IR (cm$^{-1}$) | MASS | NMR ($^1$H, $^{13}$H, $^{19}$F) |
|---|---|---|---|---|
| 8 | — | — | HRMS-ESI (m/z) [M + H]$^+$ calcd for C$_{27}$H$_{34}$FN$_2$O$_8$, 533.2294; found, 533.2290 | $^1$H NMR (400 MHz, CDCl$_3$) δ 8.63 (t, J = 4.8 Hz, 1H), 8.33 (d, J = 5.4 Hz, 1H), 7.15 (dd, J = 8.5, 5.4 Hz, 2H), 7.02-6.92 (m, 3H), 5.13 (dq, J = 9.5, 6.5 Hz, 1H), 4.61 (dt, J = 10.0, 7.7 Hz, 1H), 3.89 (s, 3H), 3.74-3.58 (m, 2H), 3.54-3.35 (m, 3H), 3.31 (s, 3H), 2.58 (dd, J = 15.8, 3.7 Hz, 1H), 2.50 (dd, J = 15.9, 6.3 Hz, 1H), 2.45-2.34 (m, 1H), 2.39 (s, 3H), 2.27-2.13 (m, 1H), 1.99-1.80 (m, 2H), 1.78-1.67 (m, 1H), 1.27 (d, J = 6.5 Hz, 3H) $^{19}$F NMR (376 MHz, CDCl$_3$) δ −116.85 |
| 9 | 70-74 | — | HRMS-ESI (m/z) [M + H]$^+$ calcd for C$_{30}$H$_{41}$N$_2$O$_7$, 541.2908; found, 541.2910 | $^1$H NMR (400 MHz, CDCl$_3$) δ 8.64 (d, J = 8.3 Hz, 1H), 8.34 (d, J = 5.4 Hz, 1H), 7.33-7.24 (m, 2H), 7.23-7.14 (m, 3H), 7.00 (d, J = 5.4 Hz, 1H), 5.08 (dq, J = 9.6, 6.4 Hz, 1H), 4.68-4.56 (m, 1H), 3.90 (s, 3H), 3.66-3.49 (m, 3H), 2.82 (ddd, J = 13.6, 8.9, 4.7 Hz, 1H), 2.64-2.52 (m, 1H), 2.47-2.36 (m, 4H), 1.90-1.66 (m, 4H), 1.36-1.18 (m, 6H), 1.01-0.89 (m, 2H), 0.82 (d, J = 6.6 Hz, 3H), 0.79 (d, J = 6.6 Hz, 3H) |
| 10 | 76-80 | — | HRMS-ESI (m/z) [M + H]$^+$ calcd for C$_{30}$H$_{40}$FN$_2$O$_7$, 559.2814; found, 559.2825 | $^1$H NMR (400 MHz, CDCl$_3$) δ 8.63 (d, J = 8.3 Hz, 1H), 8.34 (d, J = 5.4 Hz, 1H), 7.18-7.10 (m, 2H), 7.04-6.92 (m, 3H), 5.07 (dq, J = 9.6, 6.4 Hz, 1H), 4.61 (app dt, J = 10.2, 7.8 Hz, 1H), 3.90 (s, 3H), 3.66-3.47 (m, 3H), 2.78 (ddd, J = 13.5, 8.4, 4.4 Hz, 1H), 2.62-2.50 (m, 1H), 2.47-2.34 (m, 4H), 1.89-1.69 (m, 4H), 1.39-1.27 (m, 4H), 1.25-1.13 (m, 2H), 1.02-0.84 (m, 2H), 0.82 (d, J = 6.6 Hz, 3H), 0.79 (d, J = 6.6 Hz, 3H) |
| 11 | 77-82 | — | HRMS-ESI (m/z) [M + H]$^+$ calcd for 533.2282; found, 533.2288 | $^1$H NMR (400 MHz, CDCl$_3$) δ 8.73 (d, J = 7.2 Hz, 1H), 8.34 (d, J = 5.4 Hz, 1H), 7.45-7.14 (m, 9H), 6.99 (d, J = 5.5 Hz, 1H), 4.92 (qd, J = 6.6, 4.3 Hz, 1H), 4.59 (app td, J = 7.6, 5.3 Hz, 1H), 3.89 (s, 3H), 3.80 (ddd, J = 10.8, 7.7, 2.7 Hz, 1H), 3.37-3.20 (m, 3H), 2.90 (dd, J = 13.6, 6.0 Hz, 1H), 2.78 (dd, J = 13.6, 9.4 Hz, 1H), 2.46-2.34 (m, 4H), 1.87-1.74 (m, 1H), 1.42-1.32 (m, 1H), 0.90 (d, J = 6.6 Hz, 3H) |
| 12 | 83-88 | — | HRMS-ESI (m/z) [M + H]+ calcd for C$_{29}$H$_{39}$N$_2$O$_7$, 527.2752; found, 527.2756 | $^1$H NMR (400 MHz, CDCl$_3$) δ 8.57 (d, J = 8.0 Hz, 1H), 8.30 (d, J = 5.4 Hz, 1H), 7.33-7.23 (m, 4H), 7.23-7.15 (m, 1H), 6.97 (d, J = 5.5 Hz, 1H), 5.14 (dq, J = 9.7, 6.4 Hz, 1H), 4.60 (ddd, J = 9.5, 8.2, 7.3 Hz, 1H), 4.02 (app td, J = 10.5, 3.0 Hz, 1H), 3.87 (s, 3H), 3.57 (app t, J = 9.9 Hz, 1H), 3.42-3.33 (m, 1H), 2.92 (dd, J = 15.5, 3.1 Hz, 1H), 2.82 (dd, J = 15.5, 10.4 Hz, 1H), 2.38 (s, 3H), 2.33-2.21 (m, 1H), 1.99-1.87 (m, 1H), 1.65-1.51 (m, 1H), 1.50-1.32 (m, 6H), 1.30-1.11 (m, 2H), 0.89 (d, J = 6.6 Hz, 3H), 0.87 (d, J = 6.6 Hz, 3H) |
| 13 | — | — | HRMS-ESI (m/z) [M + H]$^+$ calcd for C$_{29}$H$_{38}$N$_2$O$_7$, 527.2752; found, 527.2740 | $^1$H NMR (400 MHz, CDCl$_3$) δ 8.64 (d, J = 8.3 Hz, 1H), 8.34 (d, J = 5.4 Hz, 1H), 7.33-7.25 (m, 2H), 7.23-7.15 (m, 3H), 7.00 (d, J = 5.5 Hz, 1H), 5.09 (dq, J = 9.7, 6.4 Hz, 1H), 4.62 (dt, J = 10.2, 7.8 Hz, 1H), 3.90 (s, 3H), 3.66-3.50 (m, 3H), 2.82 (ddd, J = 13.9, 9.0, 4.9 Hz, 1H), 2.58 (dt, J = 13.9, 8.3 Hz, 1H), 2.47-2.41 (m, 1H), 2.40 (s, 3H), 1.92-1.67 (m, 4H), 1.30 (d, J = 6.4 Hz, 3H), 1.21 (m, 4H), 1.13-1.01 (m, 2H), 0.83 (t, J = 7.2 Hz, 3H) $^{13}$C NMR (101 MHz, CDCl$_3$) δ 172.01, 168.91, 162.52, 159.37, 146.78, 141.84, 141.51, 137.42, 128.43, 128.40, 125.93, 109.76, 79.40, 74.94, 57.66, 56.28, 49.87, 43.36, 34.23, 32.23, 31.45, 27.84, 27.47, 23.32, 20.77, 19.36, 13.81 |
| 14 | — | (Thin Film) 3380, 2934, 1771, | HRMS-ESI (m/z) [M]$^+$ calcd for C$_{23}$H$_{34}$N$_2$O$_7$, | $^1$H NMR (400 MHz, CDCl$_3$) δ 8.63 (d, J = 8.2 Hz, 1H), 8.33 (d, J = 5.4 Hz, 1H), 7.00 (d, J = 5.5 Hz, 1H), 5.17-5.04 (m, 1H), 4.66-4.55 (m, 1H), 3.90 (s, 3H), 3.61-3.51 (m, 1H), 3.50-3.41 (m, 2H), 2.44-2.32 (m, 1H), 2.39 |

TABLE 2-continued

Analytical Data

| Compound Number | MP (° C.) | IR (cm$^{-1}$) | MASS | NMR ($^1$H, $^{13}$H, $^{19}$F) |
|---|---|---|---|---|
| | | 1676, 1507, 1192 | 450.2366; found, 450.2371 | (s, 3H), 1.84-1.40 (m, 4H), 1.31 (d, J = 6.5 Hz, 3H), 1.29-1.09 (m, 6H), 0.97 (t, J = 7.3 Hz, 3H), 0.88 (t, J = 6.9 Hz, 3H) $^{13}$C NMR (101 MHz, CDCl$_3$) δ 172.00, 168.86, 162.48, 159.34, 146.77, 141.48, 137.38, 109.74, 82.06, 74.97, 57.42, 56.26, 49.88, 43.62, 34.24, 27.96, 27.77, 23.37, 22.69, 20.73, 19.35, 13.85, 10.83 |
| 15 | — | (Thin Film) 3380, 2935, 1742, 1676, 1506, 1369, 1192 | HRMS-ESI (m/z) [M]$^+$ calcd for C$_{28}$H$_{36}$N$_2$O$_8$, 528.2472; found, 528.2470 | $^1$H NMR (400 MHz, CDCl$_3$) δ 8.62 (d, J = 8.1 Hz, 1H), 8.34 (d, J = 5.4 Hz, 1H), 7.34-7.25 (m, 2H), 7.01-6.90 (m, 4H), 5.23-5.13 (m, 1H), 4.70-4.59 (m, 1H), 4.20-4.06 (m, 2H), 4.05-3.96 (m, 1H), 3.91-3.81 (m, 1H), 3.89 (s, 3H), 3.63-3.53 (m, 1H), 2.39 (s, 3H), 2.37-2.30 (m, 1H), 2.28-2.17 (m, 1H), 1.79-1.65 (m, 1H), 1.38 (d, J = 6.4 Hz, 3H), 1.37-1.14 (m, 6H), 0.88 (t, J = 6.8 Hz, 3H) $^{13}$C NMR (101 MHz, CDCl$_3$) δ 171.97, 168.88, 162.48, 159.38, 158.37, 146.78, 141.46, 137.41, 129.53, 121.15, 114.54, 109.80, 101.44, 78.33, 74.64, 67.40, 60.50, 56.28, 50.07, 40.01, 34.37, 30.07, 27.54, 27.25, 23.34, 20.75, 19.27, 13.85 |
| 16 | — | (Thin Film) 3349, 2989, 2892, 1755, 1745, 1730, 1684, 1505 | HRMS-ESI (m/z) [M + H]$^+$ calcd for C$_{25}$H$_{31}$N$_2$O$_8$, 487.2075; found, 487.2084 | $^1$H NMR (400 MHz, CDCl$_3$) δ 8.56 (d, J = 7.4 Hz, 1H), 8.30 (d, J = 5.3 Hz, 1H), 7.31-7.26 (m, 2H), 7.26-7.22 (m, 2H), 7.22-7.17 (m, 1H), 6.96 (d, J = 5.4 Hz, 1H), 5.80-5.69 (m, 2H), 5.19 (qd, J = 6.6, 3.7 Hz, 1H), 4.70 (td, J = 7.7, 5.4 Hz, 1H), 3.97-3.92 (m, 1H), 3.91 (s, 3H), 3.63 (dd, J = 10.7, 4.2 Hz, 1H), 3.50 (dd, J = 10.8, 2.6 Hz, 1H), 3.45 (ddd, J = 11.3, 7.6, 2.5 Hz, 1H), 2.87 (dd, J = 13.5, 7.7 Hz, 1H), 2.77 (dd, J = 13.5, 8.5 Hz, 1H), 2.49 (dddd, J = 14.4, 7.7, 5.4, 2.5 Hz, 1H), 2.07 (s, 3H), 1.99-1.84 (m, 1H), 1.82 (ttd, J = 7.9, 4.0, 2.5 Hz, 1H), 1.25 (d, J = 6.6 Hz, 3H) |
| 17 | — | (Thin Film) 3378, 2933, 2873, 1747, 1675, 1499 | HRMS-ESI (m/z) [M + H]$^+$ calcd for C$_{28}$H$_{37}$N$_2$O$_8$, 529.2544; found, 529.2551 | $^1$H NMR (400 MHz, CDCl$_3$) δ 8.40 (d, J = 8.1 Hz, 1H), 8.28 (d, J = 5.3 Hz, 1H), 7.30 (t, J = 7.3 Hz, 2H), 7.24-7.13 (m, 3H), 6.94 (d, J = 5.4 Hz, 1H), 5.77-5.68 (m, 2H), 5.18 (dq, J = 9.4, 6.5 Hz, 1H), 4.63 (dt, J = 10.1, 7.6 Hz, 1H), 3.91 (s, 3H), 3.70-3.58 (m, 1H), 3.57-3.43 (m, 2H), 2.63 (dd, J = 15.6, 3.5 Hz, 1H), 2.51 (dd, J = 15.8, 6.7 Hz, 1H), 2.42 (ddd, J = 14.0, 7.5, 3.7 Hz, 1H), 2.27-2.17 (m, 1H), 2.06 (s, 3H), 1.76-1.59 (m, 3H), 1.59-1.41 (m, 2H), 1.28 (d, J = 6.5 Hz, 3H), 0.89 (t, J = 7.1 Hz, 3H) |
| 18 | — | (Thin Film) 3379, 2934, 2872, 1749, 1676, 1504 | HRMS-ESI (m/z) [M + H]$^+$ calcd for C$_{29}$H$_{39}$N$_2$O$_8$, 543.2701; found, 543.2709 | $^1$H NMR (400 MHz, CDCl$_3$) δ 8.40 (d, J = 8.1 Hz, 1H), 8.28 (d, J = 5.4 Hz, 1H), 7.32-7.26 (m, 2H), 7.23-7.14 (m, 3H), 6.95 (d, J = 5.4 Hz, 1H), 5.81-5.66 (m, 2H), 5.18 (dq, J = 9.5, 6.5 Hz, 1H), 4.63 (dt, J = 10.1, 7.7 Hz, 1H), 3.90 (s, 3H), 3.69-3.60 (m, 1H), 3.56-3.45 (m, 2H), 2.62 (dd, J = 15.8, 3.4 Hz, 1H), 2.52 (dd, J = 15.8, 6.6 Hz, 1H), 2.42 (ddd, J = 14.0, 7.5, 3.7 Hz, 1H), 2.23 (dddd, J = 12.7, 10.0, 6.6, 3.4 Hz, 1H), 2.06 (s, 3H), 1.77-1.64 (m, 1H), 1.64-1.53 (m, 2H), 1.45 (dddd, J = 16.4, 11.3, 5.3, 2.3 Hz, 1H), 1.35-1.20 (m, 3H), 1.29 (d, J = 6.5 Hz, 3H), 0.88 (t, J = 7.0 Hz, 3H) |

TABLE 2-continued

| Compound Number | MP (° C.) | IR (cm$^{-1}$) | MASS | NMR ($^1$H, $^{13}$H, $^{19}$F) |
|---|---|---|---|---|
| 19 | — | (Thin Film) 3377, 3026, 2936, 1747, 1674, 1497 | HRMS-ESI (m/z) [M + H]$^+$ calcd for C$_{32}$H$_{37}$N$_2$O$_8$, 577.2544. found, 577.2552 | $^1$H NMR (400 MHz, CDCl$_3$) δ 8.35 (d, J = 7.9 Hz, 1H), 8.25 (d, J = 5.4 Hz, 1H), 7.34-7.26 (m, 3H), 7.28-7.21 (m, 4H), 7.18 (d, J = 7.1 Hz, 3H), 6.92 (d, J = 5.4 Hz, 1H), 5.76-5.63 (m, 2H), 5.22 (dq, J = 9.6, 6.5 Hz, 1H), 4.64 (dt, J = 9.6, 7.5 Hz, 1H), 4.00 (td, J = 10.6, 2.5 Hz, 1H), 3.88 (s, 3H), 3.66 (t, J = 10.0 Hz, 1H), 3.43 (ddd, J = 9.5, 4.6, 2.2 Hz, 1H), 3.01 (dd, J = 15.8, 2.6 Hz, 1H), 2.87 (dd, J = 15.7, 10.9 Hz, 1H), 2.76 (dd, J = 15.9, 3.8 Hz, 1H), 2.66 (dd, J = 15.8, 6.2 Hz, 1H), 2.39 (tdd, J = 10.0, 6.3, 3.9 Hz, 1H), 2.30 (ddd, J = 14.6, 7.4, 4.4 Hz, 1H), 2.04 (s, 3H), 1.66-1.52 (m, 1H), 1.36 (d, J = 6.5 Hz, 3H) |
| 20 | — | (Thin Film) 3378, 2935, 2875, 1749, 1675, 1505 | HRMS-ESI (m/z) [M + H]$^+$ calcd for C$_{28}$H$_{37}$N$_2$O$_9$, 545.2494; found, 545.2490 | $^1$H NMR (400 MHz, CDCl$_3$) δ 8.41 (d, J = 7.9 Hz, 1H), 8.28 (d, J = 5.4 Hz, 1H), 7.31-7.23 (m, 2H), 7.24-7.17 (m, 3H), 6.95 (d, J = 5.4 Hz, 1H), 5.79-5.65 (m, 2H), 5.16 (dq, J = 9.6, 6.5 Hz, 1H), 4.64 (dt, J = 10.2, 7.6 Hz, 1H), 3.90 (s, 3H), 3.74-3.62 (m, 2H), 3.55-3.48 (m, 1H), 3.48-3.35 (m, 2H), 3.31 (s, 3H), 2.62 (dd, J = 15.9, 3.4 Hz, 1H), 2.52 (dd, J = 15.9, 6.4 Hz, 1H), 2.44 (ddt, J = 13.5, 7.6, 3.6 Hz, 1H), 2.28 (tdd, J = 9.9, 6.5, 3.4 Hz, 1H), 2.06 (s, 3H), 2.01-1.80 (m, 2H), 1.77-1.68 (m, 1H), 1.29 (d, J = 6.5 Hz, 3H) |
| 21 | — | — | HRMS-ESI (m/z) [M + H]$^+$ calcd for C$_{25}$H$_{30}$FN$_2$O$_8$, 505.1981; found 505.1988 | $^1$H NMR (400 MHz, CDCl$_3$) δ 8.55 (d, J = 7.3 Hz, 1H), 8.30 (d, J = 5.4 Hz, 1H), 7.20 (dd, J = 8.4, 5.6 Hz, 2H), 7.01-6.94 (m, 3H), 5.75 (d, J = 1.6 Hz, 2H), 5.17 (qd, J = 6.6, 3.1 Hz, 1H), 4.70 (td, J = 7.7, 5.3 Hz, 1H), 3.96 (ddd, J = 11.1, 7.6, 2.8 Hz, 1H), 3.91 (s, 3H), 3.63 (dd, J = 10.7, 3.9 Hz, 1H), 3.50 (dd, J = 10.7, 2.4 Hz, 1H), 3.45 (ddd, J = 10.8, 7.6, 2.5 Hz, 1H), 2.85 (dd, J = 13.6, 7.9 Hz, 1H), 2.77 (dd, J = 13.6, 8.4 Hz, 1H), 2.56-2.39 (m, 1H), 2.08 (s, 3H), 1.98-1.85 (m, 1H), 1.78-1.67 (m, 1H), 1.25 (d, J = 6.6 Hz, 3H) $^{19}$F NMR (376 MHz, CDCl$_3$) δ −117.25 |
| 22 | — | — | HRMS-ESI (m/z) [M + H]$^+$ calcd for C$_{24}$H$_{34}$FN$_2$O$_8$, 533.2294; found, 533.2297 | $^1$H NMR (400 MHz, CDCl$_3$) δ 8.41 (d, J = 7.8 Hz, 1H), 8.28 (d, J = 5.3 Hz, 1H), 7.14 (dd, J = 8.5, 5.4 Hz, 2H), 7.03-6.92 (m, 3H), 5.80-5.66 (m, 2H), 5.16 (dq, J = 9.4, 6.5 Hz, 1H), 4.63 (dt, J = 10.0, 7.6 Hz, 1H), 3.91 (s, 3H), 3.64 (t, J = 10.2 Hz, 1H), 3.57-3.50 (m, 1H), 3.41 (td, J = 10.2, 3.0 Hz, 1H), 2.63-2.55 (m, 1H), 2.51 (dd, J = 15.8, 6.5 Hz, 1H), 2.42 (ddd, J = 14.0, 7.4, 3.8 Hz, 1H), 2.24-2.12 (m, 1H), 2.07 (s, 3H), 1.78-1.53 (m, 3H), 1.28 (d, J = 6.5 Hz, 3H), 0.95 (t, J = 7.2 Hz, 3H) $^{19}$F NMR (376 MHz, CDCl$_3$) δ −116.89 |
| 23 | — | — | HRMS-ESI (m/z) [M + H]$^+$ calcd for C$_{29}$H$_{38}$FN$_2$O$_8$, 561.2607; found, 561.2602 | $^1$H NMR (400 MHz, CDCl$_3$) δ 8.40 (d, J = 8.0 Hz, 1H), 8.28 (d, J = 5.3 Hz, 1H), 7.14 (dd, J = 8.5, 5.5 Hz, 2H), 6.99 (t, J = 8.7 Hz, 2H), 6.95 (d, J = 5.4 Hz, 1H), 5.85-5.61 (m, 2H), 5.16 (dq, J = 9.5, 6.5 Hz, 1H), 4.63 (dt, J = 10.2, 7.6 Hz, 1H), 3.91 (s, 3H), 3.71-3.57 (m, 1H), 3.56-3.38 (m, 2H), 2.59 (dd, J = 15.6, 3.8 Hz, 1H), 2.50 (dd, J = 15.8, 6.6 Hz, 1H), 2.46-2.37 (m, 1H), 2.23-2.12 (m, 1H), 2.06 (s, 3H), 1.76-1.64 (m, 1H), 1.64-1.50 (m, 2H), 1.44 (tdd, J = 11.0, 8.8, 6.1 Hz, 1H), 1.28 (d, J = 6.4 Hz, 3H), 1.38-1.16 (m, 3H), 0.88 (t, J = 7.0 Hz, 3H) $^{19}$F NMR (376 MHz, CDCl$_3$) δ −116.89 |
| 24 | — | — | HRMS-ESI (m/z) [M + H]$^+$ calcd for C$_{33}$H$_{38}$FN$_2$O$_8$, 609.2607; found, 609.2599 | $^1$H NMR (400 MHz, CDCl$_3$) δ 8.42 (d, J = 7.9 Hz, 1H), 8.29 (d, J = 5.4 Hz, 1H), 7.33-7.25 (m, 2H), 7.23-7.17 (m, 1H), 7.18-7.11 (m, 2H), 7.01 (dd, J = 8.5, 5.5 Hz, 2H), 6.97-6.86 (m, 3H), 5.84-5.64 (m, 2H), 5.14 (dq, J = 9.4, 6.4 Hz, 1H), 4.65 (dt, J = 10.2, 7.7 Hz, 1H), 3.91 (s, 3H), 3.75-3.58 (m, 2H), 3.53 (td, J = 10.6, 2.3 Hz, 1H), 2.79 (ddd, J = 13.7, 9.0, 4.6 Hz, 1H), 2.67-2.37 (m, 4H), 2.25- |

TABLE 2-continued

Analytical Data

| Compound Number | MP (° C.) | IR (cm$^{-1}$) | MASS | NMR ($^1$H, $^{13}$H, $^{19}$F) |
|---|---|---|---|---|
| | | | | 2.12 (m, 1H), 2.07 (s, 3H), 2.02-1.68 (m, 3H), 1.29 (d, J = 6.5 Hz, 3H) $^{19}$F NMR (376 MHz, CDCl$_3$) δ −116.77 |
| 25 | — | — | HRMS-ESI (m/z) [M + H]$^+$ calcd for C$_{28}$H$_{36}$FN$_2$O$_9$, 563.2399; found, 563.2400 | $^1$H NMR (400 MHz, CDCl$_3$) δ 8.41 (d, J = 7.9 Hz, 1H), 8.30-8.25 (m, 1H), 7.15 (dd, J = 8.5, 5.4 Hz, 2H), 7.01-6.92 (m, 3H), 5.80-5.68 (m, 2H), 5.14 (dq, J = 9.2, 6.5 Hz, 1H), 4.64 (dt, J = 9.3, 7.6 Hz, 1H), 3.91 (s, 3H), 3.74-3.62 (m, 2H), 3.57-3.35 (m, 3H), 3.31 (s, 3H), 2.59 (dd, J = 16.1, 3.3 Hz, 1H), 2.50 (dd, J = 15.9, 6.4 Hz, 1H), 2.43 (ddd, J = 14.1, 7.4, 4.0 Hz, 1H), 2.22 (dtd, J = 10.1, 6.5, 3.3 Hz, 1H), 2.06 (s, 3H), 1.97-1.85 (m, 2H), 1.71 (dtd, J = 14.4, 11.9, 11.3, 2.7 Hz, 1H), 1.29 (d, J = 6.5 Hz, 3H) $^{19}$F NMR (376 MHz, CDCl$_3$) δ −116.86 |
| 26 | 48-54 | — | HRMS-ESI (m/z) [M + H]$^+$ calcd for C$_{31}$H$_{43}$N$_2$O$_8$, 571.3014; found, 571.3023 | $^1$H NMR (400 MHz, CDCl$_3$) δ 8.41 (d, J = 8.0 Hz, 1H), 8.29 (d, J = 5.3 Hz, 1H), 7.30-7.25 (m, 2H), 7.23-7.15 (m, 3H), 6.95 (d, J = 5.4 Hz, 1H), 5.75 (d, J = 1.0 Hz, 2H), 5.09 (dq, J = 9.5, 6.4 Hz, 1H), 4.65 (app dt, J = 10.1, 7.7 Hz, 1H), 3.91 (s, 3H), 3.69-3.51 (m, 3H), 2.82 (ddd, J = 13.7, 9.0, 4.7 Hz, 1H), 2.65-2.52 (m, 1H), 2.51-2.39 (m, 1H), 2.07 (s, 3H), 1.89-1.74 (m, 4H), 1.40-1.20 (m, 6H), 1.02-0.88 (m, 2H), 0.82 (d, J = 6.6 Hz, 3H), 0.79 (d, J = 6.6 Hz, 3H) |
| 27 | 49-54 | — | HRMS-ESI (m/z) [M + H]$^+$ calcd for C$_{31}$H$_{42}$FN$_2$O$_8$, 589.2920; found, 589.2935 | $^1$H NMR (400 MHz, CDCl$_3$) δ 8.41 (d, J = 8.0 Hz, 1H), 8.29 (d, J = 5.3 Hz, 1H), 7.19-7.10 (m, 2H), 7.01-6.92 (m, 3H), 5.75 (s, 2H), 5.08 (dq, J = 9.6, 6.5 Hz, 1H), 4.64 (app dt, J = 10.3, 7.8 Hz, 1H), 3.91 (s, 3H), 3.68-3.49 (m, 3H), 2.78 (ddd, J = 13.4, 8.6, 4.5 Hz, 1H), 2.63-2.50 (m, 1H), 2.45 (ddd, J = 13.6, 7.6, 3.5 Hz, 1H), 2.07 (s, 3H), 1.90-1.67 (m, 4H), 1.39-1.15 (m, 6H), 1.01-0.86 (m, 2H), 0.82 (d, J = 6.6 Hz, 3H), 0.79 (d, J = 6.6 Hz, 3H) |
| 28 | — | (Thin Film) 3382, 2934, 2869, 1747, 1675, 1501, 1200 | HRMS-ESI (m/z) [M + H]$^+$ calcd for C$_{31}$H$_{35}$N$_2$O$_8$, 563.2388; found, 563.2397 | $^1$H NMR (400 MHz, CDCl$_3$) δ 8.52 (d, J = 7.3 Hz, 1H), 8.29 (d, J = 5.3 Hz, 1H), 7.45-7.15 (m, 9H), 6.95 (d, J = 5.4 Hz, 1H), 5.78-5.69 (m, 2H), 4.92 (qd, J = 6.6, 4.4 Hz, 1H), 4.63 (app td, J = 7.5, 5.3 Hz, 1H), 3.90 (s, 3H), 3.82 (ddd, J = 10.9, 7.7, 2.7 Hz, 1H), 3.39-3.22 (m, 3H), 2.90 (dd, J = 13.6, 6.0 Hz, 1H), 2.78 (dd, J = 13.6, 9.4 Hz, 1H), 2.43 (dddd, J = 14.4, 7.9, 5.4, 2.6 Hz, 1H), 2.06 (s, 3H), 1.83 (app dtd, J = 14.8, 7.5, 2.7 Hz, 1H), 1.44-1.33 (m, 1H), 0.91 (d, J = 6.6 Hz, 3H) |
| 29 | 55-60 | — | HRMS-ESI (m/z) [M + H]$^+$ calcd for C$_{30}$H$_{41}$N$_2$O$_8$, 557.2857; found, 557.2867 | $^1$H NMR (400 MHz, CDCl$_3$) δ 8.35 (d, J = 8.0 Hz, 1H), 8.26 (d, J = 5.4 Hz, 1H), 7.34-7.15 (m, 5H), 6.93 (d, J = 5.4 Hz, 1H), 5.72 (s, 2H), 5.15 (dq, J = 9.7, 6.4 Hz, 1H), 4.63 (app dt, J = 9.5, 7.6 Hz, 1H), 4.04 (app td, J = 10.5, 3.0 Hz, 1H), 3.89 (s, 3H), 3.60 (app t, J = 10.0 Hz, 1H), 3.44-3.35 (m, 1H), 2.93 (dd, J = 15.5, 3.0 Hz, 1H), 2.83 (dd, J = 15.5, 10.4 Hz, 1H), 2.36-2.24 (m, 1H), 2.05 (s, 3H), 2.00-1.88 (m, 1H), 1.67-1.53 (m, 1H), 1.49-1.34 (m, 6H), 1.30-1.13 (m, 2H), 0.89 (d, J = 6.7 Hz, 3H), 0.87 (d, J = 6.5 Hz, 3H) |
| 30 | 86-88 | — | HRMS-ESI (m/z) [M + H]$^+$ calcd for C$_{23}$H$_{35}$N$_2$O$_8$, 467.2388; found, 467.2394 | $^1$H NMR (400 MHz, CDCl$_3$) δ 8.51 (d, J = 7.4 Hz, 1H), 8.28 (d, J = 5.3 Hz, 1H), 6.95 (d, J = 5.4 Hz, 1H), 5.79-5.70 (m, 2H), 5.11 (qd, J = 6.6, 5.0 Hz, 1H), 4.67 (app td, J = 7.9, 5.7 Hz, 1H), 3.91 (s, 3H), 3.85 (ddd, J = 10.2, 6.9, 2.7 Hz, 1H), 3.63 (dd, J = 11.0, 5.4 Hz, 1H), 3.58 (dd, J = 11.0, 3.5 Hz, 1H), 3.50 (ddd, J = 10.8, 8.0, 2.3 Hz, 1H), 2.54-2.42 (m, 1H), 2.07 (s, 3H), 1.93-1.79 (m, 1H), 1.65-1.34 (m, 4H), 1.33 (d, J = 6.6 Hz, 3H), 1.22-1.11 (m, 2H), 0.88 (app dd, J = 6.6, 4.1 Hz, 6H) |
| 31 | — | — | HRMS-ESI (m/z) [M + H]$^+$ calcd for | $^1$H NMR (400 MHz, CDCl$_3$) δ 8.41 (d, J = 8.0 Hz, 1H), 8.29 (d, J = 5.4 Hz, 1H), 7.32-7.25 (m, 2H), 7.23-7.16 (m, 3H), 6.95 (d, J = 5.4 Hz, 1H), 5.75 (d, J = 1.1 Hz, 2H), 5.09 (dq, J = |

TABLE 2-continued

Analytical Data

| Compound Number | MP (° C.) | IR (cm$^{-1}$) | MASS | NMR ($^1$H, $^{13}$H, $^{19}$F) |
|---|---|---|---|---|
| | | | C$_{30}$H$_{40}$N$_2$O$_8$, 557.2857; found, 557.2849 | 9.6, 6.5 Hz, 1H), 4.65 (dt, J = 10.3, 7.7 Hz, 1H), 3.91 (s, 3H), 3.68-3.53 (m, 3H), 2.83 (ddd, J = 13.9, 9.1, 4.8 Hz, 1H), 2.58 (dt, J = 13.9, 8.3 Hz, 1H), 2.51-2.39 (m, 1H), 2.07 (s, 3H), 1.93-1.71 (m, 4H), 1.31 (d, J = 6.4 Hz, 3H), 1.28-1.14 (m, 4H), 1.13-1.03 (m, 2H), 0.84 (t, J = 7.2 Hz, 3H) $^{13}$C NMR (101 MHz, CDCl$_3$) δ 172.14, 170.26, 163.09, 160.18, 145.86, 143.76, 142.68, 141.84, 128.43, 128.40, 125.93, 109.54, 89.51, 79.41, 74.93, 57.66, 56.18, 50.12, 43.37, 34.12, 32.24, 31.45, 27.84, 27.47, 23.32, 20.90, 19.38, 13.81 |
| 32 | — | (Thin Film) 3379, 2936, 2253, 1673 | HRMS-ESI (m/z) [M + H]$^+$ calcd for C$_{27}$H$_{40}$N$_2$O$_{10}$, 553.2756; found, 553.2763 | $^1$H NMR (400 MHz, CDCl$_3$) δ 8.40 (d, J = 7.9 Hz, 1H), 8.29 (d, J = 5.4 Hz, 1H), 6.95 (d, J = 5.4 Hz, 1H), 5.74 (d, J = 0.8 Hz, 2H), 5.14 (dq, J = 9.5, 6.5 Hz, 1H), 4.65 (dt, J = 9.7, 7.5 Hz, 1H), 4.30 (dd, J = 12.5, 2.5 Hz, 1H), 4.20 (dd, J = 12.5, 7.7 Hz, 1H), 3.91 (s, 3H), 3.90-3.86 (m, 1H), 3.76 (t, J = 10.0 Hz, 1H), 3.54 (ddd, J = 9.4, 4.4, 2.3 Hz, 1H), 2.66-2.53 (m, 1H), 2.46-2.36 (m, 1H), 2.07 (s, 3H), 1.97 (t, J = 10.3 Hz, 1H), 1.80-1.69 (m, 1H), 1.36 (d, J = 6.5 Hz, 4H), 1.34-1.22 (m, 5H), 1.19 (dd, J = 7.0, 1.1 Hz, 6H), 0.90 (d, J = 6.9 Hz, 3H) |
| 33 | — | (Thin Film) 3378, 2955, 2929, 2870, 1745, 1675 | HRMS-ESI (m/z) [M + H]$^+$ calcd for C$_{22}$H$_{32}$N$_2$O$_8$, 453.2231; found, 453.2234 | $^1$H NMR (400 MHz, CDCl$_3$) δ 8.52 (d, J = 7.5 Hz, 1H), 8.28 (d, J = 5.4 Hz, 1H), 6.94 (d, J = 5.4 Hz, 1H), 5.75 (d, J = 1.7 Hz, 2H), 5.11 (q, J = 6.3 Hz, 1H), 4.72-4.63 (m, 1H), 3.91 (s, 3H), 3.88-3.81 (m, 1H), 3.60 (qd, J = 11.0, 4.5 Hz, 2H), 3.55-3.45 (m, 1H), 2.55-2.42 (m, 1H), 2.07 (s, 3H), 1.93-1.80 (m, 1H), 1.62 (s, 1H), 1.51-1.39 (m, 1H), 1.32 (d, J = 6.7 Hz, 3H), 1.31-1.22 (m, 5H), 0.90 (t, J = 6.9 Hz, 3H) |
| 34 | — | (Thin Film) 3371, 2957, 1754, 1677, 1506, 1374, 1202 | HRMS-ESI (m/z) [M]$^+$ calcd for C$_{24}$H$_{36}$N$_2$O$_8$, 480.2472; found, 480.2475 | $^1$H NMR (400 MHz, CDCl$_3$) δ 8.40 (d, J = 7.9 Hz, 1H), 8.28 (d, J = 5.4 Hz, 1H), 6.95 (d, J = 5.4 Hz, 1H), 5.74 (s, 2H), 5.18-5.05 (m, 1H), 4.69-4.57 (m, 1H), 3.91 (s, 3H), 3.64-3.53 (m, 1H), 3.52-3.41 (m, 2H), 2.47-2.35 (m, 1H), 2.07 (s, 3H), 1.85-1.42 (m, 4H), 1.33 (d, J = 6.5 Hz, 3H), 1.31-1.09 (m, 6H), 0.98 (t, J = 7.2 Hz, 3H), 0.90 (t, J = 6.9 Hz, 3H) $^{13}$C NMR (101 MHz, CDCl$_3$) δ 172.12, 170.20, 163.05, 160.15, 145.85, 143.69, 142.66, 109.54, 89.45, 82.04, 74.96, 57.41, 56.17, 50.12, 43.61, 34.11, 27.96, 27.76, 23.36, 22.67, 20.85, 19.37, 13.84, 10.83 |
| 35 | — | (Thin Film) 3370, 1752, 1674, 1499, 1370, 1242 | HRMS-ESI (m/z) [M]$^+$ calcd for C$_{29}$H$_{38}$N$_2$O$_9$, 558.2577; found, 558.2569 | $^1$H NMR (400 MHz, CDCl$_3$) δ 8.39 (d, J = 7.9 Hz, 1H), 8.29 (d, J = 5.4 Hz, 1H), 7.36-7.25 (m, 2H), 7.03-6.87 (m, 4H), 5.74 (s, 2H), 5.25-5.11 (m, 1H), 4.73-4.60 (m, 1H), 4.21-4.06 (m, 2H), 4.05-3.97 (m, 1H), 3.91-3.83 (m, 1H), 3.90 (s, 3H), 3.64-3.56 (m, 1H), 2.44-2.31 (m, 1H), 2.30-2.18 (m, 1H), 2.07 (s, 3H), 1.81-1.67 (m, 1H), 1.39 (d, J = 6.4 Hz, 3H), 1.36-1.12 (m, 6H), 0.88 (t, J = 6.8 Hz, 3H) $^{13}$C NMR (101 MHz, CDCl$_3$) δ 172.10, 170.24, 163.06, 160.18, 158.37, 145.85, 143.75, 142.63, 129.54, 121.15, 114.54, 109.58, 89.47, 78.30, 74.61, 67.37, 60.44, 56.19, 50.30, 39.97, 34.25, 27.55, 27.25, 23.34, 20.88, 19.30, 13.85 |
| 36 | — | (Thin Film) 3378, 2975, 2932, 2872, 1742, 1675, 1501 | HRMS-ESI (m/z) [M + H]$^+$ calcd for C$_{27}$H$_{35}$N$_2$O$_8$, 515.2388; found, 515.2398 | $^1$H NMR (400 MHz, CDCl$_3$) δ 8.63 (d, J = 7.4 Hz, 1H), 8.29 (d, J = 5.3 Hz, 1H), 7.32-7.26 (m, 2H), 7.26-7.22 (m, 2H), 7.19 (tt, J = 6.1, 1.5 Hz, 1H), 6.95 (d, J = 5.4 Hz, 1H), 5.89-5.62 (m, 2H), 5.19 (qd, J = 6.6, 3.7 Hz, 1H), 4.70 (td, J = 7.7, 5.4 Hz, 1H), 3.94 (ddd, J = 11.4, 7.4, 2.8 Hz, 1H), 3.89 (s, 3H), 3.63 (dd, J = 10.7, 4.2 Hz, 1H), 3.50 (dd, J = 10.8, 2.6 Hz, 1H), 3.45 (ddd, J = 11.2, 7.7, 2.5 Hz, 1H), 2.88 (dd, J = 13.5, 7.7 Hz, 1H), 2.77 (dd, J = 13.5, 8.5 Hz, 1H), 2.55 (hept, J = 7.0 Hz, 1H), |

TABLE 2-continued

Analytical Data

| Compound Number | MP (° C.) | IR (cm$^{-1}$) | MASS | NMR ($^1$H, $^{13}$H, $^{19}$F) |
|---|---|---|---|---|
| 37 | — | (Thin Film) 3379, 2975, 2936, 1744, 1675, 1498 | HRMS-ESI (m/z) [M + H]$^+$ calcd for C$_{34}$H$_{41}$N$_2$O$_8$, 605.2857; found, 605.2868 | 2.48 (dddd, J = 12.8, 7.7, 5.1, 2.5 Hz, 1H), 1.94-1.86 (m, 1H), 1.86-1.78 (m, 1H), 1.25 (d, J = 6.6 Hz, 3H), 1.14 (d, J = 7.0 Hz, 6H) $^1$H NMR (400 MHz, CDCl$_3$) δ 8.42 (d, J = 7.9 Hz, 1H), 8.25 (d, J = 5.3 Hz, 1H), 7.36-7.22 (m, 3H), 7.27-7.21 (m, 4H), 7.21-7.15 (m, 3H), 6.91 (d, J = 5.4 Hz, 1H), 5.83-5.64 (m, 2H), 5.22 (dq, J = 9.6, 6.5 Hz, 1H), 4.64 (dt, J = 9.7, 7.5 Hz, 1H), 4.00 (td, J = 10.6, 2.5 Hz, 1H), 3.86 (s, 3H), 3.66 (t, J = 10.0 Hz, 1H), 3.43 (ddd, J = 9.6, 4.6, 2.3 Hz, 1H), 3.06-2.97 (m, 1H), 2.87 (dd, J = 15.7, 10.9 Hz, 1H), 2.76 (dd, J = 15.8, 3.8 Hz, 1H), 2.66 (dd, J = 15.8, 6.2 Hz, 1H), 2.52 (p, J = 7.0 Hz, 1H), 2.39 (tdd, J = 9.9, 6.3, 3.8 Hz, 1H), 2.34-2.25 (m, 1H), 1.65-1.53 (m, 1H), 1.37 (d, J = 6.5 Hz, 3H), 1.12 (d, J = 7.0 Hz, 6H) |
| 38 | — | — | HRMS-ESI (m/z) [M + H]$^+$ calcd for C$_{35}$H$_{42}$FN$_2$O$_8$, 637.2920; found, 637.2922 | $^1$H NMR (400 MHz, CDCl$_3$) δ 8.48 (d, J = 7.9 Hz, 1H), 8.28 (d, J = 5.3 Hz, 1H), 7.31-7.24 (m, 2H), 7.20 (t, J = 7.3 Hz, 1H), 7.14 (d, J = 6.7 Hz, 2H), 7.01 (dd, J = 8.5, 5.5 Hz, 2H), 6.97-6.89 (m, 3H), 5.82-5.72 (m, 2H), 5.14 (dq, J = 9.5, 6.5 Hz, 1H), 4.65 (dt, J = 10.2, 7.6 Hz, 1H), 3.89 (s, 3H), 3.73-3.65 (m, 1H), 3.65-3.57 (m, 1H), 3.53 (td, J = 10.7, 2.3 Hz, 1H), 2.79 (ddd, J = 13.6, 8.9, 4.6 Hz, 1H), 2.52 (dtdd, J = 32.0, 15.7, 7.0, 4.4 Hz, 5H), 2.25-2.09 (m, 1H), 2.03-1.69 (m, 3H), 1.29 (d, J = 6.5 Hz, 3H), 1.14 (d, J = 7.0 Hz, 6H) $^{19}$F NMR (376 MHz, CDCl$_3$) δ -116.81 |
| 39 | 49-54 | — | HRMS-ESI (m/z) [M + H]$^+$ calcd for C$_{33}$H$_{46}$FN$_2$O$_8$, 617.3233. found, 617.3234 | $^1$H NMR (400 MHz, CDCl$_3$) δ 8.48 (d, J = 8.0 Hz, 1H), 8.28 (d, J = 5.3 Hz, 1H), 7.19-7.10 (m, 2H), 7.01-6.91 (m, 3H), 5.83-5.74 (m, 2H), 5.08 (dq, J = 9.8, 6.4 Hz, 1H), 4.64 (app dt, J = 10.3, 7.8 Hz, 1H), 3.89 (s, 3H), 3.68-3.49 (m, 3H), 2.78 (ddd, J = 13.5, 8.6, 4.6 Hz, 1H), 2.63-2.49 (m, 2H), 2.45 (ddd, J = 13.7, 7.6, 3.5 Hz, 1H), 1.90-1.67 (m, 4H), 1.39-1.11 (m, 12H), 1.01-0.85 (m, 2H) 0.82 (d, J = 6.6 Hz, 3H), 0.79 (d, J = 6.6 Hz, 3H) |
| 40 | 54-59 | — | HRMS-ESI (m/z) [M + H]$^+$ calcd for C$_{33}$H$_{39}$N$_2$O$_8$, 591.2701; found, 591.2713 | $^1$H NMR (400 MHz, CDCl$_3$) δ 8.58 (d, J = 7.3 Hz, 1H), 8.28 (d, J = 5.3 Hz, 1H), 7.45-7.23 (m, 8H), 7.23-7.16 (m, 1H), 6.94 (d, J = 5.4 Hz, 1H), 5.81-5.72 (m, 2H), 4.92 (qd, J = 6.6, 4.3 Hz, 1H), 4.62 (app td, J = 7.5, 5.3 Hz, 1H), 3.88 (s, 3H), 3.82 (ddd, J = 10.8, 7.7, 2.7 Hz, 1H), 3.39-3.22 (m, 3H), 2.90 (dd, J = 13.6, 6.0 Hz, 1H), 2.78 (dd, J = 13.6, 9.4 Hz, 1H), 2.54 (hept, J = 7.0 Hz, 1H), 2.47-2.36 (m, 1H), 1.90-1.77 (m, 1H), 1.44-1.32 (m, 1H), 1.13 (d, J = 7.0 Hz, 6H), 0.91 (d, J = 6.6 Hz, 3H) |
| 41 | 110-112 | (Thin Film) 3379, 2935, 1745, 1676, 1498, 1317, 1217 | HRMS-ESI (m/z) [M]$^+$ calcd for C$_{31}$H$_{42}$N$_2$O$_9$, 586.2890; found, 586.2882 | $^1$H NMR (400 MHz, CDCl$_3$) δ 8.46 (d, J = 8.0 Hz, 1H), 8.28 (d, J = 5.4 Hz, 1H), 7.35-7.24 (m, 2H), 7.02-6.89 (m, 4H), 5.82-5.73 (m, 2H), 5.25-5.12 (m, 1H), 4.71-4.60 (m, 1H), 4.21-4.06 (m, 2H), 4.06-3.97 (m, 1H), 3.93-3.84 (m, 1H), 3.89 (s, 3H), 3.63-3.56 (m, 1H), 2.54 (hept, J = 7.0 Hz, 1H), 2.43-2.32 (m, 1H), 2.29-2.19 (m, 1H), 1.81-1.67 (m, 1H), 1.39 (d, J = 6.5 Hz, 3H), 1.37-1.17 (m, 6H), 1.14 (d, J = 7.0 Hz, 6H), 0.88 (t, J = 6.8 Hz, 3H) $^{13}$C NMR (101 MHz, CDCl$_3$) δ 176.21, 172.09, 163.02, 160.17, 158.37, 145.70, 143.99, 142.28, 129.54, 121.15, 114.54, 109.51, 89.83, 78.31, 74.60, 67.39, 60.49, 56.13, 50.29, 39.99, 34.28, 33.85, 27.56, 27.26, 23.35, 19.30, 18.69, 13.85 |
| 42 | — | (Thin Film) 3378, 2976, 2928, 2870, | HRMS-ESI (m/z) [M + H]$^+$ calcd for C$_{27}$H$_{35}$N$_2$O$_9$, 531.2337; | $^1$H NMR (400 MHz, CDCl$_3$) δ 8.58 (d, J = 7.4 Hz, 1H), 8.29 (d, J = 5.3 Hz, 1H), 7.32-7.28 (m, 1H), 7.27-7.22 (m, 3H), 7.22-7.17 (m, 1H), 6.96 (d, J = 5.4 Hz, 1H), 5.93-5.71 (m, 2H), 5.19 (qd, J = 6.6, 3.7 Hz, 1H), 4.68 (td, J = 7.7, 5.3 Hz, 1H), 4.10 (s, 2H), 4.00-3.89 |

TABLE 2-continued

Analytical Data

| Compound Number | MP (° C.) | IR (cm$^{-1}$) | MASS | NMR ($^1$H, $^{13}$H, $^{19}$F) |
|---|---|---|---|---|
| | | 1772, 1740, 1675, 1501 | found, 531.2349 | (m, 1H), 3.90 (s, 3H), 3.63 (dd, J = 11.1, 4.6 Hz, 1H), 3.59 (q, J = 6.9 Hz, 2H), 3.50 (dd, J = 10.8, 2.6 Hz, 1H), 3.45 (ddd, J = 11.3, 7.7, 2.6 Hz, 1H), 2.87 (dd, J = 13.5, 7.7 Hz, 1H), 2.77 (dd, J = 13.5, 8.5 Hz, 1H), 2.48 (dddd, J = 14.3, 7.7, 5.4, 2.5 Hz, 1H), 1.96-1.86 (m, 1H), 1.86-1.77 (m, 1H), 1.25 (d, J = 6.8 Hz, 3H), 1.22 (t, J = 7.0 Hz, 3H) |
| 43 | — | (Thin Film) 3378, 2933, 2873, 1744, 1675, 1502 | HRMS-ESI (m/z) [M + H]$^+$ calcd for C$_{30}$H$_{41}$N$_2$O$_9$, 573.2807; found, 573.2809. | $^1$H NMR (400 MHz, CDCl$_3$) δ 8.41 (d, J = 8.0 Hz, 1H), 8.28 (d, J = 5.4 Hz, 1H), 7.32-7.27 (m, 2H), 7.23-7.15 (m, 3H), 6.94 (d, J = 5.5 Hz, 1H), 5.88-5.78 (m, 2H), 5.18 (dq, J = 9.4, 6.5 Hz, 1H), 4.61 (dt, J = 10.2, 7.7 Hz, 1H), 4.09 (s, 2H), 3.90 (s, 3H), 3.68-3.61 (m, 1H), 3.58 (q, J = 7.0 Hz, 2H), 3.54-3.44 (m, 2H), 2.63 (dd, J = 15.7, 3.4 Hz, 1H), 2.51 (dd, J = 15.8, 6.7 Hz, 1H), 2.41 (ddd, J = 14.0, 7.6, 3.7 Hz, 1H), 2.22 (tdd, J = 9.9, 6.7, 3.3 Hz, 1H), 1.77-1.43 (m, 5H), 1.28 (d, J = 6.5 Hz, 3H), 1.22 (t, J = 7.0 Hz, 3H), 0.89 (t, J = 7.1 Hz, 3H) |
| 44 | — | (Thin Film) 3379, 2977, 2935, 2880, 1772, 1744, 1675, 1498 | HRMS-ESI (m/z) [M + H]$^+$ calcd for C$_{34}$H$_{41}$N$_2$O$_9$, 621.2807; found, 621.2819 | $^1$H NMR (400 MHz, CDCl$_3$) δ 8.37 (d, J = 8.0 Hz, 1H), 8.25 (d, J = 5.4 Hz, 1H), 7.36-7.25 (m, 3H), 7.26-7.21 (m, 4H), 7.20-7.16 (m, 3H), 6.92 (d, J = 5.4 Hz, 1H), 5.80 (s, 2H), 5.22 (dq, J = 9.5, 6.5 Hz, 1H), 4.62 (dt, J = 9.6, 7.5 Hz, 1H), 4.08 (s, 2H), 4.00 (td, J = 10.6, 2.5 Hz, 1H), 3.88 (s, 3H), 3.66 (t, J = 10.0 Hz, 1H), 3.57 (q, J = 7.0 Hz, 2H), 3.43 (ddd, J = 9.3, 4.5, 2.2 Hz, 1H), 3.08-2.96 (m, 1H), 2.87 (dd, J = 15.7, 10.9 Hz, 1H), 2.76 (dd, J = 15.8, 3.8 Hz, 1H), 2.67 (dd, J = 15.8, 6.2 Hz, 1H), 2.39 (tdd, J = 9.9, 6.2, 3.8 Hz, 1H), 2.34-2.25 (m, 1H), 1.59 (dddd, J = 14.1, 10.8, 9.7, 2.2 Hz, 1H), 1.37 (d, J = 6.5 Hz, 3H), 1.21 (t, J = 7.0 Hz, 3H) |
| 45 | — | — | HRMS-ESI (m/z) [M + H]$^+$ calcd for C$_{32}$H$_{44}$N$_2$O$_9$, 601.312; found, 601.3108 | $^1$H NMR (400 MHz, CDCl$_3$) δ 8.43 (d, J = 8.0 Hz, 1H), 8.29 (d, J = 5.4 Hz, 1H), 7.36-7.25 (m, 2H), 7.23-7.16 (m, 3H), 6.95 (d, J = 5.4 Hz, 1H), 5.83 (s, 2H), 5.09 (dq, J = 9.6, 6.5 Hz, 1H), 4.63 (dt, J = 10.2, 7.8 Hz, 1H), 4.10 (s, 2H), 3.91 (s, 3H), 3.70-3.50 (m, 5H), 2.83 (ddd, J = 13.9, 9.0, 4.8 Hz, 1H), 2.58 (dt, J = 13.8, 8.3 Hz, 1H), 2.44 (ddd, J = 14.0, 7.6, 3.6 Hz, 1H), 1.94-1.69 (m, 4H), 1.31 (d, J = 6.5 Hz, 3H), 1.28-1.12 (m, 7H), 1.09 (ddt, J = 14.9, 7.3, 4.6 Hz, 2H), 0.84 (t, J = 7.2 Hz, 3H) $^{13}$C NMR (101 MHz, CDCl$_3$) δ 172.11, 170.04, 163.02, 160.10, 145.90, 143.74, 142.50, 141.84, 128.43, 128.40, 125.93, 109.65, 89.53, 79.42, 74.94, 67.80, 67.19, 57.66, 56.22, 50.09, 43.37, 34.12, 32.24, 31.46, 27.85, 27.48, 23.32, 19.39, 15.02, 13.81 |
| 46 | — | (Thin Film) 3377, 2933, 1745, 1676, 1505, 1376, 1210 | HRMS-ESI (m/z) [M]$^+$ calcd for C$_{26}$H$_{40}$N$_2$O$_9$, 524.2734; found, 524.2741 | $^1$H NMR (400 MHz, CDCl$_3$) δ 8.42 (d, J = 8.0 Hz, 1H), 8.28 (d, J = 5.4 Hz, 1H), 6.95 (d, J = 5.4 Hz, 1H), 5.82 (s, 2H), 5.17-5.05 (m, 1H), 4.66-4.55 (m, 1H), 4.10 (s, 2H), 3.90 (s, 3H), 3.64-3.53 (m, 3H), 3.51-3.42 (m, 2H), 2.46-2.34 (m, 1H), 1.84-1.41 (m, 4H), 1.33 (d, J = 6.5 Hz, 3H), 1.30-1.10 (m, 6H), 1.23 (t, J = 7.0 Hz, 3H), 0.98 (t, J = 7.3 Hz, 3H), 0.89 (t, J = 6.9 Hz, 3H) $^{13}$C NMR (101 MHz, CDCl$_3$) δ 172.10, 170.00, 162.99, 160.07, 145.89, 143.68, 142.50, 109.64, 89.49, 82.05, 74.98, 67.77, 67.15, 57.41, 56.20, 50.10, 43.62, 34.12, 27.97, 27.77, 23.36, 22.69, 19.38, 15.00, 13.85, 10.83 |

TABLE 2-continued

Analytical Data

| Compound Number | MP (° C.) | IR (cm$^{-1}$) | MASS | NMR ($^1$H, $^{13}$H, $^{19}$F) |
|---|---|---|---|---|
| 47 | — | (Thin Film) 3371, 1745, 1675, 1498, 1377, 1219 | HRMS-ESI (m/z) [M + H]$^+$ calcd for C$_{30}$H$_{43}$N$_2$O$_{10}$, 603.2918; found, 603.2905 | $^1$H NMR (400 MHz, CDCl$_3$) δ 8.41 (d, J = 8.0 Hz, 1H), 8.28 (d, J = 5.4 Hz, 1H), 7.33-7.28 (m, 2H), 7.00-6.91 (m, 4H), 5.82 (s, 2H), 5.25-5.13 (m, 1H), 4.70-4.59 (m, 1H), 4.21-4.06 (m, 2H), 4.09 (s, 2H), 4.05-3.98 (m, 1H), 3.91-3.83 (m, 1H), 3.90 (s, 3H), 3.64-3.56 (m, 1H), 3.59 (q, 7.0 0 Hz, 2H), 2.41-2.31 (m, 1H), 2.29-2.19 (m, 1H), 1.81-1.67 (m, 1H), 1.39 (d, J = 6.5 Hz, 3H), 1.37-1.15 (m, 6H), 1.22 (t, J = 7.0 Hz, 3H), 0.88 (t, J = 6.8 Hz, 3H) $^{13}$C NMR (101 MHz, CDCl$_3$) δ 172.07, 170.03, 162.99, 160.10, 158.36, 145.88, 143.74, 142.44, 129.53, 121.15, 114.53, 109.68, 89.49, 78.31, 74.62, 67.78, 67.38, 67.16, 60.46, 56.22, 50.27, 39.98, 34.24, 27.55, 27.25, 23.34, 19.30, 15.01, 13.85 |
| 48 | — | (Thin Film) 3380, 2975, 2929, 2871, 1785, 1739, 1676, 1507 | HRMS-ESI (m/z) [M + H]$^+$ calcd for C$_{26}$H$_{33}$N$_2$O$_8$, 501.2231; found, 501.2239 | $^1$H NMR (400 MHz, CDCl$_3$) δ 8.75 (d, J = 7.6 Hz, 1H), 8.36 (d, J = 5.4 Hz, 1H), 7.32-7.27 (m, 2H), 7.26-7.22 (m, 2H), 7.22-7.17 (m, 1H), 7.01 (d, J = 5.5 Hz, 1H), 5.18 (qd, J = 6.6, 3.6 Hz, 1H), 4.65 (td, J = 7.8, 5.4 Hz, 1H), 4.48 (d, J = 0.6 Hz, 2H), 3.95-3.91 (m, 1H), 3.89 (s, 3H), 3.73 (q, J = 7.0 Hz, 2H), 3.63 (dd, J = 10.7, 4.2 Hz, 1H), 3.49 (dd, J = 10.8, 2.6 Hz, 1H), 3.43 (ddd, J = 11.3, 7.6, 2.5 Hz, 1H), 2.87 (dd, J = 13.5, 7.7 Hz, 1H), 2.77 (dd, J = 13.5, 8.4 Hz, 1H), 2.45 (dddd, J = 14.4, 7.7, 5.4, 2.5 Hz, 1H), 1.92-1.84 (m, 1H), 1.84-1.76 (m, 1H), 1.28 (t, J = 7.0 Hz, 3H), 1.24 (d, J = 6.6 Hz, 3H) |
| 49 | — | (Thin Film) 3367, 3026, 2971, 2929, 2870, 1738, 1648, 1526 | HRMS-ESI (m/z) [M + H]$^+$ calcd for C$_{22}$H$_{27}$N$_2$O$_6$, 415.1864; found, 415.1867 | $^1$H NMR (400 MHz, CDCl$_3$) δ 12.13 (s, 1H), 8.74 (d, J = 7.5 Hz, 1H), 8.00 (d, J = 5.2 Hz, 1H), 7.33-7.22 (m, 4H), 7.22-7.17 (m, 1H), 6.87 (d, J = 5.2 Hz, 1H), 5.20 (qd, J = 6.6, 3.6 Hz, 1H), 4.68 (td, J = 7.8, 5.4 Hz, 1H), 3.99-3.94 (m, 1H), 3.93 (s, 3H), 3.65 (dd, J = 10.8, 4.3 Hz, 1H), 3.50 (dd, J = 10.8, 2.6 Hz, 1H), 3.48-3.44 (m, 1H), 2.88 (dd, J = 13.5, 7.7 Hz, 1H), 2.77 (dd, J = 13.5, 8.4 Hz, 1H), 2.49 (dddd, J = 14.4, 7.7, 5.4, 2.5 Hz, 1H), 1.93 (dtd, J = 14.3, 7.9, 2.7 Hz, 1H), 1.83 (ttd, J = 8.0, 4.0, 2.5 Hz, 1H), 1.26 (d, J = 6.6 Hz, 3H) |
| 50 | 52-56 | — | HRMS-ESI (m/z) [M + H]$^+$ calcd for C$_{25}$H$_{33}$N$_2$O$_6$, 457.2333; found, 457.2335 | $^1$H NMR (400 MHz, CDCl$_3$) δ 12.12 (s, 1H), 8.58 (d, J = 8.1 Hz, 1H), 7.99 (d, J = 5.1 Hz, 1H), 7.33-7.27 (m, 2H), 7.23-7.14 (m, 3H), Hz, 1H), 4.60 (dt, J = 10.3, 7.7 Hz, 1H), 3.93 (s, 3H), 3.66 (dd, J = 11.1, 9.4 Hz, 1H), 3.60-3.41 (m, 2H), 2.63 (dd, J = 15.7, 3.4 Hz, 1H), 2.52 (dd, J = 15.8, 6.7 Hz, 1H), 2.39 (ddd, J = 14.0, 7.5, 3.7 Hz, 1H), 2.23 (tdd, J = 9.8, 6.7, 3.3 Hz, 1H), 1.82-1.44 (m, 3H), 1.30 (d, J = 6.6 Hz, 3H), 0.89 (t, J = 7.1 Hz, 3H) |
| 51 | — | (Thin Film) 3367, 2935, 2872, 1743, 1649, 1527, 1436 | HRMS-ESI (m/z) [M + H]$^+$ calcd for C$_{26}$H$_{35}$N$_2$O$_6$, 471.2490; found, 471.2499 | $^1$H NMR (400 MHz, CDCl$_3$) δ 12.13 (s, 1H), 8.59 (d, J = 8.0 Hz, 1H), 7.98 (d, J = 5.1 Hz, 1H), 7.29 (t, J = 7.3 Hz, 2H), 7.24-7.14 (m, 3H), 6.86 (d, J = 5.2 Hz, 1H), 5.19 (dq, J = 9.5, 6.5 Hz, 1H), 4.60 (dt, J = 10.3, 7.7 Hz, 1H), 3.93 (s, 3H), 3.69-3.61 (m, 1H), 3.58-3.41 (m, 2H), 2.62 (dd, J = 15.8, 3.2 Hz, 1H), 2.52 (dd, J = 15.8, 6.6 Hz, 1H), 2.44-2.34 (m, 1H), 2.23 (tdd, J = 9.9, 6.6, 3.5 Hz, 1H), 1.82-1.66 (m, 1H), 1.66-1.52 (m, 2H), 1.51-1.38 (m, 1H), 1.36-1.32 (m, 1H), 1.30 (d, J = 6.5 Hz, 3H), 1.28-1.17 (m, 2H), 0.88 (t, J = 7.0 Hz, 3H) |
| 52 | — | (Thin Film) 3366, 2936, 1743, 1648, 1575, 1496, 1436 | HRMS-ESI (m/z) [M + H]$^+$ calcd for C$_{29}$H$_{33}$N$_2$O$_6$, 505.2333; found, 505.2341 | $^1$H NMR (400 MHz, CDCl$_3$) δ 12.11 (s, 1H), 8.53 (d, J = 8.1 Hz, 1H), 7.96 (d, J = 5.2 Hz, 1H), 7.34-7.27 (m, 2H), 7.24 (td, J = 7.4, 1.5 Hz, 4H), 7.23-7.13 (m, 4H), 6.83 (d, J = 5.2 Hz, 1H), 5.22 (dq, J = 9.5, 6.5 Hz, 1H), 4.60 (dt, J = 9.4, 7.4 Hz, 1H), 4.01 (td, J = 10.6, 2.5 Hz, 1H), 3.91 (s, 3H), 3.65 (t, J = 9.9 Hz, 1H), 3.43 (ddd, J = 9.5, 4.7, 2.2 Hz, 1H), 3.02 (dd, J = 15.8, 2.5 Hz, 1H), 2.85 (dd, J = 15.7, 10.9 |

TABLE 2-continued

Analytical Data

| Compound Number | MP (° C.) | IR (cm$^{-1}$) | MASS | NMR ($^1$H, $^{13}$H, $^{19}$F) |
|---|---|---|---|---|
| | | | | Hz, 1H), 2.76 (dd, J = 15.9, 3.9 Hz, 1H), 2.67 (dd, J = 15.8, 6.1 Hz, 1H), 2.40 (tdd, J = 9.9, 6.2, 3.9 Hz, 1H), 2.32-2.22 (m, 1H), 1.71-1.52 (m, 1H), 1.38 (d, J = 6.4 Hz, 3H) |
| 53 | — | (Thin Film) 3362, 2935, 2876, 1742, 1649, 1528, 1436 | HRMS-ESI (m/z) [M + H]$^+$ calcd for C$_{25}$H$_{33}$N$_2$O$_7$, 473.2282; found 473.2278 | $^1$H NMR (400 MHz, CDCl$_3$) δ 12.11 (s, 1H), 8.59 (d, J = 8.0 Hz, 1H), 7.99 (d, J = 5.2 Hz, 1H), 7.29 (t, J = 7.3 Hz, 2H), 7.20 (t, J = 8.0 Hz, 3H), 6.86 (d, J = 5.2 Hz, 1H), 5.17 (dq, J = 9.6, 6.5 Hz, 1H), 4.61 (dt, J = 10.1, 7.7 Hz, 1H), 3.94 (s, 3H), 3.75-3.63 (m, 2H), 3.60-3.51 (m, 1H), 3.50-3.35 (m, 2H), 3.31 (s, 3H), 2.63 (dd, J = 15.9, 3.5 Hz, 1H), 2.53 (dd, J = 15.9, 6.4 Hz, 1H), 2.46-2.35 (m, 1H), 2.29 (tdd, J = 9.9, 6.4, 3.5 Hz, 1H), 1.98 (dtd, J = 15.4, 7.9, 2.2 Hz, 1H), 1.92-1.82 (m, 1H), 1.82-1.70 (m, 1H), 1.31 (d, J = 6.5 Hz, 3H) |
| 54 | — | — | HRMS-ESI (m/z) [M + H]$^+$ calcd for C$_{22}$H$_{26}$FN$_2$O$_6$, 433.1769; found, 433.1773 | $^1$H NMR (400 MHz, CDCl$_3$) δ 12.12 (s, 1H), 8.73 (d, J = 7.6 Hz, 1H), 8.01 (d, J = 5.2 Hz, 1H), 7.21 (dd, J = 8.4, 5.6 Hz, 2H), 6.97 (t, J = 8.7 Hz, 2H), 6.88 (d, J = 5.2 Hz, 1H), 5.18 (qd, J = 6.6, 3.1 Hz, 1H), 4.68 (td, J = 7.8, 5.3 Hz, 1H), 4.02-3.95 (m, 1H), 3.94 (s, 3H), 3.65 (dd, J = 10.7, 4.0 Hz, 1H), 3.53-3.41 (m, 2H), 2.86 (dd, J = 13.6, 7.9 Hz, 1H), 2.77 (dd, J = 13.7, 8.4 Hz, 1H), 2.49 (dddd, J = 15.0, 7.7, 5.4, 2.5 Hz, 1H), 1.94 (dtd, J = 14.3, 7.8, 2.7 Hz, 1H), 1.74 (ttd, J = 7.7, 3.7, 2.4 Hz, 1H), 1.26 (d, J = 6.6 Hz, 3H) $^{19}$F NMR (376 MHz, CDCl$_3$) δ −117.15 |
| 55 | — | — | HRMS-ESI (m/z) [M + H]$^+$ calcd for C$_{24}$H$_{30}$FN$_2$O$_6$, 461.2082; found, 461.2074 | $^1$H NMR (400 MHz, CDCl$_3$) δ 12.13 (s, 1H), 8.59 (d, J = 8.0 Hz, 1H), 7.99 (d, J = 5.2 Hz, 1H), 7.13 (dd, J = 8.5, 5.4 Hz, 2H), 6.98 (t, J = 8.6 Hz, 2H), 6.87 (d, J = 5.3 Hz, 1H), 5.18 (dq, J = 9.4, 6.5 Hz, 1H), 4.61 (dt, J = 10.1, 7.7 Hz, 1H), 3.93 (s, 3H), 3.65 (dd, J = 11.2, 9.3 Hz, 1H), 3.59-3.50 (m, 1H), 3.42 (td, J = 10.2, 2.8 Hz, 1H), 2.60 (dd, J = 15.7, 3.7 Hz, 1H), 2.51 (dd, J = 15.8, 6.5 Hz, 1H), 2.40 (ddd, J = 13.7, 7.5, 3.9 Hz, 1H), 2.18 (tdd, J = 9.9, 6.6, 3.6 Hz, 1H), 1.83-1.70 (m, 1H), 1.70-1.55 (m, 2H), 1.29 (d, J = 6.5 Hz, 3H), 0.96 (t, J = 7.3 Hz, 3H) $^{19}$F NMR (376 MHz, CDCl$_3$) δ −116.79 |
| 56 | — | — | HRMS-ESI (m/z) [M + H]$^+$ calcd for C$_{26}$H$_{34}$FN$_2$O$_6$, 489.2395; found, 489.2376 | $^1$H NMR (400 MHz, CDCl$_3$) δ 12.11 (s, 1H), 8.58 (d, J = 8.1 Hz, 1H), 7.99 (d, J = 5.2 Hz, 1H), 7.14 (dd, J = 8.5, 5.5 Hz, 2H), 6.99 (t, J = 8.6 Hz, 2H), 6.86 (d, J = 5.2 Hz, 1H), 5.18 (dq, J = 9.4, 6.5 Hz, 1H), 4.60 (dt, J = 10.3, 7.7 Hz, 1H), 3.94 (s, 3H), 3.70-3.58 (m, 1H), 3.57-3.44 (m, 2H), 2.65-2.55 (m, 1H), 2.51 (dd, J = 15.8, 6.6 Hz, 1H), 2.39 (ddt, J = 13.4, 7.6, 3.7 Hz, 1H), 2.18 (dddd, J = 12.7, 9.9, 6.5, 3.5 Hz, 1H), 1.80-1.69 (m, 1H), 1.69-1.49 (m, 2H), 1.49-1.40 (m, 1H), 1.29 (d, J = 6.5 Hz, 3H), 1.36-1.21 (m, 3H), 0.88 (t, J = 7.0 Hz, 3H) $^{19}$F NMR (376 MHz, CDCl$_3$) δ −116.81 |
| 57 | — | — | HRMS-ESI (m/z) [M + H]$^+$ calcd for C$_{30}$H$_{34}$FN$_2$O$_6$, 537.2395; found, 537.2375 | $^1$H NMR (400 MHz, CDCl$_3$) δ 12.11 (s, 1H), 8.59 (d, J = 8.0 Hz, 1H), 8.00 (d, J = 5.2 Hz, 1H), 7.29-7.25 (m, 2H), 7.22-7.17 (m,1H), 7.17-7.12 (m, 2H), 7.01 (dd, J = 8.5, 5.5 Hz, 2H), 6.92 (t, J = 8.6 Hz, 2H), 6.87 (d, J = 5.2 Hz, 1H), 5.15 (dq, J = 9.5, 6.5 Hz, 1H), 4.62 (dt, J = 10.4, 7.7 Hz, 1H), 3.94 (s, 3H), 3.76-3.67 (m, 1H), 3.67-3.60 (m, 1H), 3.54 (td, J = 10.6, 2.4 Hz, 1H), 2.79 (ddd, J = 13.7, 8.9, 4.7 Hz, 1H), 2.63-2.38 (m, 4H), 2.24-2.13 (m, 1H), 2.00-1.75 (m, 3H), 1.30 (d, J = 6.5 Hz, 3H) $^{19}$F NMR (376 MHz, CDCl$_3$) δ −116.71 |
| 58 | — | — | HRMS-ESI (m/z) [M + H]$^+$ calcd for | $^1$H NMR (400 MHz, CDCl$_3$) δ 12.10 (d, J = 0.6 Hz, 1H), 8.58 (d, J = 8.0 Hz, 1H), 8.00 (d, J = 5.2 Hz, 1H), 7.15 (dd, J = 8.6, 5.4 Hz, 2H), 6.99 (t, J = 8.6 Hz, 2H), 6.87 (d, J = 5.2 Hz, |

TABLE 2-continued

Analytical Data

| Compound Number | MP (° C.) | IR (cm$^{-1}$) | MASS | NMR ($^1$H, $^{13}$H, $^{19}$F) |
|---|---|---|---|---|
| | | | C$_{25}$H$_{32}$FN$_2$O$_7$, 491.2188; found, 491.2197 | 1H), 5.15 (dq, J = 9.5, 6.5 Hz, 1H), 4.61 (dt, J = 10.0, 7.6 Hz, 1H), 3.94 (s, 3H), 3.76-3.63 (m, 2H), 3.54 (ddd, J = 9.4, 4.3, 2.4 Hz, 1H), 3.52-3.34 (m, 2H), 3.32 (s, 3H), 2.64-2.55 (m, 1H), 2.51 (dd, J = 15.9, 6.3 Hz, 1H), 2.46-2.36 (m, 1H), 2.22 (tdd, J = 9.9, 6.4, 3.6 Hz, 1H), 1.91 (dddt, J = 21.1, 10.6, 8.6, 5.1 Hz, 2H), 1.76 (dddd, J = 13.7, 11.0, 9.8, 2.4 Hz, 1H), 1.30 (d, J = 6.5 Hz, 3H) $^{19}$F NMR (376 MHz, CDCl$_3$) δ −116.78 |
| 59 | 91-93 | — | HRMS-ESI (m/z) [M + H]$^+$ calcd for C$_{28}$H$_{39}$N$_2$O$_6$, 499.2803; found, 499.2811 | $^1$H NMR (400 MHz, CDCl$_3$) δ 12.15 (d, J = 0.6 Hz, 1H), 8.60 (d, J = 8.1 Hz, 1H), 8.00 (d, J = 5.2 Hz, 1H), 7.33-7.24 (m, 2H), 7.23-7.15 (m, 3H), 6.87 (d, J = 5.2 Hz, 1H), 5.11 (dq, J = 9.6, 6.4 Hz, 1H), 4.67-4.56 (m, 1H), 3.94 (s, 3H), 3.70-3.53 (m, 3H), 2.82 (ddd, J = 13.6, 8.7, 4.6 Hz, 1H), 2.65-2.53 (m, 1H), 2.48-2.37 (m, 1H), 1.90-1.73 (m, 4H), 1.41-1.16 (m, 6H), 1.02-0.89 (m, 2H), 0.82 (d, J = 6.5 Hz, 3H), 0.80 (d, J = 6.6 Hz, 3H) |
| 60 | 86-88 | — | HRMS-ESI (m/z) [M + H]$^+$ calcd for C$_{28}$H$_{38}$FN$_2$O$_6$, 517.2708; found, 517.2693 | $^1$H NMR (400 MHz, CDCl$_3$) δ 12.14 (s, 1H), 8.60 (d, J = 8.1 Hz, 1H), 8.00 (d, J = 5.2 Hz, 1H), 7.17-7.11 (m, 2H), 7.01-6.93 (m, 2H), 6.87 (dd, J = 5.3, 0.7 Hz, 1H), 5.10 (dq, J = 9.6, 6.5 Hz, 1H), 4.61 (app dt, J = 10.2, 7.8 Hz, 1H), 3.94 (s, 3H), 3.70-3.50 (m, 3H), 2.78 (ddd, J = 13.4, 8.5, 4.5 Hz, 1H), 2.63-2.51 (m, 1H), 2.48-2.37 (m, 1H), 1.91-1.67 (m, 4H), 1.41-1.15 (m, 6H), 1.02-0.88 (m, 2H), 0.82 (d, J = 6.6 Hz, 3H), 0.79 (d, J = 6.6 Hz, 3H) |
| 61 | 66-72 | — | HRMS-ESI (m/z) [M + H]$^+$ calcd for C$_{28}$H$_{31}$N$_2$O$_6$, 491.2177; found, 491.2184 | $^1$H NMR (400 MHz, CDCl$_3$) δ 12.12 (d, J = 0.6 Hz, 1H), 8.70 (d, J = 7.5 Hz, 1H), 8.00 (d, J = 5.2 Hz, 1H), 7.44-7.17 (m, 9H), 6.86 (dd, J = 5.3, 0.7 Hz, 1H), 4.94 (qd, J = 6.6, 4.3 Hz, 1H), 4.60 (app td, J = 7.6, 5.4 Hz, 1H), 3.93 (s, 3H), 3.83 (ddd, J = 10.8, 7.7, 2.7 Hz, 1H), 3.40-3.22 (m, 3H), 2.91 (dd, J = 13.6, 6.1 Hz, 1H), 2.79 (dd, J = 13.6, 9.4 Hz, 1H), 2.50-2.37 (m, 1H), 1.92-1.79 (m, 1H), 1.45-1.34 (m, 1H), 0.93 (d, J = 6.6 Hz, 3H) |
| 62 | 138-141 | — | HRMS-ESI (m/z) [M + H]$^+$ calcd for C$_{27}$H$_{37}$N$_2$O$_6$, 485.2646; found, 485.2652 | $^1$H NMR (400 MHz, CDCl$_3$) δ 12.13 (s, 1H), 8.54 (d, J = 8.1 Hz, 1H), 7.97 (d, J = 5.2 Hz, 1H), 7.34-7.16 (m, 5H), 6.85 (d, J = 5.2 Hz, 1H), 5.16 (dq, J = 9.6, 6.4 Hz, 1H), 4.60 (dt, J = 9.5, 7.8 Hz, 1H), 4.04 (td, J = 10.5, 2.9 Hz, 1H), 3.92 (s, 3H), 3.60 (app t, J = 9.9 Hz, 1H), 3.40 (ddd, J = 9.6, 4.7, 2.4 Hz, 1H), 2.94 (dd, J = 15.6, 2.9 Hz, 1H), 2.83 (dd, J = 15.5, 10.5 Hz, 1H), 2.28 (dtt, J = 12.2, 4.9, 2.5 Hz, 1H), 1.95 (tt5J = 10.1, 3.8 Hz, 1H), 1.71-1.57 (m, 1H), 1.51-1.34 (m, 6H), 1.32-1.12 (m, 2H), 0.89 (d, J = 6.5 Hz, 3H), 0.88 (d, J = 6.5 Hz, 3H) |
| 63 | 49-53 | — | HRMS-ESI (m/z) [M + H]$^+$ calcd for C$_{20}$H$_{31}$N$_2$O$_6$, 395.2177; found, 395.2176 | $^1$H NMR (400 MHz, CDCl$_3$) δ 12.13 (d, J = 0.6 Hz, 1H), 8.69 (d, J = 7.6 Hz, 1H), 7.99 (d, J = 5.2 Hz, 1H), 6.87 (dd, J = 5.2, 0.7 Hz, 1H), 5.13 (qd, J = 6.6, 5.0 Hz, 1H), 4.65 (app td, J = 7.9, 5.7 Hz, 1H), 3.94 (s, 3H), 3.86 (ddd, J = 10.9, 7.0, 2.7 Hz, 1H), 3.64 (dd, J = 11.1, 5.5 Hz, 1H), 3.58 (dd, J = 11.0, 3.4 Hz, 1H), 3.52 (ddd, J = 10.8, 8.1, 2.3 Hz, 1H), 2.48 (dddd, J = 14.4, 6.9, 5.8, 2.3 Hz, 1H), 1.95-1.82 (m, 1H), 1.66-1.31 (m, 7H), 1.24-1.10 (m, 2H), 0.89 (app dd, J = 6.6, 4.0 Hz, 6H) |
| 64 | — | — | HRMS-ESI (m/z) [M + H]$^+$ calcd for C$_{24}$H$_{37}$N$_2$O$_6$, 485.2646; found, 485.2648 | $^1$H NMR (400 MHz, CDCl$_3$) δ 12.15 (s, 1H), 8.60 (d, J = 8.1 Hz, 1H), 7.99 (d, J = 5.2 Hz, 1H), 7.32-7.25 (m, 2H), 7.23-7.15 (m, 3H), 6.86 (d, J = 5.2 Hz, 1H), 5.11 (dq, J = 9.6, 6.4 Hz, 1H), 4.62 (dt, J = 10.2, 7.8 Hz, 1H), 3.93 (s, 3H), 3.71-3.53 (m, 3H), 2.83 (ddd, J = 13.9, 8.8, 4.9 Hz, 1H), 2.59 (dt, J = 13.8, 8.3 Hz, 1H), 2.49-2.36 (m, 1H), 1.82 (m, 4H), 1.32 (d, J = 6.5 Hz, 3H), 1.29-1.14 (m, 4H), 1.14-1.03 (m, 2H), 0.84 (t, J = 7.2 Hz, 3H) |

TABLE 2-continued

Analytical Data

| Compound Number | MP (° C.) | IR (cm$^{-1}$) | MASS | NMR ($^1$H, $^{13}$H, $^{19}$F) |
|---|---|---|---|---|
| | | | | $^{13}$C NMR (101 MHz, CDCl$_3$) δ 171.50, 168.76, 155.30, 148.69, 141.77, 140.56, 130.47, 128.42, 128.41, 125.95, 109.45, 79.42, 75.20, 57.55, 56.06, 49.78, 43.34, 33.95, 32.20, 31.43, 27.82, 27.44, 23.31, 19.39, 13.80 |
| 65 | — | (Thin Film) 3362, 2952, 2939, 2871, 1730, 1649 | HRMS-ESI (m/z) [M + H]$^+$ calcd for C$_{24}$H$_{36}$N$_2$O$_8$, 481.2544; found, 481.2548 | $^1$H NMR (400 MHz, CDCl$_3$) δ 12.11 (d, J = 0.7 Hz, 1H), 8.58 (d, J = 8.1 Hz, 1H), 8.00 (d, J = 5.2 Hz, 1H), 6.87 (dd, J = 5.3, 0.6 Hz, 1H), 5.15 (dq, J = 9.6, 6.4 Hz, 1H), 4.63 (dt, J = 9.6, 7.5 Hz, 1H), 4.30 (dd, J = 12.5, 2.6 Hz, 1H), 4.21 (dd, J = 12.5, 7.7 Hz, 1H), 3.94 (s, 3H), 3.90 (ddd, J = 10.5, 7.7, 2.5 Hz, 1H), 3.83-3.72 (m, 1H), 3.56 (ddd, J = 9.5, 4.6, 2.4 Hz, 1H), 2.60 (p, J = 7.0 Hz, 1H), 2.45-2.35 (m, 1H), 1.99 (td, J = 10.2, 9.2, 4.0 Hz, 1H), 1.78 (dddd, J = 14.2, 10.7, 9.6, 2.4 Hz, 1H), 1.38 (d, J = 6.5 Hz, 3H), 1.36-1.22 (m, 6H), 1.19 (app dd, J = 7.0, 0.9 Hz, 6H), 0.90 (t, J = 7.2 Hz, 3H) |
| 66 | — | (Thin Film) 3367, 2929, 2870, 1741, 1650 | HRMS-ESI (m/z) [M + H]$^+$ calcd for C$_{19}$H$_{28}$N$_2$O$_6$, 381.202; found, 381.2013 | $^1$H NMR (400 MHz, CDCl$_3$) δ 12.13 (s, 1H), 8.69 (d, J = 7.6 Hz, 1H), 7.99 (dd, J = 5.2, 1.0 Hz, 1H), 6.86 (d, J = 5.2 Hz, 1H), 5.18-5.07 (m, 1H), 4.65 (td, J = 7.9, 5.7 Hz, 1H), 3.94 (d, J = 0.8 Hz, 3H), 3.86 (ddd, J = 10.3, 2.7 Hz, 1H), 3.67-3.47 (m, 3H), 2.48 (dtd, J = 16.7, 6.4, 2.3 Hz, 1H), 1.88 (dtd, J = 14.3, 8.0, 2.5 Hz, 1H), 1.63 (ddp, J = 8.8, 5.5, 3.3, 2.8 Hz, 1H), 1.45 (dtd, J = 17.4, 8.9, 5.8 Hz, 1H), 1.34 (d, J = 6.6 Hz, 3H), 1.32-1.22 (m, 5H), 0.90 (d, J = 7.2 Hz, 3H) |
| 67 | 44-46 | (Thin Film) 3365, 2934, 1744, 1650, 1529, 1438, 1282 | HRMS-ESI (m/z) [M]$^+$ calcd for C$_{21}$H$_{32}$N$_2$O$_6$, 408.2260; found, 408.2253 | $^1$H NMR (400 MHz, CDCl$_3$) δ 12.14 (s, 1H), 8.59 (d, J = 8.1 Hz, 1H), 7.99 (d, J = 5.2 Hz, 1H), 6.86 (d, J = 5.9 Hz, 1H), 5.19-5.07 (m, 1H), 4.66-4.54 (m, 1H), 3.94 (s, 3H), 3.64-3.55 (m, 1H), 3.53-3.42 (m, 2H), 2.45-2.33 (m, 1H), 1.84-1.71 (m, 2H), 1.66-1.43 (m, 2H), 1.34 (d, J = 6.5 Hz, 3H), 1.32-1.09 (m, 6H), 0.98 (t, J = 7.3 Hz, 3H), 0.89 (t, J = 6.8 Hz, 3H) $^{13}$C NMR (101 MHz, CDCl$_3$) δ 171.51, 168.74, 155.26, 148.65, 140.56, 130.49, 109.41, 82.12, 75.27, 57.32, 56.05, 49.80, 43.62, 33.98, 27.96, 27.77, 23.37, 22.71, 19.40, 13.86, 10.83 |
| 68 | 77-79 | (Thin Film) 3366, 2933, 1744, 1649, 1529, 1481, 1242 | HRMS-ESI (m/z) [M]$^+$ calcd for C$_{26}$H$_{34}$N$_2$O$_7$, 486.2366; found, 486.2367 | $^1$H NMR (400 MHz, CDCl$_3$) δ 12.13 (s, 1H), 8.57 (d, J = 8.1 Hz, 1H), 8.00 (d, J = 5.2 Hz, 1H), 7.35-7.25 (m, 2H), 7.02-6.90 (m, 3H), 6.86 (d, J = 5.9 Hz, 1H), 5.26-5.15 (m, 1H), 4.69-4.59 (m, 1H), 4.23-4.07 (m, 2H), 4.07-3.98 (m, 1H), 3.93 (s, 3H), 3.93-3.86 (m, 1H), 3.66-3.58 (m, 1H), 2.41-2.31 (m, 1H), 2.31-2.20 (m, 1H), 1.86-1.72 (m, 1H), 1.40 (d, J = 6.5 Hz, 3H), 1.37-1.16 (m, 6H), 0.88 (t, J = 6.8 Hz, 3H) $^{13}$C NMR (101 MHz, CDCl$_3$) δ 171.48, 168.73, 158.34, 155.29, 148.68, 140.55, 130.47, 129.56, 121.20, 114.54, 109.45, 78.39, 74.94, 67.43, 60.43, 56.06, 49.97, 39.94, 34.13, 27.52, 27.24, 23.35, 19.32, 13.85 |
| 69 | — | — | ESIMS m/z 264 ([M + H]$^+$) | — |
| 70 | — | — | ESIMS m/z 306 ([M + H]$^+$) | — |
| 71 | — | — | ESIMS m/z 320 ([M + H]$^+$) | — |
| 72 | — | — | ESIMS m/z 354 ([M + H]$^+$) | — |

TABLE 2-continued

Analytical Data

| Compound Number | MP (° C.) | IR (cm$^{-1}$) | MASS | NMR ($^1$H, $^{13}$H, $^{19}$F) |
|---|---|---|---|---|
| 73 | — | — | ESIMS m/z 322 ([M + H]$^+$) | — |
| 74 | — | — | ESIMS m/z 282 ([M + H]$^+$) | — |
| 75 | — | — | ESIMS m/z 310 ([M + H]$^+$) | — |
| 76 | — | — | ESIMS m/z 338 ([M + H]$^+$) | — |
| 77 | — | — | ESIMS m/z 386 ([M + H]$^+$) | — |
| 78 | — | — | ESIMS m/z 340 ([M + H]$^+$) | — |
| 79 | — | — | ESIMS m/z 348 ([M + H]$^+$) | — |
| 80 | — | — | ESIMS m/z 366 ([M + H]$^+$) | — |
| 81 | — | — | ESIMS m/z 340 ([M + H]$^+$) | — |
| 82 | — | — | ESIMS m/z 334 ([M + H]$^+$) | — |
| 83 | — | — | ESIMS m/z 244 ([M + H]$^+$) | — |
| 84 | — | — | ESIMS m/z 334 ([M + H]$^+$) | $^1$H NMR (400 MHz, CDCl$_3$) δ 8.73 (bs, 3H), 7.32-7.22 (m, 2H), 7.17 (td, J = 7.1, 1.3 Hz, 3H), 5.09 (dd, J = 9.7, 6.3 Hz, 1H), 4.07 (t, J = 8.8 Hz, 1H), 3.69-3.46 (m, 3H), 2.79 (dt, J = 13.9, 7.0 Hz, 1H), 2.64 (s, 1H), 2.53 (dt, J = 13.7, 8.2 Hz, 1H), 2.21-2.02 (m, 1H), 1.89-1.64 (m, 5H), 1.32 (d, J = 6.4 Hz, 3H), 1.15 (dt, J = 13.4, 6.8 Hz, 3H), 1.10-1.01 (m, 1H), 0.82 (t, J = 7.2 Hz, 3H) |
| 85 | — | — | ESIMS m/z 330 ([M + H]$^+$) | — |
| 86 | — | — | ESIMS m/z 230 ([M + H]$^+$) | — |
| 87 | 222-224 | (Thin Film) 3403, 2934, 1749, 1515, 1380, 1215 | HRMS-ESI (m/z) ([M + H]$^+$) calcd for C$_{14}$H$_{28}$NO$_3$, 258.2069; found 258.1988 | $^1$H NMR (400 MHz, CDCl$_3$) δ 8.62 (bs, 3H), 5.17-5.03 (m, 1H), 4.17-3.98 (m, 1H), 3.59-3.35 (m, 3H), 2.67-2.51 (m, 1H), 2.18-1.97 (m, 1H), 1.77-1.66 (m, 1H), 1.65-1.38 (m, 2H), 1.34 (d, J = 6.4 Hz, 3H), 1.29-1.06 (m, 6 HH), 0.95 (t, J = 7.2 Hz, 3H), 0.88 (t, J = 6.8, H z, 3H) $^{13}$C NMR (75 MHz, CDCl$_3$) δ 170.13, 82.25, 76.39, 57.65, 50.93, 43.84, 31.77, 28.08, 23.52, 23.04, 19.53, 14.02, 10.93 |
| 88 | 195-197 | (Thin Film) 3396, 2933, 1748, 1598, 1496, 1242 | ESIMS m/z 336.4 ([M + H]$^+$) | $^1$H NMR (400 MHz, CDCl$_3$) δ 8.66 (bs, 3H), 7.31-7.21 (m, 2H), 6.99-6.83 (m, 3H), 5.25-5.09 (m, 1H), 4.23-3.95 (m, 3H), 3.91-3.80 (m, 1H), 3.80-3.73 (m, 1H), 3.68-3.60 (m, 1H), 2.61-2.48 (m, 1H), 2.28-2.04 (m, 2H), 1.38 (d, J = 6.3 Hz, 3H), 1.35-1.09 (m, 6H), 0.84 (t, J = 6.7 Hz, 3H) |
| 89 | — | — | ESIMS m/z 386 ([M + Na]$^+$) | $^1$H NMR (400 MHz, CDCl$_3$) δ 7.33-7.23 (m, 2H), 7.24-7.16 (m, 3H), 5.35 (d, J = 7.4 Hz, 1H), 5.14 (qd, J = 6.6, 3.8 Hz, 1H), 4.29 (td, J = 7.6, 5.1 Hz, 1H), 3.88 (ddd, J = 10.7, 7.6, 2.7 Hz, 1H), 3.59 (dd, J = 10.7, 4.4 Hz, 1H), 3.48-3.35 (m, 2H), 2.83 (dd, J = 13.5, 7.5 Hz, 1H), 2.72 (dd, J = 13.5, 8.6 Hz, 1H), 2.41-2.31 (m, 1H), 1.86-1.67 (m, 2H), 1.45 (s, 9H), 1.24 (d, J = 6.7 Hz, 3H) |

TABLE 2-continued

| | | | Analytical Data | |
|---|---|---|---|---|
| Compound Number | MP (° C.) | IR (cm$^{-1}$) | MASS | NMR ($^1$H, $^{13}$H, $^{19}$F) |
| 90 | — | — | ESIMS m/z 428 ([M + Na]$^+$) | $^{13}$C NMR (101 MHz, CDCl$_3$) δ 173.13, 155.13, 139.99, 129.14, 128.39, 126.11, 79.74, 72.99, 68.88, 66.67, 51.40, 45.74, 37.17, 32.74, 28.35, 21.11 $^1$H NMR (600 MHz, CDCl$_3$) δ 7.31 (t, J = 7.6 Hz, 2H), 7.23 (t, J = 7.4 Hz, 1H), 7.19 (d, J = 7.0 Hz, 2H), 5.24-5.08 (m, 2H), 4.23 (q, J = 8.5 Hz, 1H), 3.61-3.56 (m, 1H), 3.52 (td, J = 10.6, 1.9 Hz, 1H), 3.49-3.44 (m, 1H), 2.64 (dd, J = 15.8, 3.2 Hz, 1H), 2.52 (dd, J = 15.8, 6.8 Hz, 1H), 2.29 (ddd, J = 11.8, 7.2, 3.7 Hz, 1H), 2.22 (tdd, J = 10.0, 6.8, 3.2 Hz, 1H), 1.72-1.60 (m, 1H), 1.59-1.48 (m, 4H), 1.46 (s, 9H), 1.30 (d, J = 6.5 Hz, 3H), 0.90 (t, J = 7.2 Hz, 3H) |
| 91 | — | — | ESIMS m/z 420 ([M + H]$^+$) | $^{13}$C NMR (151 MHz, CDCl$_3$) δ 172.57, 155.00, 139.74, 128.72, 128.55, 126.26, 80.87, 79.78, 75.15, 57.90, 51.19, 45.28, 35.01, 34.60, 31.92, 28.35, 20.48, 19.17, 13.92 $^1$H NMR (400 MHz, CDCl$_3$) δ 7.31-7.26 (m, 2H), 7.24-7.19 (m, 1H), 7.18-7.14 (m, 2H), 5.13 (dq, J = 9.5, 6.5, 5.7 Hz, 2H), 4.21 (q, J = 8.6 Hz, 1H), 3.59-3.50 (m, 1H), 3.50-3.38 (m, 2H), 2.60 (dd, J = 15.8, 3.4 Hz, 1H), 2.49 (dd, J = 15.8, 6.6 Hz, 1H), 2.22 (dtdd, J = 19.9, 10.0, 7.1, 3.7 Hz, 2H), 1.61-1.50 (m, 2H), 1.44 (s, 9H), 1.35-1.19 (m, 5H), 1.27 (d, J = 6.5 Hz, 3H), 0.87 (t, J = 7.0 Hz, 3H) $^{13}$C NMR (101 MHz, CDCl$_3$) δ 172.56, 155.00, 139.77, 128.70, 128.55, 126.25, 81.25, 79.78, 75.15, 57.89, 51.19, 45.37, 35.04, 34.59, 29.46, 28.35, 28.15, 22.51, 20.48, 14.02 |
| 92 | — | — | ESIMS m/z 454 ([M + H]$^+$) | $^1$H NMR (400 MHz, CDCl$_3$) δ 7.36-7.24 (m, 3H), 7.25-7.19 (m, 4H), 7.19-7.15 (m, 3H), 5.24-5.12 (m, 1H), 5.10 (d, J = 8.2 Hz, 1H), 4.21 (td, J = 9.3, 8.8, 7.0 Hz, 1H), 3.97 (td, J = 10.6, 2.5 Hz, 1H), 3.59 (t, J = 10.1 Hz, 1H), 3.38 (ddd, J = 9.7, 4.7, 2.4 Hz, 1H), 3.00 (dd, J = 15.9, 2.6 Hz, 1H), 2.84 (dd, J = 15.7, 10.9 Hz, 1H), 2.75 (dd, J = 15.9, 3.8 Hz, 1H), 2.65 (dd, J = 15.8, 6.3 Hz, 1H), 2.36 (tdd, J = 9.9, 6.3, 3.8 Hz, 1H), 2.21-2.10 (m, 1H), 1.50-1.43 (m, 1H), 1.42 (s, 9H), 1.35 (d, J = 6.5 Hz, 3H) $^{13}$C NMR (101 MHz, CDCl$_3$) δ 172.44, 154.96, 139.37, 138.61, 128.77, 128.70, 128.50, 128.44, 126.46, 126.21, 81.69, 79.78, 75.05, 59.21, 51.22, 45.77, 36.37, 35.17, 34.49, 28.33, 20.51 |
| 93 | — | — | ESIMS m/z 444 ([M + Na]$^+$) | $^1$H NMR (400 MHz, CDCl$_3$) δ 7.31-7.24 (m, 2H), 7.22-7.13 (m, 3H), 5.21 (d, J = 8.2 Hz, 1H), 5.11 (dq, J = 9.6, 6.5 Hz, 1H), 4.28-4.15 (m, 1H), 3.66 (td, J = 10.8, 2.2 Hz, 1H), 3.62-3.53 (m, 1H), 3.51-3.42 (m, 2H), 3.42-3.32 (m, 1H), 3.30 (s, 3H), 2.60 (dd, J = 15.9, 3.4 Hz, 1H), 2.49 (dd, J = 15.9, 6.5 Hz, 1H), 2.32-2.17 (m, 2H), 1.98-1.90 (m, 1H), 1.90-1.79 (m, 1H), 1.65-1.50 (m, 1H), 1.43 (s, 9H), 1.27 (d, J = 6.5 Hz, 3H) $^{13}$C NMR (101 MHz, CDCl$_3$) δ 172.34, 154.98, 139.61, 128.70, 128.54, 126.26, 79.73, 78.43, 75.14, 69.34, 58.74, 58.47, 51.11, 45.24, 34.72, 34.46, 30.04, 28.34, 20.43 |
| 94 | — | — | ESIMS m/z 382 ([M + H]$^+$) | $^1$H NMR (400 MHz, CDCl$_3$) δ 7.18 (dd, J = 8.5, 5.6 Hz, 2H), 6.97 (t, J = 8.7 Hz, 2H), 5.32 (d, J = 7.3 Hz, 1H), 5.12 (qd, J = 6.7, 3.4 Hz, 1H), 4.29 (td, J = 7.7, 5.3 Hz, 1H), 3.91 (ddd, J = 10.8, 7.6, 2.7 Hz, 1H), 3.58 (dd, J = 10.7, 4.1 Hz, 1H), 3.45 (dd, J = 10.7, 2.4 Hz, 1H), 3.39 (ddd, J = 11.3, 7.4, 2.6 Hz, 1H), 2.81 (dd, J = 13.6, 7.8 Hz, 1H), 2.73 (dd, J = 13.7, 8.6 Hz, 1H), 2.45-2.27 (m, 1H), 1.73 (dtd, J = 15.9, 7.9, 4.7 Hz, 2H), 1.45 (s, 9H), 1.24 (d, J = 6.6 Hz, 3H) $^{19}$F NMR (376 MHz, CDCl$_3$) δ −117.23 |

TABLE 2-continued

Analytical Data

| Compound Number | MP (° C.) | IR (cm$^{-1}$) | MASS | NMR ($^1$H, $^{13}$H, $^{19}$F) |
|---|---|---|---|---|
| 95 | — | — | ESIMS m/z 432 ([M + Na]$^+$) | $^1$H NMR (400 MHz, CDCl$_3$) δ 7.12 (dd, J = 8.5, 5.4 Hz, 2H), 6.97 (t, J = 8.6 Hz, 2H), 5.19 (d, J = 8.2 Hz, 1H), 5.12 (dq, J = 9.4, 6.5 Hz, 1H), 4.21 (dt, J = 10.4, 7.8 Hz, 1H), 3.55 (dd, J = 11.3, 9.2 Hz, 1H), 3.50-3.43 (m, 1H), 3.38 (td, J = 10.4, 2.8 Hz, 1H), 2.61-2.54 (m, 1H), 2.49 (dd, J = 15.8, 6.5 Hz, 1H), 2.27 (ddd, J = 14.2, 7.5, 3.8 Hz, 1H), 2.14 (tdd, J = 9.9, 6.5, 3.4 Hz, 1H), 1.71-1.51 (m, 3H), 1.44 (s, 9H), 1.27 (d, J = 6.5 Hz, 3H), 0.94 (t, J = 7.2 Hz, 3H) $^{19}$F NMR (376 MHz, CDCl$_3$) δ −116.83 |
| 96 | — | — | ESIMS m/z 460 ([M + Na]$^+$) | $^1$H NMR (400 MHz, CDCl$_3$) δ 7.12 (dd, J = 8.5, 5.4 Hz, 2H), 6.97 (t, J = 8.6 Hz, 2H), 5.21 (d, J = 8.3 Hz, 1H), 5.12 (dq, J = 9.5, 6.5 Hz, 1H), 4.21 (dt, J = 10.6, 7.8 Hz, 1H), 3.55 (dd, J = 11.3, 9.2 Hz, 1H), 3.46 (td, J = 10.2, 2.9 Hz, 2H), 2.57 (dd, J = 15.9, 3.5 Hz, 1H), 2.48 (dd, J = 15.8, 6.6 Hz, 1H), 2.25 (ddd, J = 14.2, 7.3, 3.5 Hz, 1H), 2.14 (ddt, J = 13.0, 6.4, 3.6 Hz, 1H), 1.65-1.49 (m, 3H), 1.45-1.40 (m, 1H), 1.44 (s, 9H), 1.37-1.27 (m, 3H), 1.26 (d, J = 6.5 Hz, 3H), 0.87 (t, J = 7.0 Hz, 3H) $^{19}$F NMR (376 MHz, CDCl$_3$) δ −116.82 |
| 97 | — | — | ESIMS m/z 508 ([M + Na]$^+$) | $^1$H NMR (400 MHz, CDCl$_3$) δ 7.30-7.23 (m, 2H), 7.19 (t, J = 7.3 Hz, 1H), 7.15-7.11 (m, 2H), 6.99 (dd, J = 8.5, 5.5 Hz, 2H), 6.91 (t, J = 8.7 Hz, 2H), 5.23-5.15 (m, 1H), 5.09 (dq, J = 9.5, 6.5 Hz, 1H), 4.23 (dt, J = 10.5, 7.8 Hz, 1H), 3.65-3.45 (m, 3H), 2.77 (ddd, J = 13.8, 9.0, 4.7 Hz, 1H), 2.59-2.49 (m, 1H), 2.44 (td, J = 15.8, 14.9, 5.1 Hz, 2H), 2.30 (ddd, J = 14.6, 7.6, 3.6 Hz, 1H), 2.14 (tdd, J = 9.9, 6.3, 3.6 Hz, 1H), 1.98-1.77 (m, 2H), 1.67-1.55 (m, 1H), 1.44 (s, 9H), 1.27 (d, J = 6.5 Hz, 3H) $^{19}$F NMR (376 MHz, CDCl$_3$) δ −116.69 |
| 98 | — | — | ESIMS m/z 462 ([M + Na]$^+$) | $^1$H NMR (400 MHz, CDCl$_3$) δ 7.14 (dd, J = 8.4, 5.5 Hz, 2H), 6.97 (t, J = 8.6 Hz, 2H), 5.17 (d, J = 8.2 Hz, 1H), 5.10 (dq, J = 9.5, 6.5 Hz, 1H), 4.22 (dt, J = 10.4, 7.8 Hz, 1H), 3.65 (td, J = 10.6, 2.6 Hz, 1H), 3.58 (dd, J = 11.0, 9.3 Hz, 1H), 3.45 (dtd, J = 14.2, 7.1, 6.4, 2.7 Hz, 2H), 3.40-3.33 (m, 1H), 3.31 (s, 3H), 2.58 (dd, J = 16.1, 3.6 Hz, 1H), 2.48 (dd, J = 16.0, 6.4 Hz, 1H), 2.27 (ddd, J = 14.3, 7.6, 4.0 Hz, 1H), 2.18 (tdd, J = 9.9, 6.4, 3.4 Hz, 1H), 1.97-1.79 (m, 2H), 1.63-1.52 (m, 1H), 1.44 (s, 9H), 1.27 (d, J = 6.5 Hz, 3H) $^{19}$F NMR (376 MHz, CDCl$_3$) δ −116.82 |
| 99 | — | — | ESIMS m/z 471 ([M + Na]$^+$) | $^1$H NMR (400 MHz, CDCl$_3$) δ 7.32-7.23 (m, 2H), 7.22-7.14 (m, 3H), 5.22 (d, J = 8.3 Hz, 1H), 5.04 (dq, J = 9.5, 6.5 Hz, 1H), 4.29-4.15 (m, 1H), 3.61-3.46 (m, 3H), 2.80 (ddd, J = 13.7, 8.9, 4.7 Hz, 1H), 2.63-2.50 (m, 1H), 2.34-2.23 (m, 1H), 1.87-1.69 (m, 3H), 1.67-1.56 (m, 1H), 1.44 (s, 9H), 1.40-1.14 (m, 6H), 1.00-0.88 (m, 2H), 0.81 (d, J = 6.6 Hz, 3H), 0.78 (d, J = 6.6 Hz, 3H) $^{13}$C NMR (101 MHz, CDCl$_3$) δ 172.61, 155.02, 141.79, 128.43, 128.40, 125.93, 79.68, 79.00, 74.63, 57.53, 51.14, 43.29, 34.60, 34.01, 32.15, 31.39, 28.60, 28.36, 25.76, 22.44, 22.22, 19.37 |
| 100 | 39-44 | — | ESIMS m/z 489 ([M + Na]$^+$) | $^1$H NMR (400 MHz, CDCl$_3$) δ 7.17-7.09 (m, 2H), 7.00-6.91 (m, 2H), 5.20 (d, J = 8.3 Hz, 1H), 5.04 (dq, J = 9.6, 6.5 Hz, 1H), 4.28-4.16 (m, 1H), 3.60-3.44 (m, 3H), 2.77 (ddd, J = 13.6, 8.7, 4.6 Hz, 1H), 2.55 (app dt, J = 13.9, 8.2 Hz, 1H), 2.29 (ddd, J = 14.1, 7.8, 3.8 Hz, 1H), 1.87-1.65 (m, 3H), 1.67-1.52 (m, 1H), 1.44 (s, 9H), 1.40-1.23 (m, 4H), 1.19 (tdd, J = 9.9, 6.2, 3.7 Hz, 2H), 1.01-0.85 (m, 2H), 0.81 (d, J = 6.6 Hz, 3H), 0.79 (d, J = 6.6 Hz, 3H) |

TABLE 2-continued

Analytical Data

| Compound Number | MP (° C.) | IR (cm$^{-1}$) | MASS | NMR ($^1$H, $^{13}$H, $^{19}$F) |
|---|---|---|---|---|
| 101 | — | — | ESIMS m/z 440 ([M + H]$^+$) | $^1$H NMR (400 MHz, CDCl$_3$) δ 7.44-7.15 (m, 9H), 5.31 (d, J = 7.2 Hz, 1H), 4.87 (qd, J = 6.6, 4.4 Hz, 1H), 4.21 (app td, J = 7.5, 5.2 Hz, 1H), 3.76 (ddd, J = 10.9, 7.9, 2.7 Hz, 1H), 3.32-3.17 (m, 3H), 2.87 (dd, J = 13.6, 6.0 Hz, 1H), 2.74 (dd, J = 13.6, 9.5 Hz, 1H), 2.36-2.24 (m, 1H), 1.73-1.60 (m, 1H), 1.45-1.32 (m, 10H), 0.90 (d, J = 6.6 Hz, 3H) $^{13}$C NMR (101 MHz, CDCl$_3$) δ 173.05, 155.09, 142.06, 141.70, 137.21, 130.78, 130.18, 129.03, 128.21, 127.31, 126.99, 126.32, 79.68, 73.49, 67.98, 66.03, 51.27, 43.83, 34.44, 32.50, 28.36, 20.38 |
| 102 | 41-44 | — | ESIMS m/z 456 ([M + Na]$^+$) | $^1$H NMR (400 MHz, CDCl$_3$) δ 7.30-7.19 (m, 5H), 5.16-5.04 (m, 2H), 4.26-4.15 (m, 1H), 4.01 (td, J = 10.6, 3.1 Hz, 1H), 3.59-3.48 (m, 1H), 3.39-3.30 (m, 1H), 2.98-2.86 (m, 1H), 2.81 (dd, J = 15.5, 10.4 Hz, 1H), 2.21-2.10 (m, 1H), 1.96-1.84 (m, 1H), 1.51-1.32 (m, 16H), 1.30-1.09 (m, 2H), 0.88 (d, J = 6.5 Hz, 3H), 0.86 (d, J = 6.5 Hz, 3H) |
| 103 | 110-112 | — | ESIMS m/z 344 ([M + H]$^+$) | $^1$H NMR (400 MHz, CDCl$_3$) δ 5.29 (d, J = 7.5 Hz, 1H), 5.06 (qd, J = 6.6, 5.2 Hz, 1H), 4.26 (app q, J = 7.1 Hz, 1H), 3.79 (ddd, J = 11.0, 7.1, 2.7 Hz, 1H), 3.59 (dd, J = 11.0, 5.6 Hz, 1H), 3.53 (dd, J = 11.0, 3.5 Hz, 1H), 3.44 (ddd, J = 10.7, 8.0, 2.4 Hz, 1H), 2.41-2.29 (m, 1H), 1.75-1.29 (m, 17H), 1.20-1.09 (m, 2H), 0.87 (app dd, J = 6.6, 4.2 Hz, 6H) |
| 104 | — | — | ESIMS m/z 456 ([M + Na]$^+$) | $^1$H NMR (400 MHz, CDCl$_3$) δ 7.31-7.24 (m, 2H), 7.18 (ddt, J = 7.0, 3.2, 1.4 Hz, 3H), 5.19 (d, J = 8.3 Hz, 1H), 5.05 (dq, J = 9.6, 6.4 Hz, 1H), 4.22 (dt, J = 10.2, 7.7 Hz, 1H), 3.63-3.44 (m, 3H), 2.81 (ddd, J = 14.0, 8.9, 5.2 Hz, 1H), 2.56 (dt, J = 13.9, 8.3 Hz, 1H), 2.29 (ddd, J = 14.3, 7.5, 3.4 Hz, 1H), 1.87-1.69 (m, 3H), 1.67-1.53 (m, 1H), 1.44 (s, 9H), 1.29 (d, J = 6.5 Hz, 3H), 1.23-1.13 (m, 3H), 1.12-1.02 (m, 2H), 0.92-0.86 (m, 1H), 0.83 (t, J = 7.2 Hz, 3H) $^{13}$C NMR (101 MHz, CDCl$_3$) δ 172.63, 155.02, 141.82, 128.39, 125.93, 79.72, 79.37, 74.76, 57.53, 51.13, 43.37, 34.65, 32.25, 31.44, 28.35, 27.83, 27.46, 23.30, 19.39, 13.80 |
| 105 | — | — | ESIMS m/z 430 ([M + H]$^+$) | $^1$H NMR (400 MHz, CDCl$_3$) δ 5.17 (d, J = 8.1 Hz, 1H), 5.10 (dq, J = 9.6, 6.4 Hz, 1H), 4.32-4.15 (m, 3H), 3.86 (ddd, J = 10.7, 7.8, 2.6 Hz, 1H), 3.67 (t, J = 10.1 Hz, 1H), 3.49 (ddd, J = 9.3, 4.3, 2.4 Hz, 1H), 2.65-2.53 (m, 1H), 2.32-2.21 (m, 1H), 1.98-1.88 (m, 1H), 1.76-1.68 (m, 1H), 1.44 (s, 9H), 1.34 (d, J = 6.5 Hz, 3H), 1.31-1.22 (m, 6H), 1.18 (app dd, J = 7.0, 1.1 Hz, 6H), 0.89 (t, J = 7.2 Hz, 3H) $^{13}$C NMR (101 MHz, CDCl$_3$) δ 176.87, 172.49, 154.95, 79.79, 77.74, 74.39, 63.12, 51.19, 40.38, 33.96, 31.58, 28.32, 27.52, 23.28, 22.64, 19.24, 18.96, 18.89, 14.11, 13.80 |
| 106 | — | — | ESIMS m/z 330 ([M + H]$^+$) | $^1$H NMR (400 MHz, CDCl$_3$) δ 5.29 (d, J = 7.5 Hz, 1H), 5.05 (qd, J = 6.6, 5.2 Hz, 1H), 4.26 (td, J = 7.7, 5.6 Hz, 1H), 3.79 (ddd, J = 11.0, 7.1, 2.8 Hz, 1H), 3.65-3.50 (m, 2H), 3.44 (ddd, J = 10.7, 8.1, 2.4 Hz, 1H), 2.35 (dt, J = 14.7, 6.4 Hz, 1H), 1.69 (dtt, J = 14.2, 5.2, 2.7 Hz, 1H), 1.60 (dtd, J = 9.4, 5.6, 3.4 Hz, 1H), 1.44 (s, 9H), 1.41-1.35 (m, 1H), 1.30 (d, J = 6.7 Hz, 3H), 1.29-1.21 (m, 5H), 0.89 (t, J = 7.0 Hz, 3H) $^{13}$C NMR (101 MHz, CDCl$_3$) δ 173.03, 155.09, 79.68, 74.21, 69.67, 65.81, 51.34, 42.95, 33.04, 30.32, 29.45, 28.33, 22.86, 20.72, 14.00 |
| 107 | — | (Thin Film) 3360, 2933, | HRMS-ESI (m/z) [M + Na]$^+$ calcd for | $^1$H NMR (400 MHz, CDCl$_3$) δ 5.26-5.14 (m, 1H), 5.12-5.00 (m, 1H), 4.26-4.16 (m, 1H), 3.55-3.46 (m, 1H), 3.46-3.37 (m, 2H), 2.31-2.19 (m, 1H), 1.80-1.69 (m, 1H), 1.65- |

TABLE 2-continued

Analytical Data

| Compound Number | MP (° C.) | IR (cm$^{-1}$) | MASS | NMR ($^1$H, $^{13}$H, $^{19}$F) |
|---|---|---|---|---|
| | | 1715, 1500, 1367, 1166 | C$_{19}$H$_{35}$NNaO$_5$, 380.2413; found, 380.2330 | 1.43 (m, 3H), 1.44 (s, 9H), 1.31 (d, J = 6.5 Hz, 3H), 1.29-1.09 (m, 6H), 0.96 (t, J = 7.3 Hz, 3H), 0.89 (t, J = 6.8 Hz, 3H) $^{13}$C NMR (75 MHz, CDCl$_3$) δ 172.76, 155.15, 82.12, 79.78, 74.95, 57.45, 51.32, 43.80, 34.80, 28.50, 28.14, 27.93, 23.53, 22.83, 19.55, 14.01, 10.98 |
| 108 | — | (Thin Film) 3357, 2932, 1711, 1497, 1366, 1243, 1162 | HRMS-ESI (m/z) [M]$^+$ calcd for C$_{24}$H$_{37}$NO$_6$, 435.2621; found, 435.2621 | $^1$H NMR (400 MHz, CDCl$_3$) δ 7.35-7.23 (m, 2H), 7.01-6.87 (m, 3H), 5.23(d, J = 7.8 Hz, 1H), 5.20-5.09 (m, 1H), 4.30-4.18 (m, 1H), 4.18-4.03 (m, 2H), 4.03-3.92 (m, 1H), 3.85-3.74 (m, 1H), 3.58-3.50 (m, 1H), 2.29-2.11 (m, 2H), 1.69-1.52 (m, 1H), 1.43 (s, 9H), 1.36 (d, J = 6.5 Hz, 3H), 1.41-1.12 (m, 6H), 0.87 (t, J = 6.8 Hz, 3H) $^{13}$C NMR (75 MHz, CDCl$_3$) δ 172.56, 158.37, 154.96, 129.51, 121.14, 114.54, 79.62, 78.18, 74.40, 67.35, 60.20, 51.28, 39.92, 34.67, 28.32, 27.53, 27.25, 23.31, 19.29, 13.82 |

*$^1$H NMR were run at 400 MHz unless noted otherwise.
*$^{13}$C NMR were run at 101 MHz unless noted otherwise.
*$^{19}$F NMR were run at 376 MHz unless noted otherwise.

TABLE 3

Biological Testing Rating Scale Rating Table for Fungal Pathogens

| % Control | Rating |
|---|---|
| >70 | A |
| ≤70 | B |
| Not Tested | C |

TABLE 4

Biological Activity - PUCCRT and SEPTTR Disease Control in High and Low Volume Applications

| | Low Volume (121.5 g/H*) | | | | High Volume (100 ppm*) | | | |
|---|---|---|---|---|---|---|---|---|
| | PUCCRT* | | SEPTTR* | | PUCCRT* | | SEPTTR* | |
| *Cmpd. No. | 1 DP* | 3 DC* | 1 DP* | 3 DC* | 1 DP* | 3 DC* | 1 DP* | 3 DC* |
| 1 | A | A | A | A | C | C | C | C |
| 2 | A | A | A | A | C | C | C | C |
| 3 | A | A | A | A | C | C | C | C |
| 4 | A | A | A | A | C | C | C | C |
| 5 | A | A | A | B | C | C | C | C |
| 6 | A | A | A | A | C | C | C | C |
| 7 | A | A | A | A | C | C | C | C |
| 8 | A | A | A | B | C | C | C | C |
| 9 | A | A | A | A | C | C | C | C |
| 10 | A | A | A | A | C | C | C | C |
| 11 | A | A | A | B | C | C | C | C |
| 12 | A | A | A | A | C | C | C | C |
| 13 | A | A | A | A | C | C | C | C |
| 14 | A | A | A | B | C | C | C | C |
| 15 | A | A | A | A | C | C | C | C |
| 16 | A | A | B | B | C | C | C | C |
| 17 | A | A | A | A | A | A | A | A |
| 18 | A | A | A | A | C | C | C | C |
| 19 | A | A | A | A | C | C | C | C |
| 20 | A | A | A | A | C | C | C | C |
| 21 | A | A | A | B | C | C | C | C |
| 22 | A | A | A | A | C | C | C | C |
| 23 | A | A | A | A | C | C | C | C |
| 24 | A | A | A | A | C | C | C | C |
| 25 | A | A | B | B | C | C | C | C |
| 26 | A | A | A | A | C | C | C | C |
| 27 | A | A | A | A | C | C | C | C |
| 28 | A | A | A | A | C | C | C | C |
| 29 | A | A | A | A | C | C | C | C |
| 30 | A | A | A | A | C | C | C | C |
| 31 | A | A | A | A | C | C | C | C |
| 32 | A | A | A | A | C | C | C | C |
| 33 | C | C | C | C | C | C | C | C |
| 34 | A | A | B | B | C | C | C | C |
| 35 | A | A | A | A | C | C | C | C |
| 36 | A | A | A | B | C | C | C | C |
| 37 | A | A | A | A | C | C | C | C |
| 38 | A | A | A | A | C | C | C | C |
| 39 | A | A | A | B | C | C | C | C |
| 40 | A | A | A | A | C | C | C | C |
| 41 | A | A | A | A | C | C | C | C |
| 42 | A | A | A | A | C | C | C | C |
| 43 | A | A | A | A | A | A | A | A |
| 44 | A | A | A | A | C | C | C | C |
| 45 | A | A | A | A | C | C | C | C |
| 46 | A | A | A | B | C | C | C | C |
| 47 | A | A | A | A | C | C | C | C |
| 48 | A | A | B | B | C | C | C | C |
| 49 | C | C | C | C | C | C | C | C |
| 50 | C | C | C | C | A | A | A | A |
| 51 | C | C | C | C | C | C | C | C |
| 52 | C | C | C | C | C | C | C | C |
| 53 | C | C | C | C | C | C | C | C |
| 54 | C | C | C | C | C | C | C | C |
| 55 | C | C | C | C | A | A | A | A |
| 56 | C | C | C | C | A | A | B | A |
| 57 | C | C | C | C | A | B | A | A |
| 58 | C | C | C | C | C | C | C | C |
| 59 | C | C | C | C | A | A | A | A |
| 60 | C | C | C | C | C | C | C | C |
| 61 | C | C | C | C | C | C | C | C |

TABLE 4-continued

Biological Activity - PUCCRT and SEPTTR Disease Control in High and Low Volume Applications

| *Cmpd. | Low Volume (121.5 g/H*) | | | | High Volume (100 ppm*) | | | |
|---|---|---|---|---|---|---|---|---|
| | PUCCRT* | | SEPTTR* | | PUCCRT* | | SEPTTR* | |
| No. | 1 DP* | 3 DC* | 1 DP* | 3 DC* | 1 DP* | 3 DC* | 1 DP* | 3 DC* |
| 62 | C | C | C | C | C | C | C | C |
| 63 | C | C | C | C | C | C | C | C |
| 64 | C | C | C | C | A | A | A | A |
| 65 | C | C | C | C | C | C | C | C |
| 66 | C | C | C | C | C | C | C | C |
| 67 | C | C | C | C | A | A | A | B |
| 68 | C | C | C | C | A | A | A | B |

*Cmpd. No. - Compound Number
*PUCCRT - Wheat Brown Rust (*Puccinia triticina*)
*SEPTTR - Wheat Leaf Blotch (*Zymoseptoria tritici*)
*1 DP - 1 Day Protectant
*3 DC - 3 Day Curative
*g/H - Grams Per Hectare
*ppm - Parts Per Million

TABLE 5

Biological Activity - Disease Control at 100 ppm

| *Cmpd. No. | ALTESO* | CERCBE* | COLLLA* 1DP* | ERYSCI* | ERYSGH* |
|---|---|---|---|---|---|
| 2 | B | A | A | B | B |
| 3 | B | A | A | B | B |
| 17 | B | A | A | B | B |

*Cmpd. No. - Compound Number
*ALTESO - Tomato Early Blight (*Alternaria solani*)
*CERCBE - Leaf Spot of Sugar Beets (*Cercospora beticola*)
*COLLLA - Cucumber Anthracnose (*Glomerella lagenarium*; Anamorph: *Colletotricum lagenarium*)
*ERYSCI - Powdery Mildew of Cucumber (*Erysiphe cichoracearum*)
*ERYSGH - Barley Powdery Mildew (*Blumeria graminis* f. sp. *hordei*; Synonym: *Erysiphe graminis* f. sp. *hordei*)
*1DP - 1 Day Protectant

TABLE 6

Biological Activity - Disease Control at 100 ppm

| *Cmpd. No. | LEPTNO* | PYRIOR* | RHYNSE* 1DP | UNCINE* | VENTIN* |
|---|---|---|---|---|---|
| 2 | A | A | A | C | C |
| 3 | A | A | B | C | C |
| 17 | A | A | B | A | B |

*Cmpd. No. - Compound Number
*LEPTNO - Wheat Glume Blotch (*Leptosphaeria nodorum*)
*PYRIOR - Rice Blast (*Magnaporthe grisea*)
*RHYNSE - Barley Scald (*Rhyncosporium secalis*)
*UNCINE - Grape Powdery Mildew (*Uncinula necator*)
*VENTIN - Apple Scab (*Venturia inaequalis*)
*1DP - 1 Day Protectant

TABLE 7

Biological Activity - Disease Control at 25 ppm

| *Cmpd. No. | PHAKPA* | |
|---|---|---|
| | 1DP* | 3DC* |
| 17 | A | A |
| 43 | A | A |

*Cmpd. No. - Compound Number
*PHAKPA - Asian Soybean Rust (*Phakopsora pachyrhizi*)
*1DP - 1 Day Protectant
*3DC - 3 Day Curative

What is claimed is:

1. A compound of Formula I

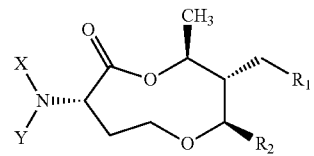

wherein
X is hydrogen or $C(O)R_3$;
Y is or Q;
Q is

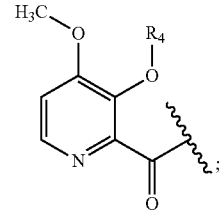

$R_1$ is hydrogen, alkyl, alkenyl, aryl, alkoxy, each optionally substituted with 0, 1 or multiple $R_6$;
$R_2$ is hydrogen, alkyl, alkenyl, or aryl, each optionally substituted with 0, 1 or multiple $R_6$, or $R_2$ is $-CH_2-O-C(O)CH(CH_3)_2$;
$R_3$ is alkoxy or benzyloxy, each optionally substituted with 0, 1, or multiple $R_6$;
$R_4$ is hydrogen, $-C(O)R_5$, or $-CH_2OC(O)R_5$;
$R_5$ is alkyl, alkoxy, or aryl, each optionally substituted with 0, 1, or multiple $R_6$;
$R_6$ is hydrogen, alkyl, aryl, halo, alkenyl, alkoxy, or thioalkyl, each optionally substituted with 0, 1, or multiple $R_7$; and
$R_7$ is hydrogen, alkyl, aryl, or halo.

2. The compound according to claim 1, wherein X is hydrogen.

3. The compound according to claim 2, wherein $R_1$ is alkyl or aryl, each optionally substituted with 0, 1 or multiple $R_6$.

4. The compound according to claim 2, wherein $R_2$ is hydrogen or alkyl, each optionally substituted with 0, 1 or multiple $R_6$.

5. The compound according to claim 1, wherein X is $C(O)R_3$.

6. The compound according to claim 5, wherein $R_1$ is alkyl or aryl, each optionally substituted with 0, 1 or multiple $R_6$.

7. The compound according to claim 5, wherein $R_2$ is hydrogen or alkyl, each optionally substituted with 0, 1 or multiple $R_6$.

8. The compound according to claim 1, wherein X is hydrogen and Y is Q.

9. The compound according to claim 8, wherein $R_1$ is alkyl or aryl, each optionally substituted with 0, 1 or multiple $R_6$.

10. The compound according to claim 8, wherein $R_2$ is hydrogen or alkyl, each optionally substituted with 0, 1 or multiple $R_6$.

11. The compound according to claim 9, wherein $R_4$ is hydrogen.

12. The compound according to claim 9, wherein $R_4$ is —C(O)$R_5$ or —CH$_2$OC(O)$R_5$.

13. The compound according to claim 12, wherein $R_5$ is alkyl or alkoxy, each optionally substituted with 0, 1, or multiple $R_6$.

14. The compound according to claim 13, wherein $R_5$ is —CH$_3$, —CH(CH$_3$)$_2$, —CH$_2$OCH$_2$CH$_3$, or —CH$_2$CH$_2$OCH$_3$.

* * * * *